(12) United States Patent
Radetich et al.

(10) Patent No.: US 8,987,257 B2
(45) Date of Patent: Mar. 24, 2015

(54) HETEROCYCLIC DERIVATIVES

(75) Inventors: Branko Radetich, Boston, MA (US); Bing Yu, Cambridge, MA (US); Yanyi Zhu, Acton, MA (US)

(73) Assignee: Novartis AG, Basel (CH)

( * ) Notice: Subject to any disclaimer, the term of this patent is extended or adjusted under 35 U.S.C. 154(b) by 83 days.

(21) Appl. No.: 13/361,365

(22) Filed: Jan. 30, 2012

(65) Prior Publication Data

US 2012/0220576 A1  Aug. 30, 2012

Related U.S. Application Data

(60) Provisional application No. 61/437,956, filed on Jan. 31, 2011, provisional application No. 61/552,905, filed on Oct. 28, 2011.

(51) Int. Cl.
*C07D 487/04* (2006.01)

(52) U.S. Cl.
CPC .................. *C07D 487/04* (2013.01)
USPC ...................... 514/232.5; 544/118

(58) Field of Classification Search
CPC .................................... C07D 487/04
USPC ...................... 544/118; 514/232.5
See application file for complete search history.

(56) References Cited

U.S. PATENT DOCUMENTS

| 3,016,378 A * | 1/1962 | Roch ............................. 544/81 |
| 2011/0086840 A1 | 4/2011 | Pei et al. |
| 2011/0086841 A1 | 4/2011 | Pei et al. |

FOREIGN PATENT DOCUMENTS

| GB | 864145 | 3/1961 |
| WO | WO9320078 A1 | 10/1993 |
| WO | WO2006128129 A2 | 11/2006 |
| WO | WO2006128172 A2 | 11/2006 |
| WO | 2010/002954 | 1/2010 |
| WO | 2010/056320 | 5/2010 |
| WO | WO2011025889 A1 | 3/2011 |
| WO | WO2011078795 A1 | 6/2011 |
| WO | WO2013/061305 | 5/2013 |

OTHER PUBLICATIONS

Wang et al., JACS, 127:4996-4997 (2005).
Zhao et al., J. Org. Chem., 73:7428-7431 (2008).

* cited by examiner

*Primary Examiner* — Rebecca Anderson
(74) *Attorney, Agent, or Firm* — Laura Madden

(57) ABSTRACT

The invention relates to novel heterocyclic compounds of the formula

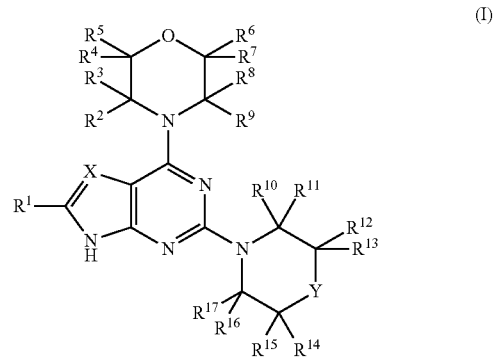

in which all of the variables are as defined in the specification, to their preparation, to their medical use, in particular to their use in the treatment of cancer and neurodegenerative disorders, and to medicaments comprising them.

13 Claims, No Drawings

HETEROCYCLIC DERIVATIVES

This application claims priority to U.S. Provisional Application Ser. No. 61/437,956 filed 31 Jan. 2011 and U.S. Provisional Application Ser. No. 61/552,905 filed 28 Oct. 2011, the contents of which are incorporated herein by reference in their entirety.

FIELD OF THE INVENTION

The invention relates to purine derivatives and pharmaceutically acceptable salts thereof, processes for their preparation, their use in the treatment of diseases, their use, either alone or in combination with at least one additional therapeutic agent and optionally in combination with a pharmaceutically acceptable carrier, for the manufacture of pharmaceutical preparations, use of the pharmaceutical preparations for the treatment of diseases, and a method of treatment of said diseases, comprising administering the purine derivatives to a warm-blooded animal, especially a human.

BACKGROUND OF THE INVENTION

The phosphatidylinositol-3-kinases superfamily comprises 4 different PI3K related lipid or protein kinases. Class I, II and III are lipid kinases that differ by virtue of their substrate specificities whereas class IV PI3Ks (also called PIKKs) are protein kinases. Class I phosphatidylinositol-3-kinases comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., *Annu. Rev. Biochem.* 70:535 (2001); Katso et al., *Annu. Rev. Cell Dev. Biol.* 17:615 (2001)). Of the two Class I PI3Ks, Class IA PI3Ks are heterodimers composed of a catalytic p110 subunit (α, β, δ, isoforms) constitutively associated with a regulatory subunit that can be p85α, p55α, p50α, p85β or p55γ. The Class IB sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class IA PI3Ks. Class IB PI3K is activated directly by G protein-coupled receptors that bind a diverse repertoire of peptide and non-peptide ligands (Stephens et al., *Cell* 89:105 (1997)); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., *Cell* 69:413-423 (1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers. Furthermore, mutations and translocation of p85α that serve to up-regulate the p85-p110 complex have been described in human cancers. Also, somatic missense mutations in PIK3CA that activate downstream signaling pathways have been described at significant frequencies in a wide diversity of human cancers (Kang at al., *Proc. Natl. Acad. Sci. USA* 102:802 (2005); Samuels et al., *Science* 304:554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey et al., *Nature Rev. Drug Disc.* 4:988-1004 (2005)).

The mammalian target of rapamycin (mTOR) is a member of the class IV PI3K. mTOR assembles a signaling network that transduces nutrient signals and various other stimuli to regulate a wide range of cellular functions including cell growth, proliferation, survival, autophagy, various types of differentiation and metabolism. In mammalian cells, the mTOR protein is found complexed in two distinct entities called mTORC1 and mTORC2. The mTORC1 complex, that is to say mTOR associated with raptor, has been the matter of numerous studies. It is mTORC1 that integrates nutrient and growth factor inputs, and is in turn responsible for cell growth regulation, mainly through protein synthesis regulators such as 4EBP1 or RPS6. mTORC1 regulation requires PI3K and Akt activation for activation, meaning that mTORC1 is an effector of the PI3K pathway. mTOR when associated in the mTOR complex 2 (mTORC2) has been shown to be responsible for the activation of Akt by phosphorylation of S473 (Akt 1 numbering) (Sarbassov et al., *Science* 307:7098 (2005)). mTORC2 is hence here considered as an upstream activator of Akt. Interestingly mTOR can therefore be considered as being important both upstream and downstream of Akt. mTOR catalytic inhibition might therefore represent a unique way of addressing a very strong block in the PI3K-Akt pathway, by addressing both upstream and downstream effectors.

A link between mTOR inhibition and autophagy has also been demonstrated (Ravikumar et al., *Nat. Genet.* 36(6):585-95 (2004)). Autophagy is essential for neuronal homeostasis and its dysfunction has been linked to neurodegeneration. Loss of autophagy in neurons causes neurodegenerative disease in mice (Komatsu et al., *Nature* 441:880-4 (2006); Hara et al., *Nature* 441:885-9 (2006)) suggesting a critical role for autophagy to maintain protein homeostasis in neurons. Neurodegenerative diseases are characterized by inclusions of misfolded proteins as one of the hallmarks. Induction of autophagy enhances clearance of misfolded proteins and thus is proposed as therapy for neurodegenerative proteinopathies.

Huntington's Disease (HD) is an autosomal dominant neurodegenerative disorder where a mutation of IT15 gene encoding the Huntingtin (Htt) protein leads to Polyglutamine expansion in Exon1 of Htt. Intracellular aggregation of this mutant Htt protein and brain atrophy (in particular cortex and striatum) are the main hallmarks of HD. It clinically leads to movement disturbance and cognitive dysfunction besides psychiatric disturbances and weight loss.

Inhibition of mTOR induces autophagy and reduces mutant Htt aggregation and mutant Htt-mediated cell death in in vitro and in vivo models of HD (Ravikumar et al., *Nat. Genet.* 36(6):585-95 (2004)). mTOR inhibition therefore provides an opportunity for pharmaceutical intervention and modulation of the disrupted cellular processes characteristic of HD.

In view of the above, inhibitors of class I PI3Ks and mTOR are considered to be of value in the treatment of proliferative diseases and other disorders, in particular, HD.

The present invention relates to novel purine derivatives having class I PI3K and/or mTOR inhibitory activity, their preparation, medical use and to medicaments comprising them.

SUMMARY OF THE INVENTION

In a first aspect, the invention relates to a compound of formula (I), or a pharmaceutically acceptable salt thereof,

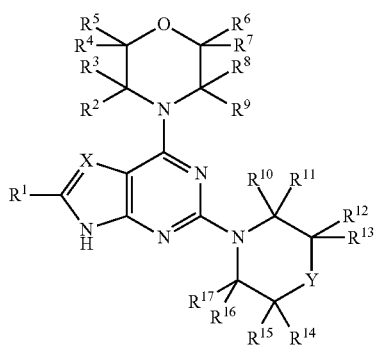
(I)

wherein
X represents N or CH;
$R^1$ represents

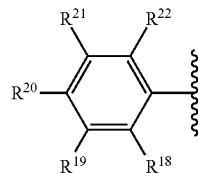

wherein
$R^{18}$ and $R^{22}$ independently represent hydrogen, halogen, hydroxy or hydroxy-$C_{1-3}$alkyl-;
$R^{19}$ and $R^{21}$ independently represent hydrogen, amino, hydroxy, carboxy, $C_{1-3}$alkoxy, amino-$C_{1-3}$alkyl-, $C_{1-3}$alkyl-C(=O)—NH—, $C_{1-3}$alkyl-S(=O)$_m$—NH— or hydroxy-$C_{1-3}$alkyl-;
m represents 0, 1 or 2;
$R^{20}$ represents hydrogen, halogen or $C_{1-3}$alkoxy; or
$R^1$ is selected from the group consisting of

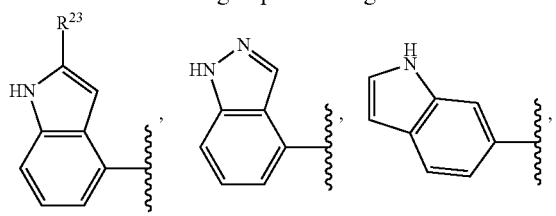

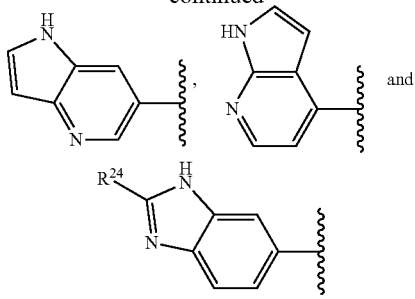

wherein
$R^{23}$ represents hydrogen or methyl;
$R^{24}$ represents hydrogen, oxo or $C_{1-3}$alkyl;
$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ independently represent hydrogen or methyl;
or $R^2$ and $R^8$ together form an ethylene bridge;
or $R^2$ and $R^6$ together form a methylene bridge;
or $R^{12}$ and $R^{14}$ together form an ethylene bridge; and
Y represents O, CHR$^{25}$ or CR$^{26}$R$^{27}$
wherein
$R^{25}$ represents hydroxy or $C_{1-3}$alkoxy; and
$R^{26}$ and $R^{27}$ independently represent hydrogen or halogen;
with the proviso that the compound of formula (I) is other than 2,6-di-morpholin-4-yl-8-phenyl-9H-purine.

In a second aspect, the invention relates to a compound of formula (I), or a pharmaceutically acceptable salt thereof,

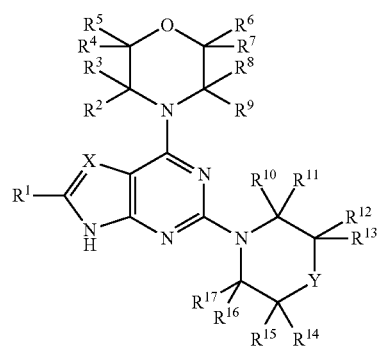
(I)

wherein
X represents N or CH;
$R^1$ represents

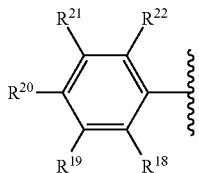

wherein
$R^{18}$ and $R^{22}$ independently represent hydrogen, halogen, hydroxy or hydroxy-$C_{1-3}$alkyl-;
$R^{19}$ and $R^{21}$ independently represent hydrogen, amino, hydroxy, carboxy, $C_{1-3}$alkoxy, amino-$C_{1-3}$alkyl-, $C_{1-3}$alkyl-C(=O)—NH—, $C_{1-3}$alkyl-S(=O)$_m$—NH— or hydroxy-$C_{1-3}$alkyl-;
m represents 0, 1 or 2;
$R^{20}$ represents hydrogen, halogen or $C_{1-3}$alkoxy; or $R^1$ is selected from the group consisting of

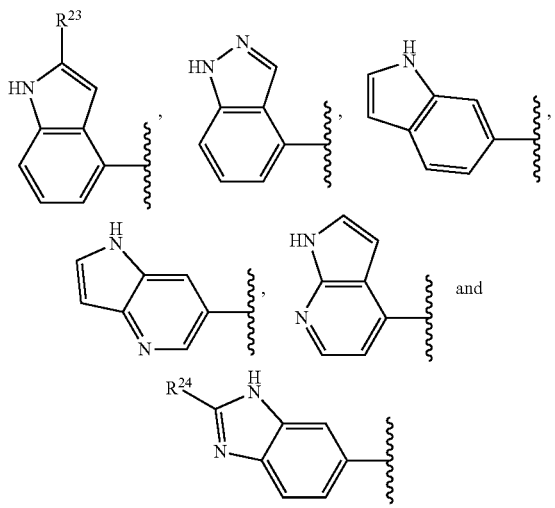

wherein
$R^{23}$ represents hydrogen or methyl;
$R^{24}$ represents hydrogen, oxo or $C_{1-3}$alkyl;
$R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ independently represent hydrogen or methyl; or
$R^5$ and $R^6$ together form an ethylene bridge; and
Y represents O, $CHR^{25}$ or $CR^{26}R^{27}$
wherein
$R^{25}$ represents hydroxy or $C_{1-3}$alkoxy; and
$R^{26}$ and $R^{27}$ independently represent hydrogen or halogen;
with the proviso that the compound of formula (I) is other than 2,6-di-morpholin-4-yl-8-phenyl-9H-purine.

DEFINITIONS

As used herein, the term "halogen" or "halo" refers to fluoro, chloro, bromo, and iodo.

As used herein, the term "$C_{1-3}$alkyl" refers to a fully saturated branched or unbranched hydrocarbon moiety having up to 3 carbon atoms. Representative examples of $C_{1-3}$alkyl include methyl, ethyl, n-propyl and iso-propyl.

As used herein, the term "$C_{1-3}$alkoxy" refers to $C_{1-3}$alkyl-O—, wherein $C_{1-3}$alkyl is as defined herein above. Representative examples of $C_{1-3}$alkoxy include methoxy, ethoxy, propoxy and 2-propoxy.

As used herein, the term "hydroxy-$C_{1-3}$alkyl" refers to a $C_{1-3}$alkyl group as defined herein above, wherein one of the hydrogen atoms of the $C_{1-3}$alkyl group is replaced by OH. Representative examples of hydroxy-$C_{1-3}$alkyl include, but are not limited to, hydroxyl-methyl, 2-hydroxy-ethyl, 2-hydroxy-propyl and 3-hydroxy-propyl.

As used herein, the term "amino-$C_{1-3}$alkyl" refers to a $C_{1-3}$alkyl group as defined herein above, wherein one of the hydrogen atoms of the $C_{1-3}$alkyl group is replaced by a primary amino group. Representative examples of hydroxy-$C_{1-3}$alkyl include, but are not limited to, amino-methyl, 2-amino-ethyl, 2-amino-propyl and 3-amino-propyl.

DETAILED DESCRIPTION OF THE INVENTION

The present invention provides compounds and pharmaceutical formulations thereof that may be useful in the treatment or prevention of diseases, conditions and/or disorders modulated by the inhibition of class I PI3Ks and/or mTOR.

Embodiment 1 a compound of formula (I), or a pharmaceutically acceptable salt thereof, as described hereinbefore.

Embodiment 2 a compound of formula (I), or a pharmaceutically acceptable salt thereof, as described hereinbefore.

Embodiment 3 a compound according to Embodiment 1 or Embodiment 2, or a pharmaceutically acceptable salt thereof, wherein X represents N.

Embodiment 4 a compound according to Embodiment 1 or Embodiment 2, or a pharmaceutically acceptable salt thereof, wherein X represents CH.

Embodiment 5 a compound according to any one of Embodiments 1 to 4, or a pharmaceutically acceptable salt thereof, wherein $R^1$ represents

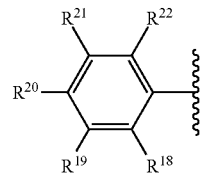

wherein
$R^{18}$ and $R^{22}$ independently represent hydrogen, halogen, hydroxy or hydroxy-$C_{1-3}$alkyl-;
$R^{19}$ and $R^{21}$ independently represent hydrogen, amino, hydroxy, carboxy, $C_{1-3}$alkoxy, amino-$C_{1-3}$alkyl-, $C_{1-3}$alkyl-C(=O)—NH—, $C_{1-3}$alkyl-S(=O)$_m$—NH— or hydroxy-$C_{1-3}$alkyl-;
m represents 0, 1 or 2; and
$R^{20}$ represents hydrogen, halogen or $C_{1-3}$alkoxy.

Embodiment 6 a compound according to Embodiment 5, or a pharmaceutically acceptable salt thereof, wherein at least one of $R^{18}$, $R^{19}$, $R^{20}$, $R^{21}$ and $R^{22}$ is not hydrogen.

Embodiment 7 a compound according to any one of Embodiments 1 to 4, or a pharmaceutically acceptable salt thereof, wherein $R^1$ is selected from the group consisting of

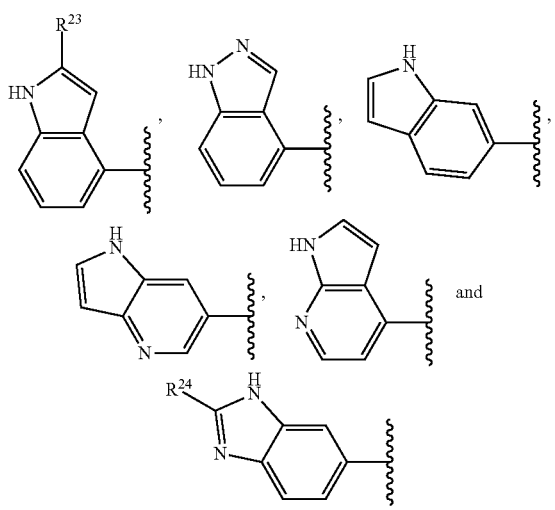

wherein
R²³ represents hydrogen or methyl; and
R²⁴ represents hydrogen, oxo or C₁₋₃alkyl.

Embodiment 8 a compound according to any one of Embodiments 1 to 7, or a pharmaceutically acceptable salt thereof, wherein Y represents O;

Embodiment 9 a compound according to any one of Embodiments 1 to 7, or a pharmaceutically acceptable salt thereof, wherein Y represents CHR²⁶ or CR²⁷R²⁸.

Embodiment 10 a compound according to Embodiment 1 or Embodiment 2, which is selected from:
3-[2-(2,6-Dimethyl-morpholin-4-yl)-6-morpholin-4-yl-9H-purin-8-yl]-phenol;
3-(2,4-dimorpholino-7H-pyrrolo[2,3-d]pyrimidin-6-yl)phenol;
2,6-Bis-(3-methyl-morpholin-4-yl)-8-(1H-pyrrolo[2,3-b]pyridin-4-yl)-9H-purine;
{2-Fluoro-5-[6-(3-methyl-morpholin-4-yl)-2-morpholin-4-yl-9H-purin-8-yl]-phenyl}-methanol;
2-(4,4-Difluoro-piperidin-1-yl)-8-(1H-indol-4-yl)-6-(3-methyl-morpholin-4-yl)-9H-purine;
5-[2,6-Bis-(3-methyl-morpholin-4-yl)-9H-purin-8-yl]-1,3-dihydro-benzoimidazol-2-one;
{5-[2,6-Bis-(3-methyl-morpholin-4-yl)-9H-purin-8-yl]-2-methoxy-phenyl}-methanol;
8-(1H-Indol-4-yl)-2-morpholin-4-yl-6-(8-oxa-3-aza-bicyclo[3.2.1]oct-3-yl)-9H-purine;
2-Methoxy-5-[6-(3-methyl-morpholin-4-yl)-2-morpholin-4-yl-9H-purin-8-yl]-benzoic acid;
{4-Chloro-3-[6-(3-methyl-morpholin-4-yl)-2-morpholin-4-yl-9H-purin-8-yl]-phenyl}-methanol;
3-(2,6-Di-morpholin-4-yl-9H-purin-8-yl)-benzylamine;
1-{3-[6-(3-Methyl-morpholin-4-yl)-2-morpholin-4-yl-9H-purin-8-yl]-phenyl}-ethanol;
2,6-Di-morpholin-4-yl-8-(1H-pyrrolo[3,2-b]pyridin-6-yl)-9H-purine;
8-(1H-Indol-6-yl)-2,6-bis-(3-methyl-morpholin-4-yl)-9H-purine;
8-(1H-Indol-4-yl)-2,6-bis-(3-methyl-morpholin-4-yl)-9H-purine;
1-[8-(1H-Indol-4-yl)-6-(3-methyl-morpholin-4-yl)-9H-purin-2-yl]-piperidin-4-ol;
{3-[2,6-Bis-(3-methyl-morpholin-4-yl)-9H-purin-8-yl]-5-methoxy-phenyl}-methanol;
8-(1H-Indol-4-yl)-2-(3-methyl-morpholin-4-yl)-6-(3-methyl-morpholin-4-yl)-9H-purine;
{3-[2,6-Bis-(3-methyl-morpholin-4-yl)-9H-purin-8-yl]-4-fluoro-phenyl}-methanol;
8-(1H-Indol-4-yl)-6-(3-methyl-morpholin-4-yl)-2-morpholin-4-yl-9H-purine;
8-(1H-Indol-6-yl)-6-(3-methyl-morpholin-4-yl)-2-morpholin-4-yl-9H-purine;
8-(1H-Indol-4-yl)-2,6-bis-(3-methyl-morpholin-4-yl)-9H-purine;
8-(1H-Indol-4-yl)-6-(3-methyl-morpholin-4-yl)-2-morpholin-4-yl-9H-purine;
8-(1H-Indol-6-yl)-6-(3-methyl-morpholin-4-yl)-2-morpholin-4-yl-9H-purine;
8-(1H-Indol-4-yl)-2-(4-methoxy-piperidin-1-yl)-6-morpholin-4-yl-9H-purine;
8-(1H-Indol-4-yl)-2,6-di-morpholin-4-yl-9H-purine;
8-(1H-Indazol-4-yl)-2,6-di-morpholin-4-yl-9H-purine;
8-(1H-Indol-6-yl)-2,6-di-morpholin-4-yl-9H-purine;
3-(2,6-Di-morpholin-4-yl-9H-purin-8-yl)-phenylamine;
N-[3-(2,6-Di-morpholin-4-yl-9H-purin-8-yl)-phenyl]acetamide;
8-(2-Methyl-1H-indol-4-yl)-2,6-di-morpholin-4-yl-9H-purine;
3-[2-(2,6-Dimethyl-morpholin-4-yl)-6-morpholin-4-yl-9H-purin-8-yl]-phenylamine;
N-[3-(2,6-Di-morpholin-4-yl-9H-purin-8-yl)-phenyl]-methanesulfonamide;
{2-[2-(2,6-Dimethyl-morpholin-4-yl)-6-morpholin-4-yl-9H-purin-8-yl]-phenyl}-methanol;
[2-(2,6-Di-morpholin-4-yl-9H-purin-8-yl)-phenyl]methanol;
3-(2,6-Di-morpholin-4-yl-9H-purin-8-yl)-phenol;
[3-(2,6-Di-morpholin-4-yl-9H-purin-8-yl)-phenyl]methanol;
2-(2,6-Di-morpholin-4-yl-9H-purin-8-yl)-phenol;
3-[2-(2,6-Dimethyl-morpholin-4-yl)-6-morpholin-4-yl-9H-purin-8-yl]-phenol;
3-(2,4-dimorpholino-7H-pyrrolo[2,3-d]pyrimidin-6-yl)phenol;
2,6-Bis-(3-methyl-morpholin-4-yl)-8-(1H-pyrrolo[2,3-b]pyridin-4-yl)-9H-purine;
{2-Fluoro-5-[6-(3-methyl-morpholin-4-yl)-2-morpholin-4-yl-9H-purin-8-yl]-phenyl}-methanol;
2-(4,4-Difluoro-piperidin-1-yl)-8-(1H-indol-4-yl)-6-(3-methyl-morpholin-4-yl)-9H-purine;
5-[2,6-Bis-(3-methyl-morpholin-4-yl)-9H-purin-8-yl]-1,3-dihydro-benzoimidazol-2-one;
{5-[2,6-Bis-(3-methyl-morpholin-4-yl)-9H-purin-8-yl]-2-methoxy-phenyl}-methanol;
8-(1H-Indol-4-yl)-2-morpholin-4-yl-6-(8-oxa-3-aza-bicyclo[3.2.1]oct-3-yl)-9H-purine;
2-Methoxy-5-[6-(3-methyl-morpholin-4-yl)-2-morpholin-4-yl-9H-purin-8-yl]-benzoic acid;
{4-Chloro-3-[6-(3-methyl-morpholin-4-yl)-2-morpholin-4-yl-9H-purin-8-yl]-phenyl}-methanol;
3-(2,6-Di-morpholin-4-yl-9H-purin-8-yl)-benzylamine;
1-{3-[6-(3-Methyl-morpholin-4-yl)-2-morpholin-4-yl-9H-purin-8-yl]-phenyl}-ethanol;

2,6-Di-morpholin-4-yl-8-(1H-pyrrolo[3,2-b]pyridin-6-yl)-9H-purine;
8-(1H-Indol-6-yl)-2,6-bis-(3-methyl-morpholin-4-yl)-9H-purine;
8-(1H-Indol-4-yl)-2,6-bis-(3-methyl-morpholin-4-yl)-9H-purine;
1-[8-(1H-Indol-4-yl)-6-(3-methyl-morpholin-4-yl)-9H-purin-2-yl]-piperidin-4-ol;
{3-[2,6-Bis-(3-methyl-morpholin-4-yl)-9H-purin-8-yl]-5-methoxy-phenyl}-methanol;
8-(1H-Indol-4-yl)-2-(3-methyl-morpholin-4-yl)-6-((S)-3-methyl-morpholin-4-yl)-9H-purine;
{3-[2,6-Bis-(3-methyl-morpholin-4-yl)-9H-purin-8-yl]-4-fluoro-phenyl}-methanol;
8-(1H-Indol-4-yl)-6-(3-methyl-morpholin-4-yl)-2-morpholin-4-yl-9H-purine;
8-(1H-Indol-6-yl)-6-(3-methyl-morpholin-4-yl)-2-morpholin-4-yl-9H-purine;
8-(1H-Indol-4-yl)-2,6-bis-(3-methyl-morpholin-4-yl)-9H-purine;
8-(1H-Indol-4-yl)-6-(3-methyl-morpholin-4-yl)-2-morpholin-4-yl-9H-purine;
8-(1H-Indol-6-yl)-6-(3-methyl-morpholin-4-yl)-2-morpholin-4-yl-9H-purine;
8-(1H-Indol-4-yl)-2-(4-methoxy-piperidin-1-yl)-6-morpholin-4-yl-9H-purine;
8-(1H-Indol-4-yl)-2,6-di-morpholin-4-yl-9H-purine;
8-(1H-Indazol-4-yl)-2,6-di-morpholin-4-yl-9H-purine;
8-(1H-Indol-6-yl)-2,6-di-morpholin-4-yl-9H-purine;
3-(2,6-Di-morpholin-4-yl-9H-purin-8-yl)-phenylamine;
N-[3-(2,6-Di-morpholin-4-yl-9H-purin-8-yl)-phenyl]acetamide;
8-(2-Methyl-1H-indol-4-yl)-2,6-di-morpholin-4-yl-9H-purine;
3-[2-(2,6-Dimethyl-morpholin-4-yl)-6-morpholin-4-yl-9H-purin-8-yl]-phenylamine;
N-[3-(2,6-Di-morpholin-4-yl-9H-purin-8-yl)-phenyl]-methanesulfonamide;
{2-[2-(2,6-Dimethyl-morpholin-4-yl)-6-morpholin-4-yl-9H-purin-8-yl]-phenyl}-methanol;
[2-(2,6-Di-morpholin-4-yl-9H-purin-8-yl)-phenyl]methanol;
3-(2,6-Di-morpholin-4-yl-9H-purin-8-yl)-phenol;
[3-(2,6-Di-morpholin-4-yl-9H-purin-8-yl)-phenyl]-methanol;
2-(2,6-Di-morpholin-4-yl-9H-purin-8-yl)-phenol;
6-(3,3-Dimethyl-morpholin-4-yl)-8-(1H-indol-6-yl)-2-morpholin-4-yl-9H-purine;
6-(3,3-Dimethyl-morpholin-4-yl)-8-(1H-indol-4-yl)-2-morpholin-4-yl-9H-purine;
8-(2,3-Dihydro-1H-indol-4-yl)-2-(3-methyl-morpholin-4-yl)-6-(3-methyl-morpholin-4-yl)-9H-purine;
8-(2,3-Dihydro-1H-indol-4-yl)-2,6-bis-(3-methyl-morpholin-4-yl)-9H-purine;
8-(1H-Indol-4-yl)-2-(3-methyl-morpholin-4-yl)-6-((R)-3-methyl-morpholin-4-yl)-9H-purine;
8-(1H-Indol-6-yl)-2-(3-methyl-morpholin-4-yl)-6-((R)-3-methyl-morpholin-4-yl)-9H-purine;
8-(1H-Indol-6-yl)-2,6-bis-(3-methyl-morpholin-4-yl)-9H-purine;
8-(1H-Indol-4-yl)-6-(3-methyl-morpholin-4-yl)-2-(8-oxa-3-aza-bicyclo[3.2.1]oct-3-yl)-9H-purine;
8-(1H-Indol-4-yl)-2-(3-methyl-morpholin-4-yl)-6-morpholin-4-yl-9H-purine;
8-(1H-Indol-6-yl)-2-morpholin-4-yl-6-(2-oxa-5-aza-bicyclo[2.2.1]hept-5-yl)-9H-purine;
8-(1H-Indol-4-yl)-2-(3-methyl-morpholin-4-yl)-6-morpholin-4-yl-9H-purine;
8-(1H-Indol-4-yl)-2-morpholin-4-yl-6-(2-oxa-5-aza-bicyclo[2.2.1]hept-5-yl)-9H-purine;
8-(1H-Indol-6-yl)-6-(3-methyl-morpholin-4-yl)-2-(8-oxa-3-aza-bicyclo[3.2.1]oct-3-yl)-9H-purine;
8-(1H-Indol-6-yl)-6-(3-methyl-morpholin-4-yl)-2-(8-oxa-3-aza-bicyclo[3.2.1]oct-3-yl)-9H-purine;
8-(1H-Indol-6-yl)-2-morpholin-4-yl-6-(3-oxa-8-aza-bicyclo[3.2.1]oct-8-yl)-9H-purine;
8-(1H-Indol-4-yl)-2-morpholin-4-yl-6-(3-oxa-8-aza-bicyclo[3.2.1]oct-8-yl)-9H-purine;
6-(1H-Indol-4-yl)-4-(3-methyl-morpholin-4-yl)-2-(3-methyl-morpholin-4-yl)-7H-pyrrolo[2,3-d]pyrimidine;
6-(1H-Indol-4-yl)-2,4-di-morpholin-4-yl-7H-pyrrolo[2,3-d]pyrimidine;
and pharmaceutically acceptable salts thereof.

Embodiment 11 a compound according to Embodiment 1 or Embodiment 2, which is selected from:
3-[2-((2S,6R)-2,6-Dimethyl-morpholin-4-yl)-6-morpholin-4-yl-9H-purin-8-yl]-phenol;
3-(2,4-dimorpholino-7H-pyrrolo[2,3-d]pyrimidin-6-yl)phenol;
2,6-Bis-((S)-3-methyl-morpholin-4-yl)-8-(1H-pyrrolo[2,3-b]pyridin-4-yl)-9H-purine;
{2-Fluoro-5-[6-((S)-3-methyl-morpholin-4-yl)-2-morpholin-4-yl-9H-purin-8-yl]-phenyl}-methanol;
2-(4,4-Difluoro-piperidin-1-yl)-8-(1H-indol-4-yl)-6-((S)-3-methyl-morpholin-4-yl)-9H-purine;
5-[2,6-Bis-((S)-3-methyl-morpholin-4-yl)-9H-purin-8-yl]-1,3-dihydro-benzoimidazol-2-one;
{5-[2,6-Bis-((S)-3-methyl-morpholin-4-yl)-9H-purin-8-yl]-2-methoxy-phenyl}-methanol;
8-(1H-Indol-4-yl)-2-morpholin-4-yl-6-(8-oxa-3-aza-bicyclo[3.2.1]oct-3-yl)-9H-purine;
2-Methoxy-5-[6-((S)-3-methyl-morpholin-4-yl)-2-morpholin-4-yl-9H-purin-8-yl]-benzoic acid;
{4-Chloro-3-[6-((S)-3-methyl-morpholin-4-yl)-2-morpholin-4-yl-9H-purin-8-yl]-phenyl}-methanol;
3-(2,6-Di-morpholin-4-yl-9H-purin-8-yl)-benzylamine;
1-{3-[6-((S)-3-Methyl-morpholin-4-yl)-2-morpholin-4-yl-9H-purin-8-yl]-phenyl}-ethanol;
2,6-Di-morpholin-4-yl-8-(1H-pyrrolo[3,2-b]pyridin-6-yl)-9H-purine;
8-(1H-Indol-6-yl)-2,6-bis-((S)-3-methyl-morpholin-4-yl)-9H-purine;
8-(1H-Indol-4-yl)-2,6-bis-((R)-3-methyl-morpholin-4-yl)-9H-purine;
1-[8-(1H-Indol-4-yl)-6-((S)-3-methyl-morpholin-4-yl)-9H-purin-2-yl]-piperidin-4-ol;
{3-[2,6-Bis-((S)-3-methyl-morpholin-4-yl)-9H-purin-8-yl]-5-methoxy-phenyl}-methanol;
8-(1H-Indol-4-yl)-2-((R)-3-methyl-morpholin-4-yl)-6-((S)-3-methyl-morpholin-4-yl)-9H-purine;
{3-[2,6-Bis-((R)-3-methyl-morpholin-4-yl)-9H-purin-8-yl]-4-fluoro-phenyl}-methanol;
8-(1H-Indol-4-yl)-6-((R)-3-methyl-morpholin-4-yl)-2-morpholin-4-yl-9H-purine;
8-(1H-Indol-6-yl)-6-((R)-3-methyl-morpholin-4-yl)-2-morpholin-4-yl-9H-purine;
8-(1H-Indol-4-yl)-2,6-bis-((S)-3-methyl-morpholin-4-yl)-9H-purine;
8-(1H-Indol-4-yl)-6-((S)-3-methyl-morpholin-4-yl)-2-morpholin-4-yl-9H-purine;

8-(1H-Indol-6-yl)-6-((S)-3-methyl-morpholin-4-yl)-2-morpholin-4-yl-9H-purine;
8-(1H-Indol-4-yl)-2-(4-methoxy-piperidin-1-yl)-6-morpholin-4-yl-9H-purine;
8-(1H-Indol-4-yl)-2,6-di-morpholin-4-yl-9H-purine;
8-(1H-Indazol-4-yl)-2,6-di-morpholin-4-yl-9H-purine;
8-(1H-Indol-6-yl)-2,6-di-morpholin-4-yl-9H-purine;
3-(2,6-Di-morpholin-4-yl-9H-purin-8-yl)-phenylamine;
N-[3-(2,6-Di-morpholin-4-yl-9H-purin-8-yl)-phenyl]-acetamide;
8-(2-Methyl-1H-indol-4-yl)-2,6-di-morpholin-4-yl-9H-purine;
3-[2-((2S,6R)-2,6-Dimethyl-morpholin-4-yl)-6-morpholin-4-yl-9H-purin-8-yl]-phenylamine;
N-[3-(2,6-Di-morpholin-4-yl-9H-purin-8-yl)-phenyl]-methanesulfonamide;
{2-[2-((2S,6R)-2,6-Dimethyl-morpholin-4-yl)-6-morpholin-4-yl-9H-purin-8-yl]-phenyl}-methanol;
[2-(2,6-Di-morpholin-4-yl-9H-purin-8-yl)-phenyl]-methanol;
3-(2,6-Di-morpholin-4-yl-9H-purin-8-yl)-phenol;
[3-(2,6-Di-morpholin-4-yl-9H-purin-8-yl)-phenyl]-methanol;
2-(2,6-Di-morpholin-4-yl-9H-purin-8-yl)-phenol;
3-[2-((2S,6R)-2,6-Dimethyl-morpholin-4-yl)-6-morpholin-4-yl-9H-purin-8-yl]-phenol;
3-(2,4-dimorpholino-7H-pyrrolo[2,3-d]pyrimidin-6-yl)phenol;
2,6-Bis-((S)-3-methyl-morpholin-4-yl)-8-(1H-pyrrolo[2,3-b]pyridin-4-yl)-9H-purine;
{2-Fluoro-5-[6-((S)-3-methyl-morpholin-4-yl)-2-morpholin-4-yl-9H-purin-8-yl]-phenyl}-methanol;
2-(4,4-Difluoro-piperidin-1-yl)-8-(1H-indol-4-yl)-6-((S)-3-methyl-morpholin-4-yl)-9H-purine;
5-[2,6-Bis-((S)-3-methyl-morpholin-4-yl)-9H-purin-8-yl]-1,3-dihydro-benzoimidazol-2-one;
{5-[2,6-Bis-((S)-3-methyl-morpholin-4-yl)-9H-purin-8-yl]-2-methoxy-phenyl}-methanol;
8-(1H-Indol-4-yl)-2-morpholin-4-yl-6-(8-oxa-3-aza-bicyclo[3.2.1]oct-3-yl)-9H-purine;
2-Methoxy-5-[6-((S)-3-methyl-morpholin-4-yl)-2-morpholin-4-yl-9H-purin-8-yl]-benzoic acid;
{4-Chloro-3-[6-((S)-3-methyl-morpholin-4-yl)-2-morpholin-4-yl-9H-purin-8-yl]-phenyl}-methanol;
3-(2,6-Di-morpholin-4-yl-9H-purin-8-yl)-benzylamine;
1-{3-[6-((S)-3-Methyl-morpholin-4-yl)-2-morpholin-4-yl-9H-purin-8-yl]-phenyl}-ethanol;
2,6-Di-morpholin-4-yl-8-(1H-pyrrolo[3,2-b]pyridin-6-yl)-9H-purine;
8-(1H-Indol-6-yl)-2,6-bis-((S)-3-methyl-morpholin-4-yl)-9H-purine;
8-(1H-Indol-4-yl)-2,6-bis-((R)-3-methyl-morpholin-4-yl)-9H-purine;
1-[8-(1H-Indol-4-yl)-6-((S)-3-methyl-morpholin-4-yl)-9H-purin-2-yl]-piperidin-4-ol;
{3-[2,6-Bis-((S)-3-methyl-morpholin-4-yl)-9H-purin-8-yl]-5-methoxy-phenyl}-methanol;
8-(1H-Indol-4-yl)-2-((R)-3-methyl-morpholin-4-yl)-6-((S)-3-methyl-morpholin-4-yl)-9H-purine;
{3-[2,6-Bis-((R)-3-methyl-morpholin-4-yl)-9H-purin-8-yl]-4-fluoro-phenyl}-methanol;
8-(1H-Indol-4-yl)-6-((R)-3-methyl-morpholin-4-yl)-2-morpholin-4-yl-9H-purine;
8-(1H-Indol-6-yl)-6-((R)-3-methyl-morpholin-4-yl)-2-morpholin-4-yl-9H-purine;
8-(1H-Indol-4-yl)-2,6-bis-((S)-3-methyl-morpholin-4-yl)-9H-purine;
8-(1H-Indol-4-yl)-6-((S)-3-methyl-morpholin-4-yl)-2-morpholin-4-yl-9H-purine;
8-(1H-Indol-6-yl)-6-((S)-3-methyl-morpholin-4-yl)-2-morpholin-4-yl-9H-purine;
8-(1H-Indol-4-yl)-2-(4-methoxy-piperidin-1-yl)-6-morpholin-4-yl-9H-purine;
8-(1H-Indol-4-yl)-2,6-di-morpholin-4-yl-9H-purine;
8-(1H-Indazol-4-yl)-2,6-di-morpholin-4-yl-9H-purine;
8-(1H-Indol-6-yl)-2,6-di-morpholin-4-yl-9H-purine;
3-(2,6-Di-morpholin-4-yl-9H-purin-8-yl)-phenylamine;
N-[3-(2,6-Di-morpholin-4-yl-9H-purin-8-yl)-phenyl]-acetamide;
8-(2-Methyl-1H-indol-4-yl)-2,6-di-morpholin-4-yl-9H-purine;
3-[2-((2S,6R)-2,6-Dimethyl-morpholin-4-yl)-6-morpholin-4-yl-9H-purin-8-yl]-phenylamine;
N-[3-(2,6-Di-morpholin-4-yl-9H-purin-8-yl)-phenyl]-methanesulfonamide;
{2-[2-((2S,6R)-2,6-Dimethyl-morpholin-4-yl)-6-morpholin-4-yl-9H-purin-8-yl]-phenyl}-methanol;
[2-(2,6-Di-morpholin-4-yl-9H-purin-8-yl)-phenyl]methanol;
3-(2,6-Di-morpholin-4-yl-9H-purin-8-yl)-phenol;
[3-(2,6-Di-morpholin-4-yl-9H-purin-8-yl)-phenyl]-methanol;
2-(2,6-Di-morpholin-4-yl-9H-purin-8-yl)-phenol;
6-(3,3-Dimethyl-morpholin-4-yl)-8-(1H-indol-6-yl)-2-morpholin-4-yl-9H-purine;
6-(3,3-Dimethyl-morpholin-4-yl)-8-(1H-indol-4-yl)-2-morpholin-4-yl-9H-purine;
8-(2,3-Dihydro-1H-indol-4-yl)-2-((S)-3-methyl-morpholin-4-yl)-6-((R)-3-methyl-morpholin-4-yl)-9H-purine;
8-(2,3-Dihydro-1H-indol-4-yl)-2,6-bis-((R)-3-methyl-morpholin-4-yl)-9H-purine;
8-(1H-Indol-4-yl)-2-((S)-3-methyl-morpholin-4-yl)-6-((R)-3-methyl-morpholin-4-yl)-9H-purine;
8-(1H-Indol-6-yl)-2-((S)-3-methyl-morpholin-4-yl)-6-((R)-3-methyl-morpholin-4-yl)-9H-purine;
8-(1H-Indol-6-yl)-2,6-bis-((R)-3-methyl-morpholin-4-yl)-9H-purine;
8-(1H-Indol-4-yl)-6-((R)-3-methyl-morpholin-4-yl)-2-(8-oxa-3-aza-bicyclo[3.2.1]oct-3-yl)-9H-purine;
8-(1H-Indol-4-yl)-2-((R)-3-methyl-morpholin-4-yl)-6-morpholin-4-yl-9H-purine;
8-(1H-Indol-6-yl)-2-morpholin-4-yl-6-(1S,4S)-2-oxa-5-aza-bicyclo[2.2.1]hept-5-yl-9H-purine;
8-(1H-Indol-4-yl)-2-((S)-3-methyl-morpholin-4-yl)-6-morpholin-4-yl-9H-purine;
8-(1H-Indol-4-yl)-2-morpholin-4-yl-6-(1S,4S)-2-oxa-5-aza-bicyclo[2.2.1]hept-5-yl-9H-purine;
8-(1H-Indol-6-yl)-6-((S)-3-methyl-morpholin-4-yl)-2-(8-oxa-3-aza-bicyclo[3.2.1]oct-3-yl)-9H-purine;
8-(1H-Indol-4-yl)-6-((S)-3-methyl-morpholin-4-yl)-2-(8-oxa-3-aza-bicyclo[3.2.1]oct-3-yl)-9H-purine;
8-(1H-Indol-6-yl)-2-morpholin-4-yl-6-(3-oxa-8-aza-bicyclo[3.2.1]oct-8-yl)-9H-purine;
8-(1H-Indol-4-yl)-2-morpholin-4-yl-6-(3-oxa-8-aza-bicyclo[3.2.1]oct-8-yl)-9H-purine;
6-(1H-Indol-4-yl)-4-((R)-3-methyl-morpholin-4-yl)-2-((S)-3-methyl-morpholin-4-yl)-7H-pyrrolo[2,3-d]pyrimidine;
6-(1H-Indol-4-yl)-2,4-di-morpholin-4-yl-7H-pyrrolo[2,3-d]pyrimidine;
and pharmaceutically acceptable salts thereof.

On account of one or more than one asymmetrical carbon atom, which may be present in a compound of the formula (I), a corresponding compound of the formula (I) may exist in pure optically active form or in the form of a mixture of optical isomers, e.g. in the form of a racemic mixture. All of such pure optical isomers and all of their mixtures, including the racemic mixtures, are part of the present invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)- isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

In one embodiment, the invention relates to a compound of the formula (I) as defined herein, in free form. In another embodiment, the invention relates to a compound of the formula (I) as defined herein, in salt form. In another embodiment, the invention relates to a compound of the formula (I) as defined herein, in acid addition salt form. In a further embodiment, the invention relates to a compound of the formula (I) as defined herein, in pharmaceutically acceptable salt form. In yet a further embodiment, the invention relates to any one of the compounds of the Examples in free form. In yet a further embodiment, the invention relates to any one of the compounds of the Examples in salt form. In yet a further embodiment, the invention relates to any one of the compounds of the Examples in acid addition salt form. In yet a further embodiment, the invention relates to any one of the compounds of the Examples in pharmaceutically acceptable salt form.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The compounds of the present invention, including salts, hydrates and solvates thereof, may inherently or by design form polymorphs.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In a further aspect, the invention relates to a process for the preparation of a compound of the formula (I), in free form or in pharmaceutically acceptable salt form, comprising (a) when X represents N in a compound of formula (I), the reaction of a compound of formula (IIa)

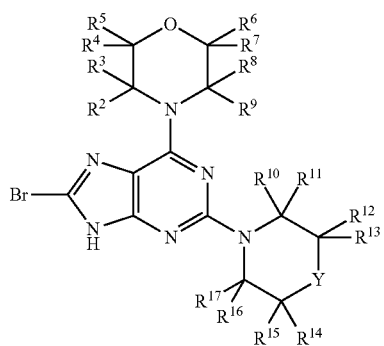

(IIa)

in which $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined for formula (I), with a compound of formula (III) or (IV)

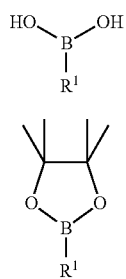

(III)

(IV)

in which $R^1$ is as defined for formula (I), or b) when X represents CH in a compound of formula (I), the reaction of a compound of formula (IIb)

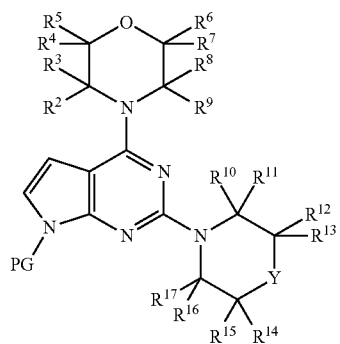

(IIb)

in which $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined for formula (I) and PG is a protecting group, with a compound of formula (III) or (IV)

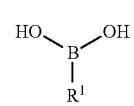

(III)

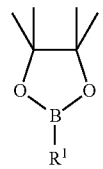

(IV)

in which $R^1$ is as defined for formula (I),
and thereafter
i) the optional reduction, oxidation or other functionalisation of the resulting compound,
ii) the cleavage of any protecting group(s) present,
iii) the recovery of the so obtainable compound of the formula (I) in free form or in pharmaceutically acceptable salt form, and/or
iv) the optional separation of mixtures of optically active isomers into their individual optically active isomeric forms.

The reactions can be effected according to conventional methods. For example, the reaction described in step (a) above may be carried out in the presence of a suitable metal catalyst, for example tetrakis(triphenylphosphine)palladium, a suitable base, for example cesium fluoride, a suitable solvent, for example acetonitrile/water and at a suitable temperature, for example 50 to 150° C., more suitably 90 to 130° C.

The reaction described in step (b) above may be carried out in the presence of a suitable catalyst, for example palladium (II) acetate, a suitable oxidant, for example copper (II) acetate, a suitable solvent, for example acetic acid, and at a suitable temperature, for example 0 to 50° C., or more suitably room temperature.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

For those compounds containing an asymmetric carbon atom, the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof. In addition, the present invention embraces all geometric and positional isomers. For example, if a compound of the present invention incorporates a double bond or a fused ring, both the cis- and trans- forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a commercially available chiral HPLC column.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

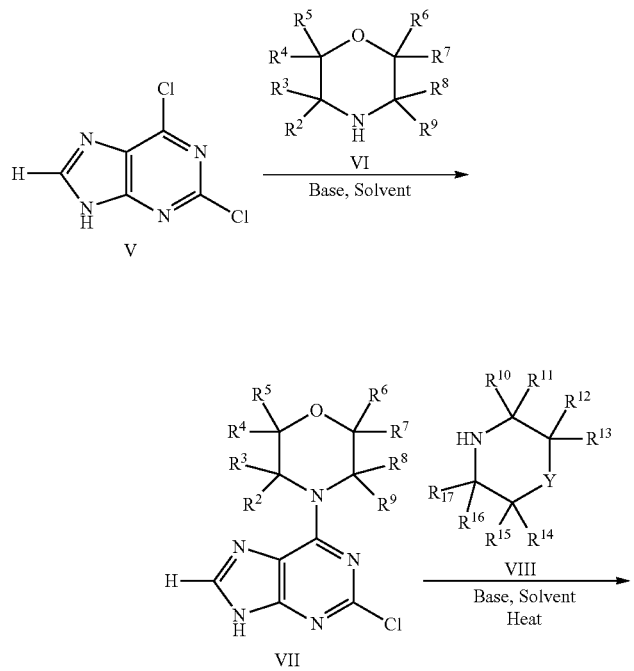

Scheme 1. General procedure 1 for synthesis of purine compounds

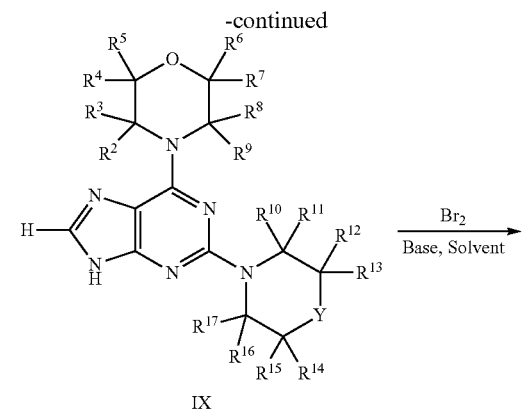

IX

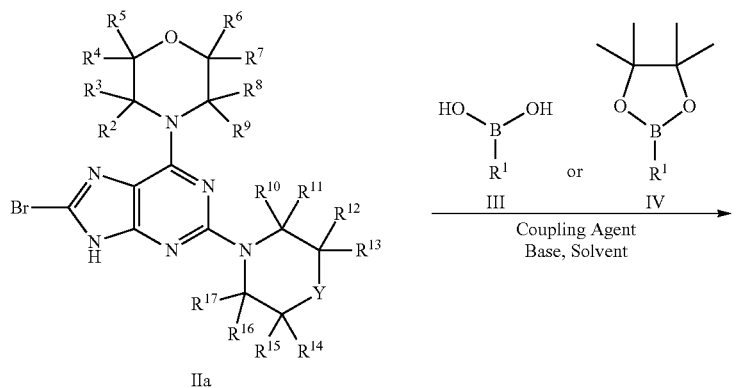

IIa

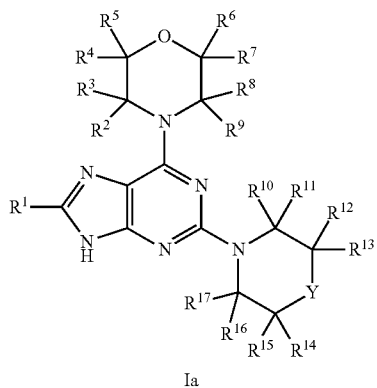

Ia

Generally, the compounds of formula Ia can be prepared according to Scheme 1 in four steps, starting from commercially available intermediate V. As to the individual steps in the scheme shown above, step one involves preparation of the intermediate VII by chlorine displacement with nucleophile such as functionalized morpholino intermediate VI. Intermediate IX can be prepared by reaction of intermediate VII with intermediate VIII in presence of adequate base such as diisopropylethyl amine, solvent such as dimethyl acetamide and heat. Step three involves bromination of the intermediate IX to intermediate IIa that can be done utilizing bromine in appropriate solvent such as dichloromethane.

Target compounds of structure Ia can be prepared by coupling of intermediate II with variety of commercially available or synthesized boronic acids or esters of structure III or IV using metal catalysts most often exemplified by commercially available palladium complexes.

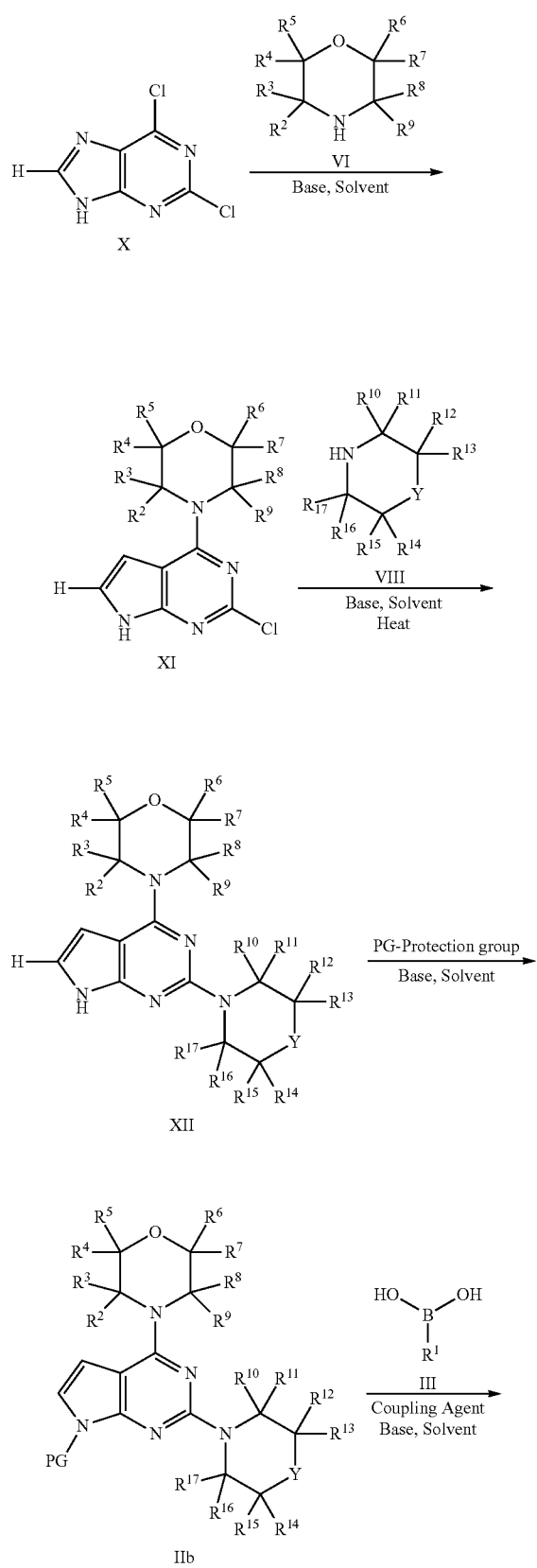

Scheme 2. General procedure for synthesis of pyrrolo pyrimidine compounds

Generally, the compounds of formula Ib can be prepared according to Scheme 2 in five steps, starting from commercially available intermediate X. As to the individual steps in the Scheme 2, step one involves preparation of intermediate XI by chlorine displacement with nucleophile such as functionalized morpholino intermediate VI. Intermediate XII can be prepared by reacting intermediate XI with intermediate VIII in the presence of solvent such as dimethyl acetamide, base such as diisopropylethyl amine and heat. Step three involves protection of intermediate XII to intermediate IIb using adequate protection group such as benzylchloride or SEM-Chloride in the presence of base such as sodium hydride and solvent such as tetrahydrofuran. Step four involves coupling of intermediate IIb with adequate boronic acid in presence of adequate solvent such as acetic acid, oxidant such as copper acetate and commercially available palladium catalyst. Final step to target compounds exemplified by structure Ib involve the removal of the protection group using acid base or adequate catalysts such as palladium.

Scheme 3. General Procedure for synthesis of boronic esters.

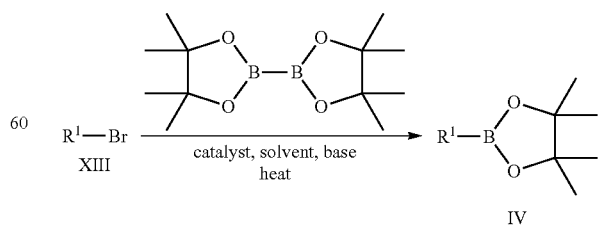

Boronic esters of formula IV can be prepared according to Scheme 3 in one step where $R^1$ is as described in formula (I).

The step involves reacting substituted arylbromide or heteroarylbromide of formula XIII with bis(pinacolato)diboron in the presence of commercially available palladium catalyst, solvent such as dioxane at temperature ranging from 80° C. to 120° C.

Compounds of the formula (I), in free form or in pharmaceutically acceptable salt form, hereinafter often referred to as "agents of the invention", exhibit valuable pharmacological properties, when tested in vitro, and may, therefore, be useful in medicaments, in therapy or for use as research chemicals, for example as tool compounds.

The agents of the invention are inhibitors of class I PI3Ks and mTOR. The inhibiting properties of a compound of the invention towards class I PI3Ks and mTOR can be evaluated in tests as described hereinafter.

Biological Assays

Test 1: PI3 Kinase Assay

PI3K KinaseGlo assay: 50 mL of compound dilutions were dispensed onto black 384-well low volume Non Binding Styrene (NBS) plates (Costar Cat. No. NBS#3676). L-a-phosphatidylinositol (PI), provided as 10 mg/ml solution in methanol, was transferred into a glass tube and dried under nitrogen beam. It was then resuspended in 3% OctylGlucoside (OG) by vortexing and stored at 4° C. The KinaseGlo Luminescent Kinase Assay (Promega, Madison/WI, USA) is a homogeneous HTS method of measuring kinase activity by quantifying the amount of ATP remaining in solution following a kinase reaction.

5 μL of a mix of PI/OG with the PI3K subtype were added (Table 1). Kinase reactions were started by addition of 5 μl of ATP-mix containing in a final volume 10 μL 10 mM TRIS-HCl pH 7.5, 3 mM $MgCl_2$, 50 mM NaCl, 0.05% CHAPS, 1 mM DTT and 1 μM ATP, and occurred at room temperature. Reactions were stopped with 10 μl of KinaseGlo and plates were read 10 mins later in a Synergy2 reader using an integration time of 0.1 seconds per well. 2.5 μM of a pan-class 1 PI3 kinase inhibitor (standard) was added to the assay plates to generate the 100% inhibition of the kinase reaction, and the 0% inhibition was given by the solvent vehicle (90% DMSO in water). The standard was used as a reference compound and included in all assay plates in the form of 16 dilution points in duplicate.

Cloning of PI3Ks

The PI3Kα construct is a fusion of p85α iSH2 domain and the respective p110 isoform. The p85α fragment and p110 isoform gene were generated by PCR from first strand cDNA generated by RT-PCR from commercial RNA from placenta, testis and brain as described below.

PI3Kα Constructs and Proteins

BV1075: The construct for Baculovirus BV-1075 was generated by a three-part ligation comprised of a p85 fragment and a p110α fragment cloned into vector pBlueBac4.5. The p85 fragment was derived from plasmid p1661-2 digested with Nhe/Spe. The p110α fragment derived from its clone was verified by sequencing and used in LR410 as a SpeI/HindIII fragment. For the generation of the baculovirus expression vector LR410 the gateway LR reaction to transfer the insert into the Gateway adapted pBlueBac4.5 (Invitrogen) vector was used. The cloning vector pBlueBac4.5 (Invitrogen) was digested with Nhe/HindIII. This resulted in the construct PED 153.8. The p85 component (iSH2) was generated by PCR using ORF 318 as a template and one forward primer KAC1028 (5'-gctagcatgcgagaatatgatagat-tatatgaag-aatatacc) (SEQ ID NO: 1) and two reverse primers, KAC1029 (5'-gcctccaccac-ctccgcctg-gtttaatgctgttcatacgtttgtc) (SEQ ID NO: 2) and KAC1039 (5'-tactagtc-cgcctccac-cacctccgcctc-caccacctccgcc) (SEQ ID NO: 3). The two reverse primers overlap and incorporate a 12×Gly linker and the N-terminal sequence of the p110α gene to the SpeI site. The PCR fragment was cloned into pCR2.1 TOPO (Invitrogen). Of the resulting clones, p1661-2 was determined to be correct by sequencing. This plasmid was digested with Nhe and SpeI and the resulting fragment was gel-isolated and purified for sub-cloning.

The p110α cloning fragment was generated by enzymatic digest of clone LR410 (see above) with Spe I and HindIII. The SpeI site is in the coding region of the p110α gene. The resulting fragment was gel-isolated and purified for sub-cloning. The cloning vector, pBlueBac4.5 (Invitrogen) was prepared by enzymatic digestion with Nhe and HindIII. The cut vector was purified with Qiagen column and then dephosphorylated with Calf Intestine alkaline phosphatase (CIP) (BioLabs). After completion of the CIP reaction the cut vector was again column purified to generate the final vector. A three-part ligation was performed using Roche Rapid ligase and the vendor specifications. The final plasmid was verified by sequencing.

Protein Sequence of BV 1075 (SEQ ID NO: 4):

(SEQ ID NO: 4)

```
  1 MREYDRLYEE YTRTSQEIQM KRTAIEAFNE TIKIFEEQCQ TQERYSKEYI EKFKREGNEK

61 EIQRIMHNYD KLKSRISEII DSRRRLEEDL KKQAAEYREI DKRMNSIKPG GGGGGGGGGG

121 GLVECLLPNG MIVTLECLRE ATLITIKHEL FKEARKYPLH QLLQDESSYI FVSVTQEAER

181 EEFFDETRRL CDLRLFQPFL KVIEPVGNRE EKILNREIGF AIGMPVCEFD MVKDPEVQDF

241 RRNILNVCKE AVDLRDLNSP HSRAMYVYPP NVESSPELPK HIYNKLDKGQ IIVVIWVIVS

301 PNNDKQKYTL KINHDCVPEQ VIAEAIRKKT RSMLLSSEQL KLCVLEYQGK YILKVCGCDE

361 YFLEKYPLSQ YKYIRSCIML GRMPNLMLMA KESLYSQLPM DCFTMPSYSR RISTATPYMN

421 GETSTKSLWV INSALRIKIL CATYVNVNIR DIDKIYVRTG IYHGGEPLCD NVNTQRVPCS

481 NPRWNEWLNY DIYIPDLPRA ARLCLSICSV KGRKGAKEEH CPLAWGNINL FDYTDTLVSG

541 KMALNLWPVP HGLEDLLNPI GVTGSNPNKE TPCLELEFDW FSSVVKFPDM SVIEEHANWS

601 VSREAGFSYS HAGLSNRLAR DNELRENDKE QLKAISTRDP LSEITEQEKD FLWSHRHYCV

661 TIPEILPKLL LSVKWNSRDE VAQMYCLVKD WPPIKPEQAM ELLDCNYPDP MVRGFAVRCL
```

```
 721  EKYLTDDKLS  QYLIQLVQVL  KYEQYLDNLL  VRFLLKKALT  NQRIGHFFFW  HLKSEMHNKT

781  VSQRFGLLLE  SYCRACGMYL  KHLNRQVEAM  EKLINLTDIL  KQEKKDETQK  VQMKFLVEQM

841  RRPDFMDALQ  GFLSPLNPAH  QLGNLRLEEC  RIMSSAKRPL  WLNWENPDIM  SELLFQNNEI

901  IFKNGDDLRQ  DMLTLQIIRI  MENIWQNQGL  DLRMLPYGCL  SIGDCVGLIE  VVRNSHTIMQ

961  IQCKGGLKGA  LQFNSHTLHQ  WLKDKNKGEI  YDAAIDLFTR  SCAGYCVATF  ILGIGDRHNS

1021  NIMVKDDGQL  FHIDFGHFLD  HKKKKFGYKR  ERVPFVLTQD  FLIVISKGAQ  ECTKTREFER

1081  FQEMCYKAYL  AIRQHANLFI  NLFSMMLGSG  MPELQSFDDI  AYIRKTLALD  KTEQEALEYF

1141  MKQMNDAHHG  GWTTKMDWIF  HTIKQHALNE  LGGAHHHHHH
```

Purification of PI3Kα Constructs

PI3Kα was purified in two chromatographic steps: immobilized metal affinity chromatography (IMAC) on a Ni sepharose resin (GE Healthcare) and gel filtration utilizing a Superdex 200 26/60 column (GE Healthcare). All buffers were chilled to 4° C. and lysis was performed chilled on ice. Column fractionation was performed at room temperature.

Typically frozen cells from 10 L of Tn5 cell culture were resuspended in "Lysis Buffer" 20 mM Tris-Cl, pH 7.5, 500 mM NaCl, 5% glycerol, 5 mM imidazole, 1 mM NaF, 0.1 ug/mL okadaic acid (OAA), 5 mM BME, 1× Complete protease inhibitor cocktail—EDTA-free (20 tablets/1 L buffer, Roche Applied Sciences), benzonase (25 U/mL buffer, EMD Biosciences) at a ratio of 1:6 v/v pellet to Lysis Buffer ratio, and mechanically lysed by douncing for 20 strokes using a tight-fitting pestle. The lysate was centrifuged at 45,000 g for 30 minutes, and the supernatant was loaded onto a pre-equilibrated IMAC column (3 mL resin/100 mL lysate). The column was washed with 3-5 column volumes of Lysis Buffer, followed by a second wash of 3-5 column volumes with 20 mM Tris-Cl, pH 7.5, 500 mM NaCl, 5% glycerol, 45 mM imidazole, 1 mM NaF, 0.1 μg/mL OAA, 5 mM BME, 1× Complete protease inhibitor cocktail—EDTA-free. Protein was eluted with 20 mM Tris-Cl, pH 7.5, 0.5 M NaCl, 5% glycerol, 250 mM imidazole, 1 mM NaF, 0.1 μg/mL OAA, 5 mM BME, 1× Complete protease inhibitor cocktail—EDTA-free. Pertinent fractions were analyzed by SDS-PAGE and pooled accordingly. The protein was further purified by gel filtration on a Superdex 200 26/60 column equilibrated in 20 mM Tris-Cl, pH 7.5, 0.5 M NaCl, 5% glycerol, 1 mM NaF, 5 mM DTT, 1× Complete protease inhibitor cocktail—EDTA-free. Pertinent fractions were analyzed by SDS-PAGE and pooled accordingly. An equal volume of Dialysis Buffer (20 mM Tris-Cl, pH 7.5, 500 mM NaCl, 50% glycerol, 5 mM NaF, 5 mM DTT) was added to the pool and than dialyzed against Dialysis Buffer two changes (one change overnight). Protein was stored at −20° C.

Test 2: mTOR Biochemical Assay

IC50s for mTOR interacting compounds were assessed using the FRAP1/mTOR TR-FRET tracer assay (Invitrogen by Life Technologies). FRAP1/mTOR (PV4753) and LanthaScreen Eu-Anti-GST Antibody (PV5594) (total volume of 14 μL) were added to each well of a ProxiPlate-384 Plus (Perkin-Elmer) 384-well plate. Compounds were serially diluted in DMSO (12-point, 4× dilution factor) and 1 μL of diluted compound was then added to each well and mixed by pipetting using a Biomek FX (Beckman Coulter). 5 μL of mTOR Kinase Tracer 314 (PV6087) was added to each well, mixed and plates were incubated at room temperature for 1 hour. Final concentrations of components are: 6 nM FRAP1/3 nM LanthaScreen Eu-Anti-GST Antibody/50 nM mTOR Kinase Tracer 314/unlabeled compounds, $4.8*10^{-6}$-20 μM. Final assay buffer composition is: 50 mM HEPES (pH 7.5), 50 mM NaCl, 5 mM $MgCl_2$, 1 mM EGTA, 0.01% Pluronic F-127. Plates were measured in plate reader (Perkin Elmer, EnVision) using 340 nm excitation and emission at two wavelengths, Emission-1 665 nm and Emission-2 615 nm. The TR-FRET ratio for each well (Emission-1 665/Emission-2 615) was plotted against compound concentration using GraphPad Prism software and IC50s were determined using nonlinear regression with outlier elimination.

Test 3: TSC Assay

The following is a description of a high content imaging assay, utilizing TSC1−/− mouse embryonic fibroblasts (MEFs) cells, to test compounds for the inhibition of a constitutively active mTOR. The assay is based on the staining of phospho-S6 (240/244) using a commercially available antibody and detection with a fluorescently labeled secondary antibody. This assay generates IC50 values for compounds that inhibit mTOR. Here is described an imaging protocol and image recognition algorithm to visualize and measure changes in pS6 240/244 levels.

Quantification of pS6 Staining Using High-Content Imaging and Analysis

1. Day 0: Cell plating. Subconfluent TSC1−/− MEFs are harvested by trypsinization, resuspended in growth medium, and counted. A cell suspension of 166,666 cells/mL is prepared and 30 μL is added into the wells of a 384-well plate using an electronic multichannel pipette. This results in 5000 cells/well being plated. The plates are briefly spun down and placed at 37° C. and 5% $CO_2$.

2. Day 1: Cell plates are washed into a PBS starve solution (contains glucose, sodium bicarbonate, HEPES and phenol red) using a 384-well plate washer. The wash protocol aspirates the volume down to 30 μL/well before dispensing 60 μL/well of the PBS starve solution. Aspiration and dispensing steps are repeated 8 times and a final volume of 30 μL/well is left. The cell plates are placed at 37° C. and 5% $CO_2$ for 2 hrs.

Compound treatment. Compound dose responses are prepared in DMSO. The dose responses are then diluted 1:50 in medium. 10 ul of the diluted compound is added to 30 ul of cells, yielding a final 1:200 dilution of the original compound and final of 0.5% DMSO. Compound-treatments are performed in triplicates. The plates are placed at 37° C. and 5% $CO_2$ for 2 hrs. Cells are then fixed by adding 10 μL/well 5× concentrated Mirsky's fixative. This results in a total volume of 50 μL per well and a concentration of 1× Mirsky's fixative. The cell plates are briefly spun down and incubated for 1 h at room temperature. Cells are then washed using a 384-well plate washer using a protocol which aspirates the volume down to 30 µL/well before dispensing 60 µL/well 1×TBS. Aspiration and dispensing steps are repeated 8 times and then an additional aspiration step leaves a final volume of 10 µL/well. Block buffer (1×TBS+0.1% Triton X-100+0.1% BSA) is then added at 25 µL/well and the plates are incubated at room temperature for 30 min. The cell plates are then aspirated down to 10 µL/well. Primary antibody (Phospho-S6 Ribosomal Protein (Ser240/244) (61H9) Rabbit mAb Cell Signaling #4838) is diluted 1:150 in block buffer and then 10 µL/well is added to the cell plates. Plates are incubated overnight at 4° C.

3. Day 2: Cell plates are washed using 1×TBS method detailed above and then a secondary antibody solution is added at 10 µL/well (secondary antibody solution: block buffer+Hoechst 10 ug/ml+goat anti-rabbit Cy5 secondary (diluted 1:150)) (Goat anti-rabbit IgG Cy5: Chemicon International #AP187/Hoechst 33342: Invitrogen #H3570). Plates are incubated for 1 hr at room temperature and then washed with 1×TBS using the protocol detailed above without the final aspiration step which results in a final volume of 90 µL TBS/well.

Imaging. The bottom of the plate is cleaned with 70% ethanol and then imaged using the InCell 1000 automated epifluorescence microscope. 10× magnification is used and 1 area (field) is imaged per well, this typically captures a total of around 400 cells per well. Hoechst33342 images are acquired using an excitation of 360 nm (D360_40× filter), an emission of 460 nM (HQ460_40M filter) and an exposure time of 200 ms. Cy5 images are acquired using an excitation of 620 nm (Chroma 620_60× filter), an emission of 700 nM (Chroma HQ700_75M filter) and an exposure time of 200 ms. A double band pass mirror is used for all images.

4. Image analysis: The InCell Analysis software is used to analyze the images using the Dual Object algorithm. First, nuclei are detected in the Hoechst33342 image using top-hat segmentation and a minimal nuclear area of 10 µm². Second, cells are defined using a collar of 0.7 µm around the nuclei. The Cy5 fluorescence intensity inside the collar is measured (cell intensity) and results are reported on an "Average per cell" basis.

5. IC50 calculation: IC50s are calculated by plotting the cell intensity values on the y-axis with dose response values on the x-axis. IC50 values represent compound potency against mTOR.

Test 4: Autophagy Assay

Autophagy is a catabolic pathway that degrades bulk cytosol in lysosomal compartments enabling amino acids and fatty acids to be recycled. One of the key regulators of autophagy is the mammalian target of rapamycin (mTOR), a conserved serine/threonine kinase which suppresses the initiation of the autophagic process when nutrients, growth factors and energy are available. To quantify autophagy induction by mTOR inhibitors, we use a mCherry-GFP-LC3 reporter which is amenable to retroviral delivery into mammalian cells, stable expression and analysis by fluorescence microscopy.

mCherry-GFP-LC3 Reporter

The amino acid sequence of the mCherry-GFP-LC3 construct is shown below (SEQ ID NO: 5). The mCherry sequence is underlined, GFP sequence is in bold and LC3A sequence is boxed.

MVSKGEEDNMAIIKEFMRFKVHMEGSVNGHEFEIEGEGEGRPYEGTQTAK

LKVTKGGPLPFAWDILSPQFMYGSKAYVKHPADIPDYLKLSFPEGFKWER

VMNFEDGGVVTVTQDSSLQDGEFIYKVKLRGTNFPSDGPVMQKKTMGWEA

SSERMYPEDGALKGEIKQRLKLKDGGHYDAEVKTTYKAKKPVQLPGAYNV

NIKLDITSHNEDYTIVEQYERAEGRHSTGGMDELYKPVATMVSKGEELFT

GVVPILVELDGDVNGHKFSVSGEGEGDATYGKLTLKFICTTGKLPVPWPT

LVTTLTYGVQCFSRYPDHMKQHDFFKSAMPEGYVQERTIFFKDDGNYKTR

AEVKFEGDTLVNRIELKGIDFKEDGNILGHKLEYNYNSHNVYIMADKQKN

GIKVNFKIRHNIEDGSVQLADHYQQNTPIGDGPVLLPDNHYLSTQSALSK

DPNEKRDHMVLLEFVTAAGITLGMDELYKSGLRSRAQASNSAVD MPSDRP

FKQRRSFADRCKEVQQIRDQHPSKIPVIIERYKGEKQLPVLDKTKFLVPD

HVNMSELVKIIRRRLQLNPTQAFFLLVNQHSMVSVSTPIADIYEQEKDEL

GFLYMVYASQETFGF

Described hereinafter is an imaging protocol and image recognition algorithm to visualize and measure changes in the autophagic pathway.

Quantification of Autophagy Using High-Content Imaging and Analysis

1. Day 0: Cell plating. Subconfluent H4 mCherry-GFP-LC3 cells are harvested by trypsinization, resuspended in growth medium, and counted (H4 cells: Human neuroglioma cell line (ATCC)). A cell suspension of 66'000 cells/mL is prepared and 30 µL are added into the wells of a 384-well plate using an electronic multichannel pipette. This results in 2000 cells/well being plated. The cell plates are briefly spun down and placed at 37° C. and 5% $CO_2$.

2. Day 1: Compound treatment. Compound dose responses are prepared in DMSO. The dose responses are then diluted 1:50 in medium. 10 ul of the diluted compound is added to 30 ul of cells, yielding a final 1:200 dilution of the original compound and final of 0.5% DMSO. Compound-treatments are performed in triplicates. The 384-well plates are placed at 37° C. and 5% $CO_2$. Compound treatment is performed for 16-18 h (see Note 1).

3. Day 2: Cell fixation. Cells are fixed by adding 10 µL/well 5× concentrated Mirsky's fixative supplemented with 25 µg/mL Hoechst33342. This results in a total volume of 50 µL per well and a concentration of 1× Mirsky's fixative and 5 µg/mL Hoechst33342. The 384-well plate is briefly spun down and incubated for 1 h at room temperature. Cells are then washed using a 384-well plate washer using a protocol which aspirates the volume down to 10 µL/well before dispensing 100 µL/well 1×TBS. Aspiration and dispensing steps are repeated 4 times and a final volume of 100 µL/well is left. The plate is sealed using an adhesive PCR foil.

4. Imaging. The bottom of the plate is cleaned with 70% ethanol and then imaged using the InCell 1000 automated epifluorescence microscope. 20× magnification is used and 4 different areas (fields) are imaged per well, this typically captures a total of around 400 cells per well. Hoechst33342 images are acquired using an excitation of 360 nm (D360_40× filter), an emission of 460 nM (HQ460_40M filter) and an exposure time of 150 ms. GFP images are acquired using an excitation of 475 nm (S47520× filter), an emission of 535 nM (HQ535_50M filter) and an exposure time of 1 s. mCherry images are acquired using an excitation of 535 nm (HQ535_50× filter), an emission of 620 nM (HQ620_60M filter) and an exposure time of 1 s. A quadruple band pass mirror is used for all images.

5. Image analysis. The InCell Analysis software is used to analyze the images using the Multi Target Analysis algorithm. First, nuclei are detected in the Hoechst33342 image using top-hat segmentation and a minimal nuclear area of 50 μm². Cells are defined using a collar of 10 μm around the nuclei. Second, puncta (organelles) are identified in the mCherry image inside the cells using multi-top-hat segmentation. Third, the mask of the mCherry puncta is transferred onto the GFP image. Fourth, the GFP fluorescence intensity inside the mCherry puncta mask is measured (reference intensity).

6. The 'organelles' parameter reflects mCherry-positive puncta of the mCherry-GFP-LC3 reporter and is used to calculate 'LC3 puncta/cell'. For this purpose, the number of organelles is calculated per cell and averaged over all the cells in a given well (average per cell basis). mCherry-positive LC3 puncta numbers (y-axis) are plotted against the compound dose response values (x-axis) and EC50 values are calculated for each compound. EC50 values represent compound potency in terms of autophagy activation (e.g. increase in mCherry-positive LC3 puncta count).

Notes
1. Autophagy-modulation and redistribution of mCherry-GFP-LC3 can be already observed after a compound treatment time of 3-4 h. However, more robust effects are seen with 16-18 h treatment times.

The compounds of the Examples showed the values presented in Table 1 below when tested in the above assays.

TABLE 1

| Example Number | Test 1: PI3Kα $IC_{50}$ (nM) | Test 2: mTOR $IC_{50}$ (nM) | Test 3: TSC1−/− $IC_{50}$ (nM) | Test 4: Autophagy $EC_{50}$ (nM) |
|---|---|---|---|---|
| 1 | 20 | NT | 118 | NT |
| 2 | 1059 | 40 | 300 | 363 |
| 3 | 6530 | 510 | 2320 | >2000 |
| 4 | 1800 | 1424 | 1865 | 1551 |
| 5 | >9100 | 150 | 551 | 2594 |
| 6 | >9100 | 30 | 1452 | NT |
| 7 | 2540 | NT | 455 | NT |
| 8 | >9100 | 41 | 127 | 731 |
| 9 | >9100 | 3204 | 7300 | >10000 |
| 10 | 720 | 1836 | 5718 | >10000 |
| 11 | 8140 | 2425 | 6016 | >2000 |
| 12 | 2870 | 2023 | 1964 | >10000 |
| 13 | 430 | 469 | 2783 | 8529 |
| 14 | >9100 | 7 | 349 | 1284 |
| 15 | 4580 | 9 | 62 | 1781 |
| 16 | 7300 | 160 | 460 | 2000 |
| 17 | 400 | 399 | 1511 | 3193 |
| 18 | 5050 | 46 | 70 | 2500 |
| 19 | 170 | 134 | 300 | 2000 |
| 20 | 6050 | 6 | 90 | 452 |
| 21 | >9100 | 237 | 831 | 498 |
| 22 | 5860 | 5 | 113 | 761 |
| 23 | 5510 | 14 | 138 | 1610 |
| 24 | 8540 | 85 | 632 | NT |
| 25 | 2070 | 172 | 452 | >700 |
| 26 | 570 | 8 | 81 | 184 |
| 27 | 40 | 340 | 7186 | 5934 |
| 28 | 9050 | 372 | 458 | >200 |
| 29 | 3860 | 1208 | 2085 | >5000 |
| 30 | 3010 | 1447 | 1515 | >2000 |
| 31 | 590 | NT | 315 | NT |
| 32 | 2520 | 1044 | 1035 | NT |
| 33 | >9100 | 380 | 2987 | 7733 |
| 34 | >9100 | NT | 8002 | NT |
| 35 | 5870 | NT | 4006 | NT |
| 36 | 20 | NT | 73 | NT |
| 37 | 10 | NT | 620 | NT |
| 38 | 480 | NT | >50000 | NT |

NT = Not Tested

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by class I PI3K and/or mTOR or (ii) associated with class I PI3K and/or mTOR activity, or (iii) characterized by activity (normal or abnormal) of class I PI3K and/or mTOR; or (2) reducing or inhibiting the activity of class I PI3K and/or mTOR. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of class I PI3K and/or mTOR. The meaning of the term "a therapeutically effective amount" as illustrated in the above embodiments for class I PI3K and/or mTOR also applies by the same means to any other relevant proteins/peptides/enzymes, such as class II or III PI3K.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, the term "prevention" of any particular disease or disorder refers to the administration of a compound of the invention to a subject before any symptoms of that disease or disorder are apparent.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

The term "compounds of the present invention" (unless specifically identified otherwise) refer to compounds of formula (I), compounds of the Examples, pharmaceutically acceptable salts of such compounds, and/or hydrates or solvates of such compounds, as well as, all stereoisomers (including diastereoisomers and enantiomers), tautomers and isotopically labeled compounds (including deuterium).

Compounds of the present invention are useful for treating diseases, conditions and disorders modulated by the inhibition of class I PI3Ks and the mTOR enzyme; consequently, the compounds of the present invention (including the compositions and processes used therein) may be used in the manufacture of a medicament for the therapeutic applications described herein. Hence, another embodiment of the present invention is a pharmaceutical composition comprising a therapeutically effective amount of a compound of the present invention, or a pharmaceutically acceptable salt thereof, and a pharmaceutically acceptable excipient, diluent or carrier. In another embodiment of the present invention there is provided a pharmaceutical composition comprising a compound of the present invention, or a pharmaceutically acceptable salt thereof, and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

In one embodiment, the invention relates to the treatment of cellular proliferative diseases such as tumor and/or cancerous cell growth mediated by PI3K and/or mTOR. Diseases may include those showing overexpression or amplification of PI3K alpha, Rheb, somatic mutation of PIK3CA or germline mutations or somatic mutation of PTEN, TSC1, TSC2, or mutations and translocation of p85α that serve to up-regulate the p85-p110 complex. In particular, the compounds are useful in the treatment of human or animal (e.g., murine) cancers, including, for example, sarcoma; lung; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukaemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; melanoma; villous colon adenoma; a neoplasia; a neoplasia of epithelial character; lymphomas; a mammary carcinoma; basal cell carcinoma; squamous cell carcinoma; actinic keratosis; tumor diseases, including solid tumors; a tumor of the neck or head; polycythemia vera; essential thrombocythemia; myelofibrosis with myeloid metaplasia; and Walden stroem disease.

In other embodiments, the condition or disorder (e.g. PI3K-mediated) is selected from the group consisting of: polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

Additional syndromes with an established or potential molecular link to dysregulation of mTOR kinase activity are, for instance, described in "K. Inoki et al.; Disregulation of the TSC-mTOR pathway in human disease, Nature Genetics, vol 37, 19-24"; "D. M. Sabatini; mTOR and cancer: insights into a complex relationship, Nature Reviews, vol. 6, 729-734"; and in "B. T. Hennessy et al.; Exploiting the PI3K/Akt pathway for cancer drug discovery, Nature Reviews, vol. 4, 988-1004", and are as follows:

Organ or tissue transplant rejection, e.g. for the treatment of recipients of e.g. heart, lung, combined heart-lung, liver, kidney, pancreatic, skin or corneal transplants; graft-versus-host disease, such as following bone marrow transplantation;

Restenosis

Tuberous sclerosis

Lymphangioleiomyomatosis

Retinitis pigmentosis and other retinal degenerative disorders

Autoimmune diseases including encephalomyelitis, insulin-dependent diabetes mellitus, lupus, dermatomyositis, arthritis and rheumatic diseases Steroid-resistant acute Lymphoblastic Leukaemia Fibrotic diseases including scleroderma, pulmonary fibrosis, renal fibrosis, cystic fibrosis Pulmonary hypertension Immunomodulation Multiple sclerosis VHL syndrome Carney complex Familial adenonamtous polyposis Juvenile polyposis syndrome Birt-Hogg-Duke syndrome Familial hypertrophic cardiomyopathy Wolf-Parkinson-White syndrome Neurodegenerative disorders such as Parkinson's Disease, Huntington's Disease, Alzheimer's Disease and dementias caused by tau mutations, spinocerebellar ataxia type 3, motor neuron disease caused by SOD1 mutations, neuronal ceroid lipofucinoses/Batten disease (pediatric neurodegeneration)

wet and dry macular degeneration muscle wasting (atrophy, cachexia) and myopathies such as Danon's disease.

bacterial and viral infections including *M. tuberculosis*, group A *streptococcus*, HSV type I, HIV infection Neurofibromatosis including Neurofibromatosis type 1, and Peutz-Jeghers syndrome, Cowden's disease.

Compounds with an inhibitory activity on mTORC1 have shown benefit in immunomodulation and in treating proliferative diseases such as advance renal cell carcinoma or Tubero-Sclerosis (TSC) germ line mutation associated disorders.

The catalytic inhibition of mTOR Ser/Thr kinase activity or class I PI3 kinases activity and in particular dual class I PI3-kinase(s) and mTOR kinase inhibition may be useful for the treatment of PI3K/Akt/mTOR pathway dependent diseases. The efficacy of a dual PI3 kinase/mTOR inhibitor in malignant glioma has been recently described (Cancer Cell 9, 341-349).

For the above uses the required dosage will of course vary depending on the mode of administration, the particular condition to be treated and the effect desired. In general, satisfactory results are indicated to be obtained systemically at daily dosages of from about 0.03 to about 100.0 mg/kg per body weight, e.g. about 0.03 to about 10.0 mg/kg per body weight. An indicated daily dosage in the larger mammal, e.g. humans, is in the range from about 0.5 mg to about 3 g, e.g. about 5 mg to about 1.5 g, conveniently administered, for example, in divided doses up to four times a day or in retard form. Suitable unit dosage forms for oral administration comprise from ca. 0.1 to about 500 mg, e.g. about 1.0 to about 500 mg active ingredient.

In general, compounds of the present invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the present invention is inhalation. This is an effective method for delivering a therapeutic agent directly to the respiratory tract.

The compounds of the present invention may be administered in free form or in pharmaceutically acceptable salt form e.g. as indicated above. Such salts may be prepared in conventional manner and exhibit the same order of activity as the free compounds.

Consequently, the invention also provides:

a method for preventing or treating conditions, disorders or diseases mediated by the activation of the PI3K (e.g. PI3 kinase alpha) and/or mTOR enzymes e.g. such as indicated above, in a subject in need of such treatment, which method comprises administering to said subject an effective amount of a compound of the present invention or a pharmaceutically acceptable salt thereof. In one embodiment, there is provided a method for preventing or treating cancer or a neurodegenerative disorder, in a subject in need of such treatment, which method comprises administering to said subject an effective amount of a compound of the present invention or a pharmaceutically acceptable salt thereof. In another embodiment, the neurodegenerative disorder is Parkinson's, Huntington's or Alzheimer's Disease. In yet another embodiment, the neurodegenerative disorder is Huntington's Disease.

a compound of the present invention, or a pharmaceutically acceptable salt thereof, for use as a medicament, e.g. in any of the methods as indicated herein.

a compound of the present invention, or a pharmaceutically acceptable salt thereof, for use as pharmaceutical, e.g. in any of the methods as indicated herein, in particular for the use in one or more phosphatidylinositol 3-kinase mediated diseases. In one embodiment, there is provided a compound of the present invention, or a pharmaceutically acceptable salt thereof, for use in the treatment or prevention of cancer or a neurodegenerative disorder. In another embodiment, the neurodegenerative disorder is Parkinson's, Huntington's or Alzheimer's Disease. In yet another embodiment, the neurodegenerative disorder is Huntington's Disease.

the use of a compound of the present invention, or a pharmaceutically acceptable salt thereof, in any of the methods as indicated herein, in particular for the treatment or prevention of one or more phosphatidylinositol 3-kinase mediated diseases. In one embodiment, there is provided the use of a compound of the present invention, or a pharmaceutically acceptable salt thereof, for the treatment or prevention of cancer or a neurodegenerative disorder. In another embodiment, the neurodegenerative disorder is Parkinson's, Huntington's or Alzheimer's Disease. In yet another embodiment, the neurodegenerative disorder is Huntington's Disease.

the use of a compound of the present invention, or a pharmaceutically acceptable salt thereof, for the manufacture of a medicament for the treatment or prevention of one or more phosphatidylinositol 3-kinase mediated diseases. In one embodiment, there is provided the use of a compound of the present invention, or a pharmaceutically acceptable salt thereof, for the manufacture of a medicament for the treatment or prevention of cancer or a neurodegenerative disorder. In another embodiment, the neurodegenerative disorder is Parkinson's, Huntington's or Alzheimer's Disease. In yet another embodiment, the neurodegenerative disorder is Huntington's Disease.

PI3K serves as a second messenger node that integrates parallel signaling pathways, evidence is emerging that the combination of a PI3K inhibitor with inhibitors of other pathways will be useful in treating cancer and proliferative diseases in humans. Approximately 20-30% of human breast cancers overexpress Her-2/neu-ErbB2, the target for the drug trastuzumab. Although trastuzumab has demonstrated durable responses in some patients expressing Her2/neu-ErbB2, only a subset of these patients respond. Further studies have indicated that this limited response rate can be substantially improved by the combination of trastuzumab with inhibitors of PI3K or the PI3K/AKT pathway (Chan et al., Breast Can. Res. Treat. 91:187 (2005), Woods Ignatoski et al., Brit. J. Cancer 82:666 (2000), Nagata et al., Cancer Cell 6:117 (200)).

A variety of human malignancies express activating mutations or increased levels of Her1/EGFR and a number of antibody and small molecule inhibitors have been developed against this receptor tyrosine kinase including tarceva, gefitinib and erbitux. However, while EGFR inhibitors demonstrate anti-tumor activity in certain human tumors (e.g., NSCLC), they fail to increase overall patient survival in all patients with EGFR-expressing tumors. This may be rationalized by the fact that many downstream targets of Her1/EGFR are mutated or deregulated at high frequencies in a variety of malignancies, including the PI3K/Akt pathway. For example, gefitinib inhibits the growth of an adenocarcinoma cell line in in vitro assays. Nonetheless, sub-clones of these cell lines can be selected that are resistant to gefitinib that demonstrate increased activation of the PI3/Akt pathway. Down-regulation or inhibition of this pathway renders the resistant sub-clones sensitive to gefitinib (Kokubo et al., Brit. J. Cancer 92:1711 (2005)). Furthermore, in an in vitro model of breast cancer with a cell line that harbors a PTEN mutation and over-expresses EGFR inhibition of both the PI3K/Akt pathway and EGFR produced a synergistic effect (She et al., Cancer Cell 8:287-297 (2005)). These results indicate that the combination of gefitinib and PI3K/Akt pathway inhibitors would be an attractive therapeutic strategy in cancer.

The combination of AEE778 (an inhibitor of Her-2/neu/ErbB2, VEGFR and EGFR) and RAD001 (an inhibitor of mTOR, a downstream target of Akt) produced greater combined efficacy that either agent alone in a glioblastoma xenograft model (Goudar et al., Mol. Cancer. Ther. 4:101-112 (2005)).

Anti-estrogens, such as tamoxifen, inhibit breast cancer growth through induction of cell cycle arrest that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to anti-estrogen resistance (Donovan, et al, J. Biol. Chem. 276:40888, (2001)). As reported by Donovan et al., inhibition of MAPK signaling through treatment with MEK inhibitor reversed the aberrant phosphorylation status of p27 in hormone refractory breast cancer cell lines and in so doing restored hormone sensitivity. Similarly, phosphorylation of p27Kip by Akt also abrogates its role to arrest the cell cycle (Viglietto et al., Nat. Med. 8:1145 (2002)).

Accordingly, in a further aspect, the compounds of formula I may be useful in the treatment of hormone dependent cancers, such as breast and prostate cancers. By this use, it is aimed to reverse hormone resistance commonly seen in these cancers with conventional anticancer agents.

In hematological cancers, such as chronic myelogenous leukemia (CML), chromosomal translocation is responsible for the constitutively activated BCR-Abl tyrosine kinase. The afflicted patients are responsive to imatinib, a small molecule tyrosine kinase inhibitor, as a result of inhibition of Abl kinase activity. However, many patients with advanced stage disease respond to imatinib initially, but then relapse later due to resistance-conferring mutations in the Abl kinase domain. In vitro studies have demonstrated that BCR-Ab1 employs the Ras-Raf kinase pathway to elicit its effects. In addition, inhibiting more than one kinase in the same pathway provides additional protection against resistance-conferring mutations.

Accordingly, in another aspect, the compounds of the present invention are used in combination with at least one additional agent selected from the group of kinase inhibitors, such as Gleevec®, in the treatment of hematological cancers, such as chronic myelogenous leukemia (CML). By this use, it is aimed to reverse or prevent resistance to said at least one additional agent.

Because activation of the PI3K/Akt pathway drives cell survival, inhibition of the pathway in combination with therapies that drive apoptosis in cancer cells, including radiotherapy and chemotherapy, will result in improved responses (Ghobrial et al., CA Cancer J. Clin 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, Mol. Cancer. Ther. 4:1764-1771 (2005)).

In addition to cancer and proliferative diseases, there is accumulating evidence that inhibitors of Class 1A and 1B PI3 kinases would be therapeutically useful in others disease areas. The inhibition of p110β, the PI3K isoform product of the PIK3CB gene, has been shown to be involved in shear-induced platelet activation (Jackson et al., Nature Medicine 11:507-514 (2005)). Thus, a PI3K inhibitor that inhibits p110β would be useful as a single agent or in combination in anti-thrombotic therapy. The isoform p110δ, the product of the PIK3CD gene, is important in B cell function and differentiation (Clayton et al., J. Exp. Med. 196:753-763 (2002)), T-cell dependent and independent antigen responses (Jou et al., Mol. Cell. Biol. 22:8580-8590 (2002)) and mast cell differentiation (Ali et al., Nature 431:1007-1011 (2004)). Thus, it is expected that p110δ-inhibitors would be useful in the treatment of B-cell driven autoimmune diseases and asthma. Finally, the inhibition of p110γ, the isoform product of the PI3KCG gene, results in reduced T, but not B cell, response (Reif et al., J. Immunol. 173:2236-2240 (2004)) and its inhibition demonstrates efficacy in animal models of autoimmune diseases (Camps et al., Nature Medicine 11:936-943 (2005), Barber et al., Nature Medicine 11:933-935 (2005)).

The invention further provides pharmaceutical compositions comprising at least one compound of the present invention, together with a pharmaceutically acceptable excipient suitable for administration to a human or animal subject, either alone or together with other anticancer agents.

The invention further provides methods of treating human or animal subjects suffering from a cellular proliferative disease, such as cancer. The invention thus provides methods of treating a human or animal subject in need of such treatment, comprising administering to the subject a therapeutically effective amount of a compound of the present invention either alone or in combination with one or more other anticancer agents. In particular, compositions will either be formulated together as a combination therapeutic or administered separately. Suitable anticancer agents for use with a compound of the present invention include, but are not limited to, one or more compounds selected from the group consisting of kinase inhibitors, anti-estrogens, anti androgens, other inhibitors, cancer chemotherapeutic drugs, alkylating agents, chelating agents, biological response modifiers, cancer vaccines, agents for antisense therapy as set forth below:

A. Kinase Inhibitors:

Kinase inhibitors for use as anticancer agents in conjunction with the compound of the present invention include inhibitors of Epidermal Growth Factor Receptor (EGFR) kinases such as small molecule quinazolines, for example gefitinib (U.S. Pat. No. 5,457,105, U.S. Pat. No. 5,616,582, and U.S. Pat. No. 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. No. 6,605,617 and U.S. Pat. No. 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621, 100), Cand5 (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as CHIR-258, 3G3 mAb, AG-13736, SU-11248 and SU6668; and Bcr-Abl kinase inhibitors and fusion proteins such as STI-571 or Gleevec® (imatinib).

B. Anti-Estrogens:

Estrogen-targeting agents for use in anticancer therapy in conjunction with the compound of the present invention include Selective Estrogen Receptor Modulators (SERMs) including tamoxifen, toremifene, raloxifene; aromatase inhibitors including Arimidex® or anastrozole; Estrogen Receptor Downregulators (ERDs) including Faslodex® or fulvestrant.

C. Anti-Androgens:

Androgen-targeting agents for use in anticancer therapy in conjunction with the compound of the present invention include flutamide, bicalutamide, finasteride, aminoglutethamide, ketoconazole, and corticosteroids.

D. Other Inhibitors:

Other inhibitors for use as anticancer agents in conjunction with the compound of the present invention include protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade® (U.S. Pat. No. 5,780,454), XL-784; and cyclooxygenase 2 (COX-2) inhibitors including non-steroidal antiinflammatory drugs I (NSAIDs).

E. Cancer Chemotherapeutic Drugs:

Particular cancer chemotherapeutic agents for use as anticancer agents in conjunction with the compound of the present invention include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxon), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

F. Alkylating Agents:

Alkylating agents for use in conjunction with the compound of the present invention include VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); 06-benzylguanine; decitabine (5-aza-2-deoxycytidine); brostallicin; mitomycin C (MitoExtra); TLK-286 (Telcyta®); temozolomide; trabectedin (U.S. Pat. No. 5,478, 932); AP-5280 (Platinate formulation of Cisplatin); porfiromycin; and clearazide (meclorethamine).

G. Chelating Agents:

Chelating agents for use in conjunction with the compound of the present invention include tetrathiomolybdate (WO 01/60814); RP-697; Chimeric T84.66 (cT84.66); gadofosveset (Vasovist®); deferoxamine; and bleomycin optionally in combination with electorporation (EPT).

H. Biological Response Modifiers:

Biological response modifiers, such as immune modulators, for use in conjunction with the compound of the present invention include staurosprine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexylen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266, 575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

I. Cancer Vaccines:

Anticancer vaccines for use in conjunction with the compound of the present invention include Avicine® (Tetrahedron Lett. 26:2269-70 (1974)); oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

J. Antisense Therapy:

Anticancer agents for use in conjunction with the compound of the present invention also include antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sirna-027 (RNAi-based therapeutic targeting VEGFR-1 mRNA).

The compound of the present invention may also be combined in a pharmaceutical composition with bronchiodilatory or antihistamine drugs substances. Such bronchiodilatory drugs include anticholinergic or antimuscarinic agents, in particular ipratropium bromide, oxitropium bromide, and tiotropium bromide, and β-2-adrenoreceptor agonists such as salbutamol, terbutaline, salmeterol, carmoterol, milveterol and, especially, formoterol or indacaterol. Co-therapeutic antihistamine drug substances include cetirizine hydrochloride, clemastine fumarate, promethazine, loratadine, desloratadine diphenhydramine and fexofenadine hydrochloride.

The invention provides in a further aspect a combination comprising a compound of the present invention and one or more compounds that are useful for the treatment of a thrombolytic disease, heart disease, stroke, etc. Such compounds include aspirin, a streptokinase, a tissue plasminogen activator, a urokinase, a anticoagulant, antiplatelet drugs (e.g, PLAVIX; clopidogrel bisulfate), a statin (e.g., LIPITOR or Atorvastatin calcium), ZOCOR (Simvastatin), CRESTOR (Rosuvastatin), etc.), a Beta blocker (e.g., Atenolol), NORVASC (amlodipine besylate), and an ACE inhibitor (e.g., lisinopril).

The invention provides in a further aspect a combination comprising a compound of the present invention and one or more compounds that are useful for the treatment of antihypertension. Such compounds include ACE inhibitors, lipid lowering agents such as statins, LIPITOR (Atorvastatin calcium), calcium channel blockers such as NORVASC (amlodipine besylate).

The invention provides in a further aspect a combination comprising a compound of the present invention and one or more compounds selected from the group consisting of fibrates, beta-blockers, NEPI inhibitors, Angiotensin-2 receptor antagonists and platelet aggregation inhibitors.

The invention provides in a further aspect a combination comprising a compound of the present invention and a compound suitable for the treatment of inflammatory diseases, including rheumatoid arthritis. Such compound may be selected from the group consisting of TNF-α inhibitors such as anti-TNF-α monoclonal antibodies (such as REMICADE, CDP-870) and D2E7 (HUMIRA) and TNF receptor immunoglobulin fusion molecules (such as ENBREL), IL-1 inhibitors, receptor antagonists or soluble IL-1Rα (e.g. KINERET or ICE inhibitors), nonsterodial anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX (celecoxib), PREXIGE (lumiracoxib)), metalloprotease inhibitors (preferably MMP-13 selective inhibitors), p2×7 inhibitors, α2αinhibitors, NEUROTIN, pregabalin, low dose methotrexate, leflunomide, hydroxyxchloroquine, d-penicillamine, auranofin or parenteral or oral gold.

The invention provides in a further aspect a combination comprising a compound of the present invention and a compound suitable for the treatment of osteoarthritis. Such compound may be selected from the group consisting of standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, lumiracoxib and etoricoxib, analgesics and intraarticular therapies such as corticosteroids and hyaluronic acids such as hyalgan and synvisc.

The invention provides in a further aspect a combination comprising a compound of the present invention and an antiviral agent and/or an antisepsis compound. Such antiviral agent may be selected from the group consisting of Viracept, AZT, acyclovir and famciclovir. Such antisepsis compound may be selected from the group consisting of Valant.

The invention provides in a further aspect a combination comprising a compound of the present invention and one or more agents selected from the group consisting of CNS agents such as antidepressants (sertraline), anti-Parkinsonian drugs (such as deprenyl, L-dopa, Requip, Mirapex; MAOB inhibitors (such as selegine and rasagiline); comP inhibitors (such as Tasmar); A-2 inhibitors; dopamine reuptake inhibitors; NMDA antagonists; Nicotine agonists; Dopamine agonists; and inhibitors of neuronal nitric oxide synthase).

The invention provides in a further aspect a combination comprising a compound of the present invention and one or more anti-Alzheimer's drugs. Such anti-Alzheimer Drug may be selected from the group consisting of donepezil, tacrine, α2δinhibitors, NEUROTIN, pregabalin, COX-2 inhibitors, propentofylline or metrifonate.

The invention provides in a further aspect a combination comprising a compound of the present invention and anosteoporosis agents and/or an immunosuppressant agent. Such osteoporosis agents may be selected from the group consisting of EVISTA (raloxifene hydrochloride), droloxifene, lasofoxifene or fosomax. Such immunosuppressant agents may be selected from the group consisting of FK-506 and rapamycin.

In another aspect of the preferred embodiments, kits that include one or more compound of the present invention and a combination partner as disclosed herein are provided. Representative kits include a PI3K inhibitor compound (e.g., a compound of the present invention) and a package insert or other labeling including directions for treating a cellular proliferative disease by administering a PI3K inhibitory amount of the compound(s).

Combined pharmaceutical compositions comprising a compound of the present invention in free form or in pharmaceutically acceptable salt form and further comprising a combination partner (either in one dosage unit form or as a kit of parts) in association with at least one pharmaceutical acceptable carrier and/or diluent may be manufactured in conventional manner by mixing with a pharmaceutically acceptable carrier and/or diluent with said active ingredients.

Consequently, the invention provides in further aspects

- a combination, e.g. for use in any of the methods described herein, comprising a therapeutically effective amount of a compound of the present invention, or a pharmaceutically acceptable salt thereof, and another therapeutic agent, for simultaneous or sequential administration.
- a product comprising a compound of the present invention, or a pharmaceutically acceptable salt thereof, and another therapeutic agent.
- a product comprising a compound of the present invention, or a pharmaceutically acceptable salt thereof, and another therapeutic agent as a combined preparation for use in therapy, e.g. for use in any of the therapies described herein. In one embodiment, the therapy is the treatment or prevention of cancer or a neurodegenerative disorder. In another embodiment, the therapy is the treatment or prevention of Parkinson's, Huntington's or Alzheimer's Disease. In yet another embodiment, the therapy is the treatment or prevention of Huntington's Disease.
- a combined pharmaceutical composition comprising a compound of the present invention, or a pharmaceutically acceptable salt thereof, and another therapeutic agent.
- a combined pharmaceutical composition comprising a compound of the present invention, or a pharmaceutically acceptable salt thereof, another therapeutic agent and optionally one or more pharmaceutically acceptable carrier material(s) and/or diluents. Such combined pharmaceutical composition may be in the form of one dosage unit form or as a kit of parts.
- a method as defined above comprising co-administration, e.g. concomitantly or in sequence, of a therapeutically effective amount of a compound of the present invention, or a pharmaceutically acceptable salt thereof, and another therapeutic agent, e.g. as indicated above.
- a pharmaceutical combination, e.g. a kit, comprising a) a first agent which is a compound of the present invention as disclosed herein, or a pharmaceutically acceptable salt thereof, and b) another therapeutic agent, e.g. as indicated above; whereby such kit may comprise instructions for its administration.

The following examples of compounds of the present invention illustrate the invention without limiting the scope thereof. Methods for preparing such compounds are described hereinafter.

EXAMPLES

Abbreviations
Ac/ac/Oac acetyl CH3CO—
AcOEt/EA/EtOAc ethyl acetate
AcOH acetic acid
ACN/MeCN/CH$_3$CN acetonitrile
Biotage flash Chromatography
brs broad singlet
CDCl$_3$ deuterated chloroform
CsF cesium fluoride
Cu(OAc) copper(I) acetate
d doublet
Da dalton
DAD-UV ultra violet diode array detection/ultra violet diode array detector
DCM/CH$_2$Cl$_2$ dichloromethane
deg degree
dt doublet triplet
DIPEA di-isopropylethyl amine
DMA dimethylacetamide
DMF dimethylformide
DMSO dimethylsulfoxide
DMSO-d$_6$ deuterated dimethylsulfoxide
dppf 1,1'-Bis(diphenylphosphino)ferrocene
e.g. for example
equiv equivalent
Et$_2$O ethyl ether
EtOH ethanol
Gilston/Prep-LC HPLC—(high performance) liquid chromatography
/Preparative HPLC
HPLC/LC high performance liquid chromatography/liquid chromatography
hr/hrs hours
i-PrOH iso-propanol
KOAc potassium acetate
L liter
LC liquid chromatography
LC-MS liquid chromatography-mass spectrometry LC-UV liquid chromatography—with Ultra Violet detection
MeOH methanol
CD$_3$OD deuterated methanol
m multitet
MS mass spectrometry
NMP N-Methyl-2-pyrrolidone/methylpyrrolidone
NMR nuclear magnetic resonance
$^1$HNMR proton nuclear magnetic resonance
Pd(OAc)$_2$ palladium(II) acetate
PdCl$_2$(PPh$_3$)$_2$ bis(triphenylphosphine) palladium(II) chloride
PdCl$_2$(dppf) 1,1'-Bis(diphenylphosphino)ferrocene palladium (II) chloride
PPh$_3$ triphenyl phosphine
RT/rt room temperature
singlet
t triplet
TFA trifluoroacetic acid
THF tetrahydrofuran
TLC thin-layer chromatography
UV ultraviolet
uW/MW microwave heating source
wt % weight percent
Analytical Methods
NMR:

proton spectra are recorded on a Bruker 400 MHz ultrashield spectrometer unless otherwise noted. Chemical shifts are reported in ppm relative to methanol (δ3.31), dimethyl sulfoxide (δ2.50), or chloroform (δ7.26). A small amount of the dry sample (2-5 mg) is dissolved in an appropriate deuterated solvent (1 mL). The shimming is automated and the spectra is obtained with 64 or more scans.

LC/MS:

The sample is dissolved in suitable solvent such as MeCN, DMSO or MeOH and is injected directly into the column using the automated sample handler. The analysis is done using with one of the following methods:

Method 1: compounds are analyzed on an Inertsil ODS-3 column (C18, 50×4.6 mm, 3 µm) with a 2 min gradient elution (20-80% acetonitrile/H$_2$O/5 mM ammonium formate) and a flow rate of 4 mL/min.

Method 2: GENERAL LC/MS method with acid mobile phase (0.1% formic acid) and fast gradient. Electrospray mass spectra (+) and (−), DAD-UV chromatogram 200-400 nm, scan range 120-1500 Da. Gradient: 20-80% MeCN/H$_2$O in 2 min (2 mL/min), 2 µL injection. Column: Inertsil ODS3 C-18, 3 cm×33 mm×3.0 µm, 40 deg C.

Method 3: GENERAL LC/MS method with neutral mobile phase (5 mM NH$_4$$^+$HCOO$^-$) and fast (20-80%) gradient. Electrospray mass spectra (+) and (−), DAD-UV chromatogram 200-400 nm, scan range 120-1500 Da. Gradient: 20-80% MeCN/H$_2$O in 2 min (2 mL/min), 2 µL injection. Column: Inertsil ODS3 C-18, 3 cm×33 mm×3.0 µm, 40 deg C.

Method 4: LC/MS method for NON-POLAR (greasy) compounds with acid mobile phase (0.1% formic acid) and fast (40-90%) gradient. Electrospray mass spectra (+) and (−), DAD-UV chromatogram 200-400 nm, scan range 120-1500 Da. Gradient: 40-90% MeCN/H$_2$O in 2 min (2 mL/min), 2 µL injection. Column: Inertsil C8-3, 3 cm×33 mm×3.0 µm, 40 deg C.

Method 5: LC/MS method for NON-POLAR (greasy) compounds with neutral mobile phase (5 mM NH$_4$$^+$HCOO$^-$) and fast (40-90%) gradient. Electrospray mass spectra (+) and (−), DAD-UV chromatogram 200-400 nm, scan range 120-1500 Da. Gradient: 40-90% MeCN/H$_2$O in 2 min (2 mL/min), 2 µL injection. Column: Inertsil C8-3, 3.0 cm×33 mm×3.0 µm, 40 deg C.

Method 6: LC/MS method with broad range (5-95%) gradient with acid mobile phase (0.1% Formic Acid). Electrospray mass spectra (+) and (−), DAD-UV chromatogram 200-400 nm, scan range 120-1500 Da. Gradient: 5-95% MeCN/H$_2$O in 2 min (2 mL/min), 2 µL injection. Column: Inertsil C8-3, 3.0 cm×33 mm×3.0 µm, 40 deg C.

Method 7: LC/MS method with broad range (5-95%) gradient with neutral mobile phase (5 mM NH$_4$$^+$HCOO$^-$). Electrospray mass spectra (+) and (−), DAD-UV chromatogram 200-400 nm, scan range 120-1500 Da. Gradient: 5-95% MeCN/H$_2$O in 2 min (2 mL/min), 2 µL injection. Column: Inertsil C8-3, 3 cm×33 mm×3.0 µm, 40 deg C.

Method 8: LC/MS method for POLAR compounds with acid mobile phase (0.1% formic acid) and slow (0-100%) gradient. Electrospray mass spectra (+) and (−), DAD-UV chromatogram 200-400 nm, scan range 120-1500 Da. Gradient: 0-100% MeCN/H$_2$O in 2 min (2 mL/min), 2 µL injection. Column: Inertsil ODS3 (C-18, 3 cm×33 mm×3.0 µm, 40 degree C.)

Method 9: LC/MS method for POLAR compounds with neutral mobile phase (5 mM NH$_4$$^+$HCOO$^-$) and slow (0-100%) gradient. Electrospray mass spectra (+) and (−), DAD-UV chromatogram 200-400 nm, scan range 120-1500 Da. Gradient: 0-100% MeCN/H$_2$O in 2 min (2 mL/min), 2 µL injection. Column: Inertsil ODS-3 (C-18, 3 cm×33 mm×3.0 µm, 40 deg C.

Method 10: Compounds are analyzed on an Inertsil ODS-3 column (C8, 30 mm×3.0 mm, 3.0 um) with a 2 min gradient elution (5-90% acetonitrile/H$_2$O/5 mM ammonium formate) and a flow rate of 2 mL/min.

Method 11: Compounds are analyzed on an Inertsil ODS-3 column (C8, 30 mm×3.0 mm, 3.0 um) with a 2 min gradient elution (5-90% acetonitrile/H$_2$O/0.1% formic acid) and a flow rate of 2 mL/min.

HPLC purification utilizes a C8 or C18 column (30×100 mm, 5 um, brand: Sunfire or XTerra). The sample is dissolved in suitable solvent such as MeCN, DMSO or MeOH (maximum 5 mL) and is injected directly into the column using the automated sample handler. The purification is performed with an appropriate gradient using two methods (unless otherwise noted). Method 1 consists of 0.1% TFA in 5%-95% ACN in H$_2$O. Method 2 consists of 10 mM NH$_4$OH in 5%-95% ACN in H$_2$O.

Synthesis of Boronic Ester Intermediates

The boronic ester intermediates used in the preparation of compounds of the present invention are either commercially available or may be prepared as described in the literature, or in an analogous manner, or can be prepared as described hereafter, or in an analogous manner.

Boronic ester 1

4-(4,4,5,5-Tetramethyl-[1,3,2]dioxaborolan-2-yl)-1H-pyrrolo[2,3-b]pyridine

To a solution of 4-Bromo-7-azaindole (0.48 g, 2.41 mmol) in dioxane (12 mL) was added bis(pinacolato)diboron followed by bis(diphenylphosphino)ferrocene (0.067 g, 0.12 mmol). The mixture was degassed for 20 minutes using nitrogen, followed by addition of PdCl$_2$(dppf) catalyst (0.088 g, 0.12 mmol). Suspension was degassed for additional 5 minutes. Vial was seal and placed in an oil bath. The reaction was heated to 120° C. for 16 hours. After completion, the reaction mixture was allowed to cool to ambient temperature, suspension was filtered and solvent was removed under reduced pressure. The crude was directly purified on Biotage using 0-100% gradient of EtOAC/Heptane. Further purification was done using preparative HPLC (gradient 5%-95% with 3% n-propanol/acetonitrile over 3% n-propanol/water) to afford as a white solid (0.054 g, 9.2%) LC/MS analysis using method 7, mass (ES+) m/z 245.4 $^1$H NMR (CDCl$_3$) δ 9.03 (1H, brs), 8.24 (1H, d), 7.42 (1H, d), 7.30 (1H, d), 6.86 (1H, d), 1.31 (12H, s)

Boronic ester 2

[2-Methoxy-5-(4,4,5,5-tetramethyl-[1,3,2]dioxaborolan-2-yl)-phenyl]-methanol

Boronic ester was synthesized using general procedure described in Scheme 3. The compound was isolated in 77% yield as yellow oil. $^1$H NMR (CD$_3$OD): δ 7.76 (1H, s), 7.67 (1H, d), 6.90 (1H, d), 4.62 (2H, s), 3.83 (3H, s), 1.32 (12H, s)

Boronic ester 3

[3-Methoxy-5-(4,4,5,5-tetramethyl-[1,3,2]dioxaborolan-2-yl)-phenyl]-methanol

Boronic ester was synthesized using general procedure described in Scheme 3. The compound was isolated in 27% yield as brown solid. $^1$HNMR (DMSO-d$_6$): δ 7.24 (1H, s), 7.01 (1H, s), 6.99 (1H, s), 5.18 (1H, m), 4.47 (2H, d), 3.75 (3H, s), 1.29 (12H, s).

Boronic ester 4

BOC-3-(4,4,5,5-Tetramethyl-[1,3,2]dioxaborolan-2-yl)-benzylamine

To a solution of 3-bromobenzylamine (0.79 g, 4.24 mmol), di-tertbutyldicarbonate (1.82 g, 8.5 mmol, 2.0 equiv) in 10 mL of CH$_2$Cl$_2$ was added triethylamine (1.29 g, 12.7 mmol, 3.0 equiv.) After 2 hours of stirring the reaction was stopped and the solution was washed with water. Aqueous layer was extracted with CH$_2$Cl$_2$. Organic layers combined and dried over MgSO$_4$. Upon removal of solvent under reduced pressure, the crude was purified using flash column chromatography (Biotage, 0-60% gradient of EtOAc/Heptane). The desired boronic ester was then synthesized using general coupling procedure described in Scheme 3. The compound was isolated in 59% yield as brown solid. $^1$HNMR (CDCl$_3$): δ 7.61-7.62 (2H, m), 7.27-7.31 (1H, m), 7.24 (1H, t), 4.85 (1H, brs), 4.72 (2H, brs), 1.37 (9H, s), 1.25 (12H, s)

Example 1

Synthesis of 3-[2-((2S,6R)-2,6-Dimethyl-morpholin-4-yl)-6-morpholin-4-yl-9H-purin-8-yl]-phenol

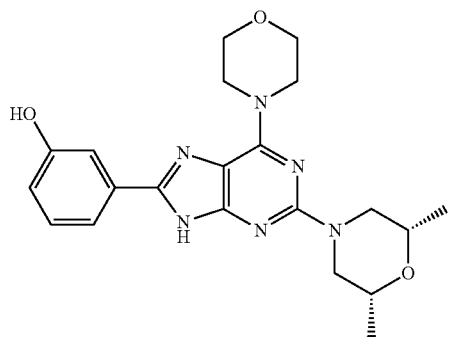 [SMILES: C[C@@H]1CN(c2nc(N3CCOCC3)c3nc(-c4cccc(O)c4)[nH]c3n2)C[C@H](C)O1]

a) 2-Chloro-6-morpholin-4-yl-9H-purine

To a solution of 2,6-dichloro-9H-purine (1.2 g, 6.35 mmol) in N,N-dimethylformamide (5 mL) was added morpholine (553 mg, 6.35 mmol) followed by diisopropylethyl amine (1.2 mL, 6.87 mmol), dropwise via a syringe. The solution was stirred at room temperature for 1 hour until precipitate formed. The reaction mixture was then poured into water and the precipitate was filtered. Upon drying under high vacuum, 2-chloro-6-morpholin-4-yl-9H-purine was isolated as an off-white solid. (1.5 g, 99%) LC/MS analysis method 7, mass (ES+) m/z 240.2 $^1$H NMR (DMSO-d$_6$): 13.21 (1H, brs), 8.15 (1H, s), 4.18 (4H, brs), 3.72 (4H, t)

b) 2-((2S,6R)-2,6-Dimethyl-morpholin-4-yl)-6-morpholin-4-yl-9H-purine

To the solution of 2-chloro-6-morpholin-4-yl-9H-purine (1.5 g, 6.26 mmol) in DMA (5 mL) was added cis-2,6 dimethylmorpholine (1.42 g, 12.52 mmol), followed by DIPEA (2.1 mL, 12.02 mmol). The mixture was stirred at 130° C. for 40 hours. Upon completion of the reaction, the solution was poured into water. The aqueous layer was extracted with EtOAc three times. The combined organic layers were dried over Na$_2$SO$_4$, filtered and the solvent was removed under reduced pressure to provide 2-((2S,6R)-2,6-dimethyl-morpholin-4-yl)-6-morpholin-4-yl-9H-purine (1.96 g, 98%) as a yellow solid. LC/MS analysis method 7, mass (ES+) m/z 319.2 $^1$HNMR (DMSO-d$_6$): 12.37 (1H, s), 7.76 (1H, s), 4.38 (2H, d), 4.12 (4H, brs), 3.69 (4H, m), 3.54 (2H, m), 2.40 (2H, m), 1.14 (6H, d).

c) 8-Bromo-2-((2S,6R)-2,6-dimethyl-morpholin-4-yl)-6-morpholin-4-yl-9H-purine

To a solution of 2-((2S,6R)-2,6-dimethyl-morpholin-4-yl)-6-morpholin-4-yl-9H-purine (860 mg, 2.70 mmol) in CH$_2$Cl$_2$ (5 mL) was added bromine (0.04 mL, 3.24 mmol). The mixture was stirred at ambient temperature for 3 hours. Saturated sodium thiosulfate was added. The aqueous layer was extracted with dichloromethane two times. Organic layers were combined and dried over Na$_2$SO$_4$ and solvent was removed under reduced pressure. The crude was purified by flash column chromatography (0-70% EtOAc/Heptane gradient) to furnish product as an off-white solid (362.1 mg, 34%). LC/MS analysis using method 7, mass (ES+) m/z 399.1 $^1$HNMR (CDCl$_3$): 4.31 (2H, d), 4.09 (4H, brs), 3.74 (4H, m), 3.59 (2H, m), 2.51 (2H, m), 1.18 (6H, d).

d) 3-[2-((2S,6R)-2,6-Dimethyl-morpholin-4-yl)-6-morpholin-4-yl-9H-purin-8-yl]-phenol To a round bottom flask were added, 8-bromo-2-((2S,6R)-2,6-dimethyl-morpholin-4-yl)-6-morpholin-4-yl-9H-purine (38.2 mg, 0.096 mmol), cesium fluoride 58.4 mg, 0.39 mmol), 3-hydroxyphenylboronic acid (39.8 mg, 0.29 mmol) and tetrakis(triphenylphosphine)palladium (8.9 mg, 7.69 mmol) followed by 1 mL of acetonitrile/water solvent mixture (10/1 ratio). Suspension was heated to 115° C. and stirred overnight. Upon completion of the reaction, the suspension was cooled and solids filtered off. Solvent was removed under reduced pressure and the crude was purified directly by preparative HPLC to provide 3-[2-((2S,6R)-2,6-dimethyl-morpholin-4-yl)-6-morpholin-4-yl-9H-purin-8-yl]-phenol (18.5 mg, 47%) as yellow solid. LC/MS analysis method 7, mass (ES+) m/z 411.2, retention time 1.40 min. $^1$HNMR (CDCl$_3$): 7.34 (1H, d), 7.24 (2H, m), 6.87 (1H, d), 4.35 (2H, d), 4.30 (4H, brs), 3.80 (4H, m), 3.57 (2H, m), 2.53 (2H, t), 1.16 (6H, d).

Example 2

3-(2,4-Di-morpholin-4-yl-7H-pyrrolo[2,3-d]pyrimidin-6-yl)-phenol

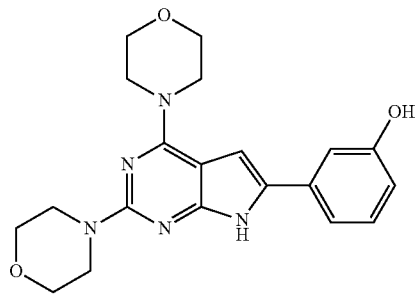 [SMILES: Oc1cccc(-c2cc3c(N4CCOCC4)nc(N4CCOCC4)nc3[nH]2)c1]

a) 2,4-Di-morpholin-4-yl-7H-pyrrolo[2,3-d]pyrimidine

In a 20 mL vial, 2,4-dichloro-7H-pyrrolo[2,3-d]pyrimidine (0.19 g, 1.011 mmol, 1.0 equiv) was dissolved in NMP (2 mL). Di-isopropyl-ethylamine (0.392 g, 0.514 mL, 3.03 mmol, 3.0 equiv) and morpholine (0.264 g, 0.264 mL, 3.03 mmol, 3.0 equiv.) were then added. The reaction mixture was then transferred into a 5 mL microwave vessel and heated at 200° C. for 30 minutes. The reaction was then cooled down to room temperature and diluted with 35 mL of ethyl acetate. The organic phase was then washed with saturated ammonium chloride solution (2×30 mL). The organic layer was then dried with MgSO$_4$, filtered and removed under reduced pressure to obtain a brown oil. The oil was then purified using flash chromatography using 20% to 100% gradient of EtOAc/Heptane. The compound was isolated as a white solid (239.1 mg, 82% yield). $^1$HNMR (CDCl$_3$): δ 9.67 (1H, brs), 6.74 (1H, m), 6.29 (1H, d), 3.82 (8H, dt), 3.72 (8H, m)

b) 4-Di-morpholin-4-yl-7-(2-trimethylsilanyl-ethoxymethyl)-7H-pyrrolo[2,3-d]pyrimidine A solution of 2,4-di-morpholin-4-yl-7H-pyrrolo[2,3-d]pyrimidine (180 mg, 0.622 mmol, 1.0 equiv) in 25 mL of DMF was cooled to 0° C. using an ice bath under nitrogen atmosphere. Sodium hydride in oil was then added (60 wt %, 34.8 mg, 0.871 mmol, 1.4 equiv) and the reaction was stirred for 1 hr at 0° C. To the reaction mixture, 2-(chloromethoxy)ethyl) trimethylsilane (154 μL, 145 mg, 0.871 mmol, 1.4 equiv) was added and the reaction was allowed to warm up to room temperature overnight. The reaction was quenched by adding 5 mL of H$_2$O then poured into 30 mL of EtOAc. The organic phase was then washed twice with aqueous saturated ammonium chloride solution (2×25 mL). The organic layer was then dried with MgSO$_4$, filtered and removed under reduced pressure to obtain dark brown colored oil. The oil was purified by flash chromatography using 0% to 70% EtOAc/Heptane gradient. The product was isolated as a white solid (205 mg, 79% yield). $^1$HNMR (CDCl$_3$): δ 6.91 (1H, d), 6.46 (1H, d), 5.55 (2H, s), 3.94 (8H, dt), 3.82 (8H, brs), 3.57 (2H, t), 0.95 (2H, t), 0.00 (9H, s)

c) 3-[2,4-Di-morpholin-4-yl-7-(2-trimethylsilanyl-ethoxymethyl)-7H-pyrrolo[2,3-d]pyrimidin-6-yl]-phenol To a 20 mL vial with a septum were added, 4-di-morpholin-4-yl-7-(2-trimethylsilanyl-ethoxymethyl)-7H-pyrrolo[2,3-d]pyrimidine (40 mg, 0.095 mmol, 1 equiv), palladium (II) acetate (2.15 mg, 0.0095 mmol, 0.1 equiv), copper (II) acetate (3.5 mg, 0.019 mmol, 0.2 equiv) and 3-hydroxyphenyl boronic acid (26.3 mg, 0.191 mmol, 2 equiv) followed by acetic acid (5 mL). The reaction was then stirred under 1 atm of air for 15 hours at room temperature. The reaction was cooled to 0° C. and aqueous saturated sodium bicarbonate solution was added slowly to quench the acid. The reaction was then diluted with ethyl acetate (40 mL) and washed with aqueous saturated bicarbonate solution (2×20 mL). The organic layer was then removed under reduced pressure. The crude product was directly purified using reverse phase preparative HPLC system (5% to 100% H$_2$O/MeCN gradient with 0.1% TFA in water as modifier). Upon lypholizing the fractions containing the desired product, a total of 34.6 mg of C2 and C3 arylation product was obtained. The earlier fraction contained the desired C2 arylation product (8.1 mg, 16.9% yield). $^1$HNMR (CDCl$_3$): δ 7.24 (1H, brs), 7.21 (1H, brs), 6.82 (1H, d), 6.44 (1H, s), 5.50 (2H, s), 3.87 (4H, m), 3.83 (4H, m), 3.79 (11H, m), 0.98 (2H, t), 0.00 (9H, s)

d) 3-(2,4-Di-morpholin-4-yl-7H-pyrrolo[2,3-d]pyrimidin-6-yl)-phenol

To a round bottom flask were added 3-[2,4-di-morpholin-4-yl-7-(2-trimethylsilanyl-ethoxymethyl)-7H-pyrrolo[2,3-d]pyrimidin-6-yl]-phenol (8.1 mg, 0.016 mmol) and cesium fluoride (72.4 mg, 0.477 mmol, 30 equiv) followed by acetone (6 mL). The reaction was heated for 6 hours at 40° C. The reaction was then quenched by adding aqueous saturated ammonium chloride solution (10 mL). Acetone was removed under reduced pressure and the aqueous phase was extracted with DCM (3×15 mL). The combined organic phase was removed under reduced pressure and the crude product was directly purified using reverse phase preparative HPLC (5% to 70% H$_2$O/MeCN, with n-propanol in water as modifier) to obtain the desired product as a white solid (4.1 mg, 67.8% yield). LC/MS analysis method 7, mass (ES+) m/z 382.4, retention time 1.05 min $^1$HNMR (CDCl$_3$): δ 10.15 (1H, brs), 7.15 (1H, t), 7.02 (1H, d), 6.67 (1H, brs), 6.65 (2H, m), 6.52 (1H, s), 3.82 ppm (8H, dt), 3.64 (8H, m)

Examples 3 to 38

Examples 3 to 38 in Table 2 below can be made using procedures analogous to those described in Examples 1 and 2 using the appropriate boronic acid or boronic ester intermediate.

TABLE 2

| Example Number | Structure and Name | ¹H NMR | LC/MS |
|---|---|---|---|
| 3 | 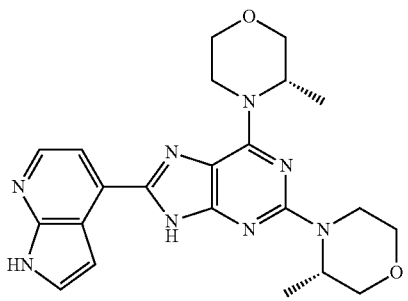2,6-Bis-((S)-3-methyl-morpholin-4-yl)-8-(1H-pyrrolo[2,3-b]pyridin-4-yl)-9H-purine | ¹H NMR (CDCl₃): 12.66 (1H, s), 8.26 (1H, s), 8.04 (1H, s), 7.62 (1H, s), 7.29 (1H, s), 5.80 (1H, m), 4.58 (2H, m), 4.14-3.98 (3H, m), 3.89-3.53 (6H, m), 3.45-3.34 (2H, m), 1.53 (3H,d), 1.41 (3H, d) | Method 7: C8-Broad Range-Neutral Retention Time: 1.15 min Mass (ES+): 435.5 |
| 4 | 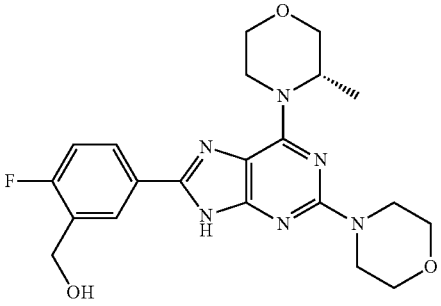{2-Fluoro-5-[6-((S)-3-methyl-morpholin-4-yl)-2-morpholin-4-yl-9H-purin-8-yl]-phenyl}-methanol | ¹H NMR (CD₃OD): 8.12 (1H, dd), 7.90 (1H, m), 7.17 (1H, t), 5.43 (1H, brs), 5.07 (1H, brs), 4.73 (2H, s), 3.99 (1H, dd), 3.81 (2H, d), 3.75-3.68 (8H, m), 3.66-3.62 (1H, dd), 3.48-3.40 (1H, m), 1.38 (3H, d) | Method 7: C8-Broad Range-Neutral Retention Time: 1.45 min Mass (ES+): 429.3 |
| 5 | 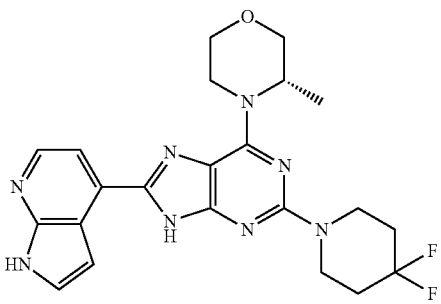2-(4,4-Difluoro-piperidin-1-yl)-8-(1H-indol-4-yl)6-((S)-3-methyl-morpholin-4-yl)-9H-purine | ¹H NMR (CD₃OD): 7.54 (2H, d), 7.46 (1H, d), 7.35 (1H, m), 7.26 (1H, m), 7.20 (1H, m), 5.51 (1H, brs), 5.10 (1H, brs), 4.02 (1H, dd), 3.94 (4H, m), 3.83 (2H, m), 3.70 (1H, m), 3.50 (1H, m), 1.97 (4H,m), 1.44(3H, d) | Method 7: C8-Broad Range-Neutral Retention Time: 1.58 min Mass (ES+): 454.3 |
| 6 | 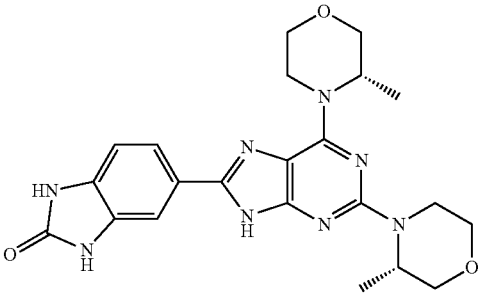5-[2,6-Bis-((S)-3-methyl-morpholin-4-yl)-9H-purin-8-yl]-1,3-dihydro-benzoimidazol-2-one | ¹H NMR (CD₃OD): 7.68 (2H, m), 7.11 (1H, d), 5.40 (1H, brs), 5.05 (1H, brs), 4.66 (1H, m), 4.24 (1H, m), 3.99-3.92 (2H, m), 3.81-3.67 (4H, m), 3.60-3.48 (2H, m), 3.25-3.13 (2H, m), 1.39 (3H,d), 1.25 (3H, d) | Method 7: C8-Broad Range-Neutral Retention Time: 1.02 min Mass (ES+): 451.6 |

TABLE 2-continued

| Example Number | Structure and Name | 1H NMR | LC/MS |
|---|---|---|---|
| 7 | 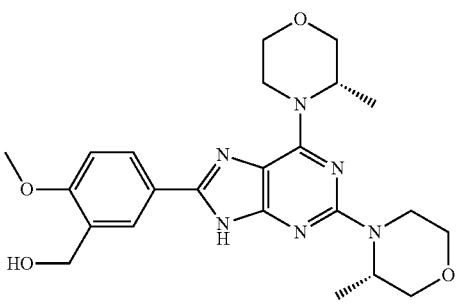<br>{5-[2,6-Bis-((S)-3-methyl-morpholin-4-yl)-9H-purin-8-yl]-2-methoxy-phenyl}-methanol | 1H NMR (CDCl3): 7.88 (2H, m), 6.97 (1H, s), 5.45 (1H, brs), 4.77 (2H, s), 4.58 (1H, brs), 4.21 (1H, brs), 4.08 (1H, brs), 4.07-3.71 (11H, m), 3.56 (2H, m), 3.31 (1H, brs), 1.46 (3H, d),1.33 (3H, d) | Method 7: C8-Broad Range-Neutral Retention Time: 1.09 min Mass (ES+): 455.6 |
| 8 | 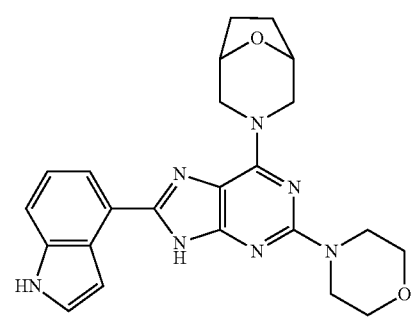<br>8-(1H-Indol-4-yl)-2-morpholin-4-yl-6-(8-oxa-3-aza-bicyclo[3.2.1]oct-3-yl)-9H-purine | 1H NMR (CD3OD): 7.53 (1H, d), 7.47 (1H, d), 7.36 (1H, d), 7.24 (1H, d), 7.20 (1H, t), 5.17 (2H, brs), 4.50 (2H, s), 3.74 (8H, m), 3.39 (2H, m), 1.95 (4H, m) | Method 7: C8-Broad Range-Neutral Retention Time: 1.16 min Mass (ES+): 432.5 |
| 9 | 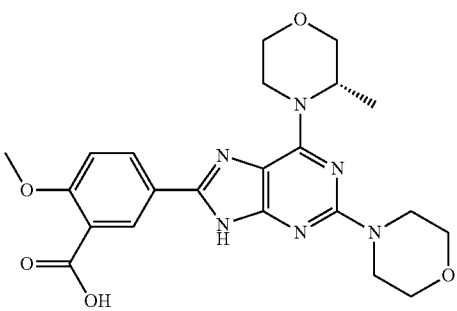<br>2-Methoxy-5-[6-((S)-3-methyl-morpholin-4-yl)-2-morpholin-4-yl-9H-purin-8-yl]-benzoic acid | 1H NMR (DMSO-d6): 12.91 (1H, s), 8.25 (1H, s), 8.10 (1H, d), 7.20 (1H, d), 5.34 (1H, brs), 5.00 (1H, brs), 3.98 (1H, m), 3.86 (3H, s), 3.76 (1H, m), 3.72-3.62 (10H, m), 3.56-3.49 (1H, m), 1.29 (3H, d) | Method 7: C8-Broad Range-Neutral Retention Time: 0.99 min Mass (ES+): 455.6 |
| 10 | 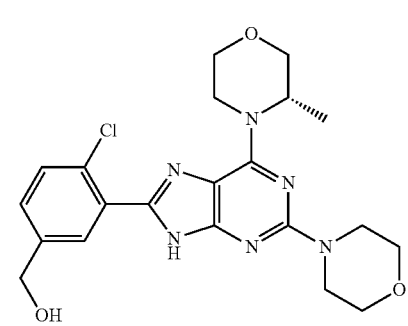<br>{4-Chloro-3-[6-((S)-3-methyl-mprpholin-4-yl)-2-morpholin-4-yl-9H-purin-8-yl]-phenyl}-methanol | 1H NMR (CD3OD): 7.79 (1H, m), 7.51 (1H, m), 7.44 (1H, m), 5.38 (1H, brs), 4.65 (2H, s), 4.62 (1H, s), 3.99 (1H, dd), 3.79 (2H, m), 3.73 (8H, m), 3.64 (1H, m), 3.41 (1H, m), 1.38 (3H, d) | Method 7: C8-Broad Range-Neutral Retention Time: 1.28 min Mass (ES+): 445.6 |

TABLE 2-continued

| Example Number | Structure and Name | ¹H NMR | LC/MS |
|---|---|---|---|
| 11 | 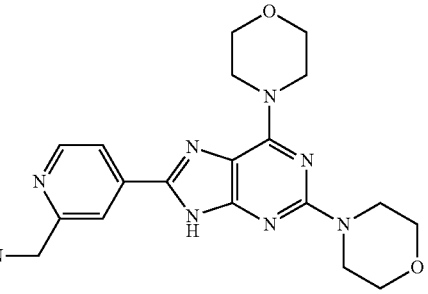<br>3-(2,6-Di-morpholin-4-yl-9H-purin-8-yl)-benzylamine | ¹H NMR (CD₃OD): 8.16 (1H, s), 8.01 (1H, d), 7.58 (1H, t), 7.52 (1H, m), 4.28 (4H, m), 4.20 (2H, s), 3.82 (4H, m), 3.75 (8H, m) | Method 7: C8-Broad Range-Neutral Retention Time: 0.73 min Mass (ES+): 396.5 |
| 12 | 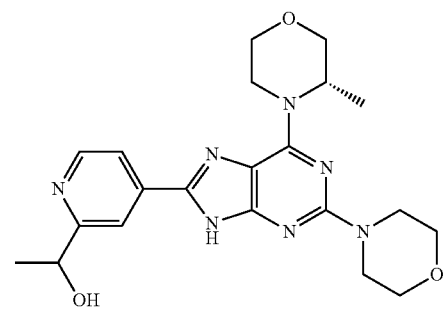<br>1-{3-[6-((S)-3-Methyl-morpholin-4-yl)-2-morpholin-4-yl-9H-purin-8-yl]-phenyl}-ethanol | ¹H NMR (CD₃OD): 8.01 (1H, s), 7.86 (1H, m), 7.42 (2H, d), 5.42 (1H, brs), 5.08 (1H, brs), 4.01 (1H, dd), 3.82 (2H, m), 3.73 (8H, m), 3.66 (1H, m), 3.47 (1H, m), 1.49 (3H,d), 1.38 (3H, d) | Method 7: C8-BroadRange-Neutral Retention Time: 1.13 min Mass (ES+): 425.5 |
| 13 | 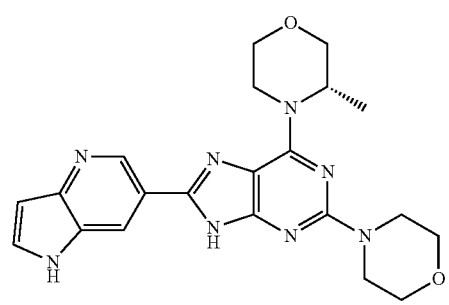<br>2,6-Di-morpholin-4-yl-8-(1H-pyrrolo[3,2-b]pyridin-6-yl)-9H-purine | ¹H NMR (DMSO-d₆): 13.05 (1H, brs), 11.50 (1H, s), 9.05 (1H, s), 8.37 (1H, s), 7.72 (1H, d), 6.59 (1H, d), 4.20 (4H, brs), 3.75 (4H, m), 3.66 (4H, m), 3.64 (4H m) | Method 7: C8-BroadRange-Neutral Retention Time: 0.94 min Mass (ES+): 407.4 |
| 14 | 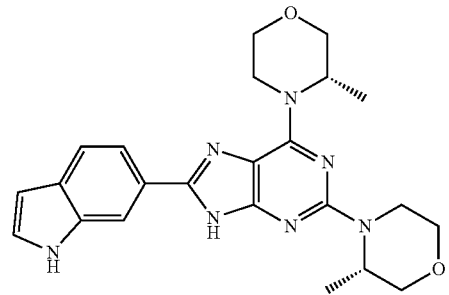<br>8-(1H-Indol-6-yl)-2,6-bis-((S)-3-methyl-morpholin-4-yl)-9H-purine | ¹H NMR (CD₃OD): 8.03 (1H, s), 7.64 (2H, m), 7.33 (1H, d), 6.49 (1H, d), 5.41 (1H, brs), 5.04 (1H, brs), 4.67 (1H, m), 4.26 (1H,dd), 4.01 (1H, dd), 3.94 (1H, dd), 3.82 (2H, s), 3.80-3.65 (3H, m), 3.58-3.43 (2H, m), 3.20 (1 H, m), 1.40 (3H,d), 1.26 (3H, d) | Method 7: C8-BroadRange-Neutral Retention Time: 1.30 min Mass (ES+): 434.5 |

TABLE 2-continued

| Example Number | Structure and Name | ¹H NMR | LC/MS |
|---|---|---|---|
| 15 | 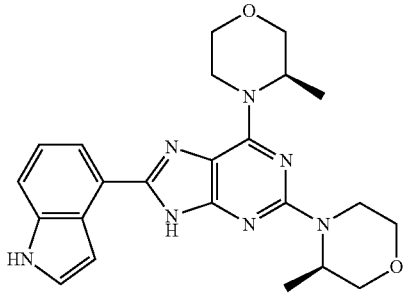 [SMILES: C[C@@H]1COCCN1c1nc(N2CCOC[C@H]2C)c2nc(-c3cccc4[nH]ccc34)[nH]c2n1]<br>8-(1H-Indol-4-yl)-2,6-bis-((R)-3-methyl-morpholin-4-yl)-9H-purine | ¹H NMR (CD₃OD): 7.54 (1H, d), 7.47 (1H, d), 7.35 (1H, d), 7.25 (1H, d), 7.20 (1H, t), 5.53 (1H, brs), 5.11 (1H, brs), 4.68 (1H, m), 4.28 (1H, m), 4.03 (1H, m), 3.99 (1H, m), 3.85 (2H, m), 3.73 (3H, m), 3.56 (2H, m), 3.25 (1H, m), 1.45 (3H, d), 1.27 (3H, d) | Method 7: C8-Broad Range-Neutral Retention Time: 1.45 min Mass (ES+): 434.3 |
| 16 | 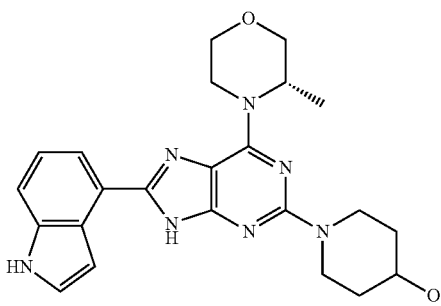<br>1-[8-(1H-Indol-4-yl)-6-((S)-3-methyl-morpholin-4-yl)-9H-purin-2-yl]-piperidin-4-ol | ¹H NMR (CD₃OD): 7.54 (1H, d), 7.47 (1H, d), 7.35 (1H, d), 7.25 (1H, d), 7.20 (1H, t), 5.50 (1H, brs), 5.11 (1H, brs), 4.45 (2H, m), 4.04 (1H, m), 3.85 (2H, m), 3.81 (2H, m), 1.89 (2H, m), 1.50 (2H, m), 1.45 (3H, d) | Method 7: C8-Broad Range-Neutral Retention Time: 1.28 min Mass (ES+): 434.4 |
| 17 | 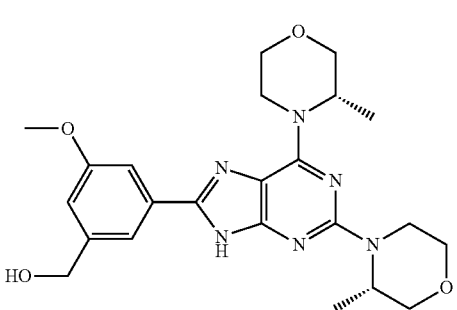<br>{3-[2,6-Bis-((S)-3-methyl-morpholin-4-yl)-9H-purin-8-yl]-5-methoxy-phenyl}-methanol | ¹H NMR (CD₃OD): δ 7.57 (1H,s), 7.44 (1H,s), 7.00 (1H,s), 5.40 (1H,brs), 5.07 (1H,brs), 4.67 (1H,m), 4.65 (2H,s), 4.26 (1H,dd), 4.01 (1H,dd), 3.93(1H,dd), 3.87 (3H,s), 3.81 (2H,d), 3.77-3.63 (3H,m), 3.58-3.40 (2H,m), 3.25-3.13 (1H,m), 1.39 (3H,d), 1.25 (3H,d) | Method 7: C8-Broad Range-Neutral Retention Time: 1.30 min Mass (ES+): 455.3 |
| 18 | 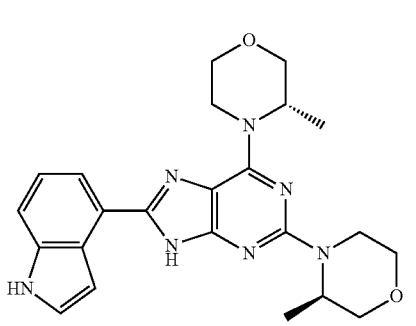<br>8-(1H-Indol-4-yl)-2-((R)-3-methyl-morpholin-4-yl)-6-((S)-3-metyl-morpholin-4-yl)-9H-purine | ¹H NMR (CD₃OD): δ 7.54 (1H,d), 7.47 (1H,d), 7.35 (1H,d), 7.24 (1H,d), 7.20 (1H,m), 5.49 (1H,brs), 5.13 (1H,brs), 4.68 (1H,m), 4.26 (1H,dd), 4.04 (1H,dd), 3.95 (3H,m), 3.84 (2H,s), 3.79-3.67 (3H,m), 3.59-3.47 (2H,m), 3.27-3.20 (1H,m), 1.44 (3H,d), 1.27 (3H,d) | Method 7: C8-Broad Range-Neutral Retention Time: 1.21 min Mass (ES+): 434.5 |

TABLE 2-continued

| Example Number | Structure and Name | $^1$H NMR | LC/MS |
|---|---|---|---|
| 19 | 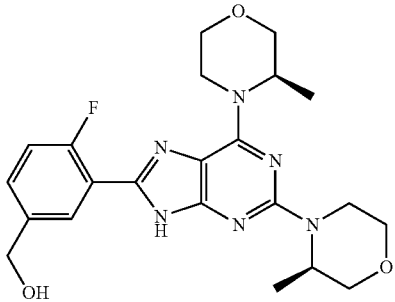<br>{3-[2,6-Bis-((R)-3-methyl-morpholin-4-yl)-9H-purin-8-yl]-4-fluoro-phenyl}-methanol | $^1$H NMR (CD$_3$OD): δ 8.09 (1H,dd), 7.42 (1H,m), 7.22 (1H,dd), 5.43 (1H,brs), 5.08\ (1H,brs), 4.67 (1H,m), 4.64 (2H,s), 4.27 (1H,dd), 4.01 (1H,dd), 3.94 (1H,dd), 3.81 (2H,s), 3.78-3.63 (3H,m), 3.56-3.41 (2H,m), 3.26-3.13 (1H,m), 1.39 (3H,d), 1.26 (3H, d) | Method 7: C8- Broad Range- Neutral Retention Time: 1.30 min Mass (ES+): 443.4 |
| 20 | 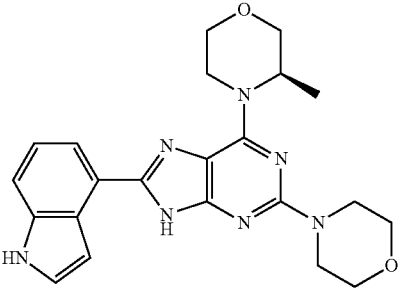<br>8-(1H-Indol-4-yl)-6-((R)-3-methyl-morpholin-4-yl)-2-morpholin-4-yl-9H-purine | $^1$H NMR (CDCl$_3$): δ 10.25 (1H,brs), 8.38 (1H,s), 7.51 (2H,t), 7.39 (1H,t), 7.32 (2H,m), 5.59 (1H,brs), 5.19 (1H,brs), 4.10 (1H,dd), 3.88 (2H,s), 3.84-3.76 (8H,m), 3.71 (1H,m), 3.61 (1H,m), 1,52 (3H,d) | Method 7: C8- Broad Range- Neutral Retention Time: 1.15 min Mass (ES+): 420.5 |
| 21 | 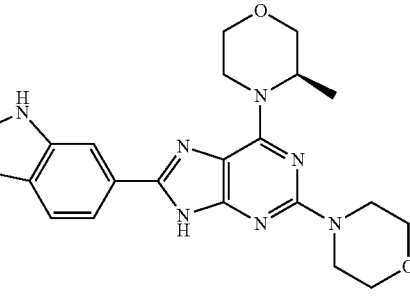<br>8-(1H-Indol-6-yl)-6-((R)-3-methyl-morpholin-4-yl)-2-morpholin-4-yl-9H-purine | $^1$H NMR (CDCl$_3$): δ 11.53 (1H,brs), 8.36 (1H,s), 7.93 (1H,s), 7.71 (1H,m), 7.56 (1H,m), 7.31 (1H,m), 6.60 (1H,s), 5.53 (1H,brs), 5.23 (1H,brs), 4.10 (2H,m), 3.88 (2H,m), 3.74 (1H,m), 3.69 (4H,m), 3.60 (4H,m), 1.58 (3H,d) | Method 7: C8- Neutral BroadRange- Retention Time: 1.19 min Mass (ES+): 420.5 |
| 22 | 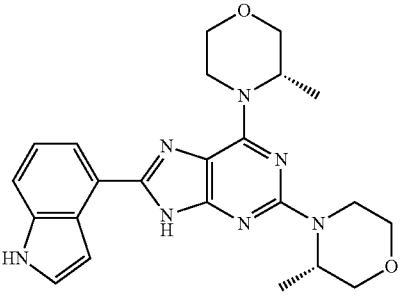<br>8-(1H-Indol-4-yl)-2,6-bis-((S)-3-methyl-morpholin-4-yl)-9H-purine | $^1$H NMR (CD$_3$OD): δ 7.54 (1H,d), 7.47 (1H,d), 7.35 (1H,d), 7.24 (1H,d), 7.20 (1H,t), 5.53 (1H, brs), 5.09 (1H,brs), 4.69 (1H,m), 4.27 (1H,dd), 4.04 (1H,dd), 3.96 (1H,dd), 3.85 (2H,s), 3.79-3.07 (3H,m), 3.59-3.49 (2H,m), 3.27-3.13 (1H,m), 1.45(3H,d), 1.27 (3H,d) | Method 7: C8- BroadRange- Neutral Retention Time: 1.20 min Mass (ES+): 434.4 |

TABLE 2-continued

| Example Number | Structure and Name | ¹H NMR | LC/MS |
|---|---|---|---|
| 23 | 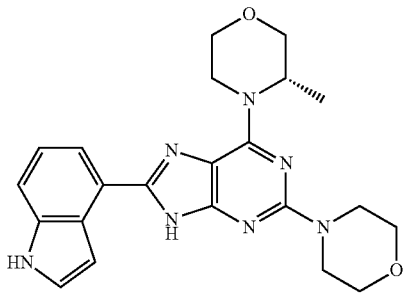<br>8-(1H-Indol-4-yl)-6-((S)-3-methyl-morpholin-4-yl)-2-morpholin-4-yl-9H-purine | ¹H NMR (CDCl₃): δ 10.28 (1H,brs), 8.38 (1H,s), 7.50 (2H,d), 7.39 (1H,m), 7.29 (2H,m), 5.60 (1H,brs), 5.20 (1H,brs), 4.11 (1H,dd), 3.88 (2H,s), 3.77 (8H,s), 3.71 (1H,m), 3.60 (1H,m), 1.51 (3H,d) | Method 7: C8-Broad Range-Neutral Retention Time: 1.10 min Mass (ES+): 420.5 |
| 24 | 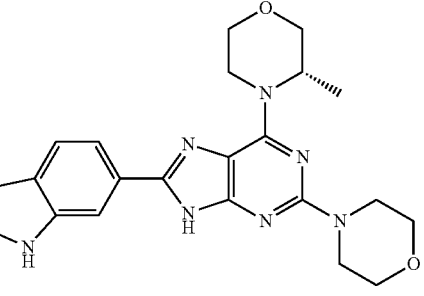<br>8-(1H-Indol-6-yl)-6-((S)-3-methyl-morpholin-4-yl)-2-morpholin-4-yl-9H-purine | ¹H NMR (CDCl₃): δ 12.19 (1H,brs), 8.47 (1H,s), 7.90 (1H,s), 7.68 (2H,m), 7.29 (1H,m), 6.59 (1H,s), 5.54 (1H,brs), 5.32 (1H,brs), 4.10 (1H,dd), 3.89 (2H,s), 3.77-3.50 (10H,m), 1.49 (3H,m) | Method 7: C8-Broad Range-Neutral Retention Time: 1.40 min Mass (ES+): 420.5 |
| 25 | 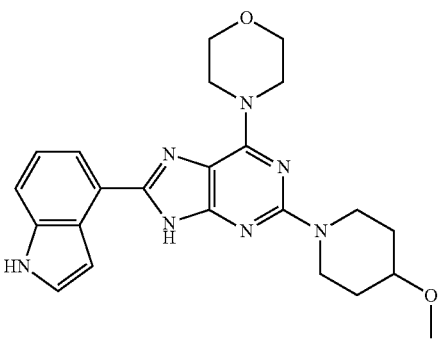<br>8-(1H-Indol-4-yl)-2-(4-methoxy-piperidin-1-yl)-6-morpholi-4-yl-9H-purine | ¹H NMR (CDCl₃): δ 10.5 (1H,brs), 8.38 (1H,s), 7.50 (2H,t), 7.38 (1H,m), 7.30 (1H,m), 4.40 (3H,m), 4.30 (3H,m), 3.91 (4H,m), 3.46 (1H,m), 3.41 (3H,s), 3.37 (2H,m), 1.97 (2H,m), 1.66 (2H,m) | Method 7: C8-Broadrange Neutral Retention Time: 1.15 min Mass (ES+): 434.5 |
| 26 | 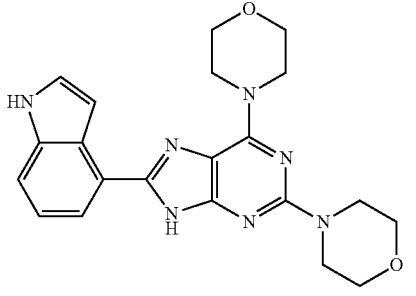<br>8-(1H-Indol-4-yl)-2,6-di-morpholin-4-yl-9H-purine | ¹H NMR (CD₃OD)δ 7.65 (1H,d), 7.62 (1H,d), 7.44 (1H,d), 7.28 (1H,t), 7.12 (1H,d), 4.25 (4H, brs), 3.90 (4H,m), 3.80 (8H,m) | Method 7: C8-Broadrange Neutral Retention Time: 1.3 min Mass (ES+): 406.2 |

TABLE 2-continued

| Example Number | Structure and Name | ¹H NMR | LC/MS |
|---|---|---|---|
| 27 | 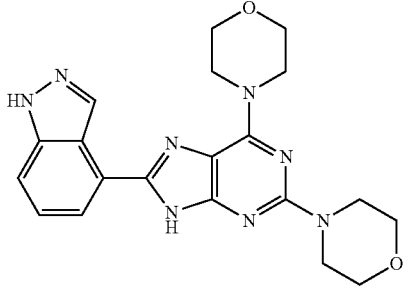<br>8-(1H-Indazol-4-yl)-2,6-di-morpholin-4-yl-9H-purine | ¹H NMR (DMSO-d₆)δ 8.70 (1H,s), 7.70 (1H,d), 7.60 (1H,d), 7.40 (1H,t), 7.32 (1H,m), 4.20 (4H,brs), 3.85 (4H,m), 3.65 (8H,m) | Method 7: C8-Neutral Broadrange-Retention Time: 1.2 min Mass (ES+): 407.3 |
| 28 | 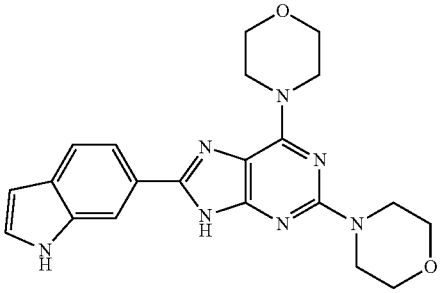<br>8-(1H-Indol-6-yl)-2,6-di-morpholin-4-yl-9H-purine | ¹H NMR (DMSO-d₆)δ 8.10 (1H,s), 7.75 (1H,d), 7.60 (1H,d), 7.45 (1H,m), 6.95 (1H,s), 4.19 (4H,brs), 3.75 (4H,m), 3.65 (8H,m) | Method 7: C8-Neutral Broadrange-Retention Time: 1.32 min Mass (ES+): 406.2 |
| 29 | 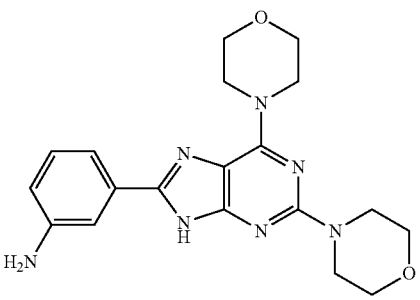<br>3-(2,6-Di-morpholin-4-yl-9H-purin-8-yl)-phenylamine | ¹H NMR (CD3OD)δ 8.15 (2H, m), 7.67 (1H,t), 7.48 (1H,m), 4.35 (4H,brs), 3.86 (4H m) 3.80 (8H brs) | Method 7: C8-Neutral Broadrange-Retention Time: 1.16 min Mass (ES+): 382.3 |
| 30 | 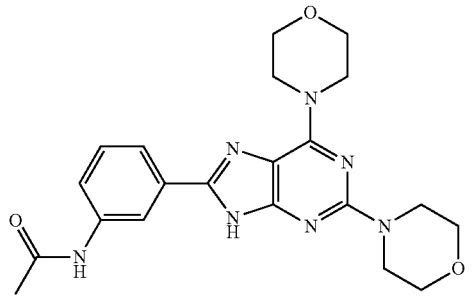<br>N-[3-(2,6-Di-morpholin-4-yl-9H-purin-8-yl)-phenyl]-acetamide | ¹H NMR(DMSO-d6)δ 8.22(1H,s), 7.70 (1H,d), 7.46 (1H,t), 4.20 (4H,brs), 3.75 (4H,m), 3.65 (8H,m), 2.10 (3H,s) | Method 3: C18-General-Neutral Retention Time: 1.22 min Mass (ES+): 424.1 |

| Example Number | Structure and Name | ¹H NMR | LC/MS |
|---|---|---|---|
| 31 | 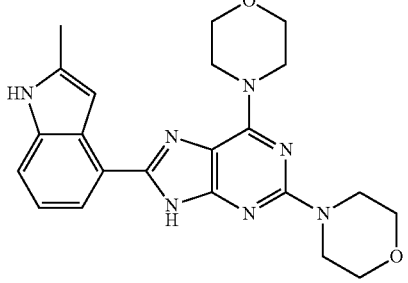<br>8-(20Methyl-1H-indol-4-yl)-2,6-di-morpholin-4-yl-9H-purine | ¹H NMR (DMSO-d₆) δ 7.60 (1H,d), 7.32 (1H,d), 7.05 (1H,t), 6.90 (1H,s), 4.25 (4H,brs), 3.80 (4H,m), 3.65 (8H,m), 2.45 (3H,s) | Method 3: C18-General-Retention Neutral Time: 1.36 min Mass (ES+): 420.3 |
| 32 | 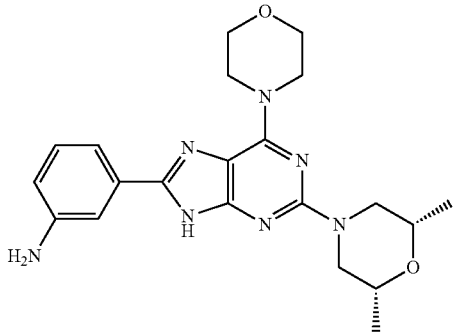<br>3-[2-((2S,6R)-2,6-Dimethyl-morpholin-4-yl)-6-morpholin-4-yl-9H-purin-8-yl]-phenylamine | ¹H NMR (DMSO-d₆) δ 7.85 (1H,brs), 7.80 (1H,m), 7.45 (1H,t), 7.17 (1H,d), 4.42 (2H,d), 4.19 (4H,brs), 3.75 (4H,m), 3.55 (2H,m), 2.45 (2H,m), 1.15 (6H,d) | Method 3: C18-General-Neutral Retention Time: 1.35 mm Mass (ES+): 410.3 |
| 33 | 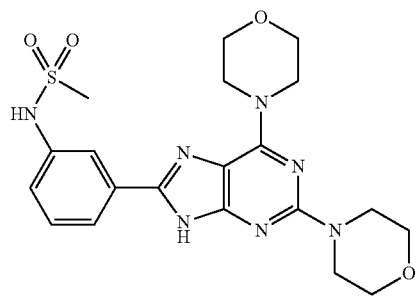<br>N-[3-(2,6-Di-morphlin-4-yl-9H-purin-8-yl)-phenyl]-methanesulfonamie | 1H NMR (DMSO-d6)δ 7.89 (1H,s), 7.76 (1H,d), 7.43 (1H,t), 7.27 (1H,d), 4.19 (4H,brs), 3.75 (4H,m), 3.65 (8H,m), 3.05 (s, 3H) | Method 3: C18-General-Neutral Retention Time: 1.23 min Mass (ES+): 460.2 |
| 34 | 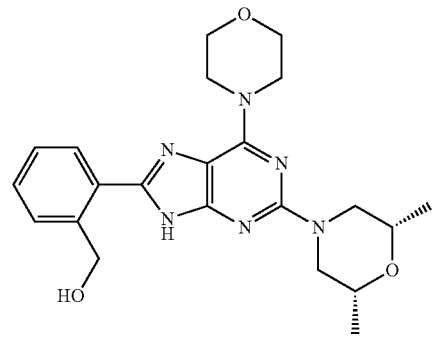<br>{2-[2-((2S,6R)-2,6-Dimethyl-morpholin-4-yl)-6-morpholin-4-yl-9H-purin-8-yl]-phenyl}-methanol | 1H NMR (CDCl₃)δ 11.0 (1H, brs), 7.70 (1H, m), 7.45 (3H, m), 4.72 (2H, s), 4.41 (2H, d), 4.24 (4H, s), 3.88 (4H, m), 3.57 (2H, m), 2.52 (2H, m), 1.23 (6H, d) | Method 3: General-Neutral Retention Time: 1.43 min Mass (ES+): 425.3 |

TABLE 2-continued

| Example Number | Structure and Name | $^1$H NMR | LC/MS |
|---|---|---|---|
| 35 | 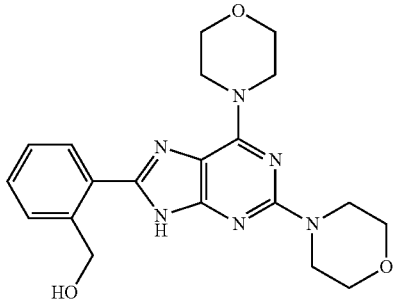<br>[2-(2,6-Di-morpholin-4-yl-9H-purin-8-yl)-phenyl]-methanol | $^1$H NMR (CDCl$_3$) δ 7.44 (1H, m), 7.19 (3H, m), 4.48 (2H, s), 4.0 (4H, brs), 3.63 (4H, m), 3.43 (8H, s) | Method 3: C18-General-Neutral Retention Time: 1.22 min Mass (ES+): 397.4 |
| 36 | 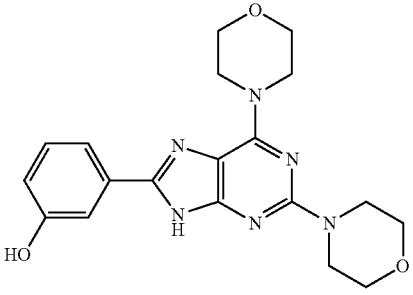<br>3-(2,6-Di-morpholin-4-yl-9H-purin-8-yl)-phenol | $^1$H NMR (DMSO-d$_6$) δ 12.88(1H, brs), 9.59 (1H, s), 7.46 (2H, m), 7.25 (1H, m), 6.79 (1H, m), 4.18 (4H, brs), 3.73 (4H, m), 3.65 (8H, m) | Method 3: C18-General-Neutral Retention Time: 1.18 min Mass (ES+): 383.3 |
| 37 | 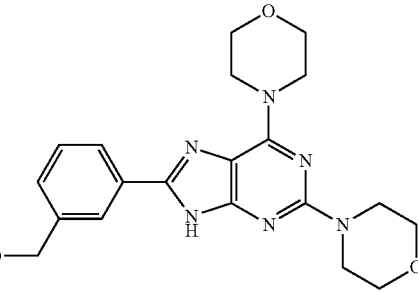<br>[3-(2,6-Di-morpholin-4-yl-9H-purin-8-yl)-phenyl]-methanol | $^1$H NMR (DMSO-d$_6$) δ 12.95(1H, brs), 8.03 (1H, s), 7.90 (1H, d), 7.42 (1H, m), 7.35 (1H, m), 5.27 (1H, t), 4.55 (2H, d), 4.19 (4H, brs), 3.74 (4H, m), 3.64 (8H, m) | Method 3: C18-General-Neutral Retention Time: 1.15 min Mass (ES+): 397.3 |
| 38 | 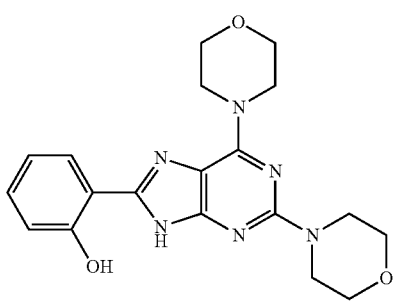<br>2-(2,6-Di-morpholin-4-yl-9H-purin-8-yl)-phenol | $^1$H NMR (CD$_3$OD) δ (1H, t), 6.95 (2H, m), 4.55 (1H, brs), 4.16 (4H, m), 3.82 (4H, m), 3.74 (8H, s) | Method 3: C18 General-Neutral Retention Time: 1.44 min Mass (ES+): 383.4 |

TABLE 3

| Example number | Structure and name | ¹H NMR | LC/MS |
|---|---|---|---|
| 39 | 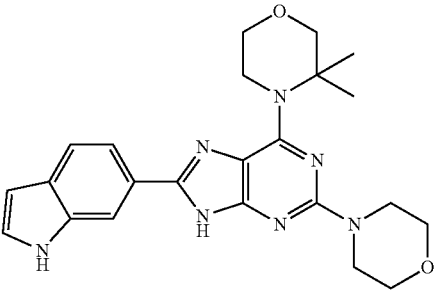<br>6-(3,3-Dimethyl-morpholin-4-yl)-8-(1H-indol-6-yl)-2-morpholin-4-yl-9H-purine | ¹H NMR (CD₃OD): 8.04(1H, s), 7.64(2H, m), 7.34(1H, d), 6.49(1 H, d), 4.34(2H, m), 4.01(2H,m), 3.77(8H, s), 3.52(2H, s), 1.60(6H, s) | Method 7: C8-Broadrange-Neutral Retention Time:1.18 min Mass (ES+): 434 |
| 40 | 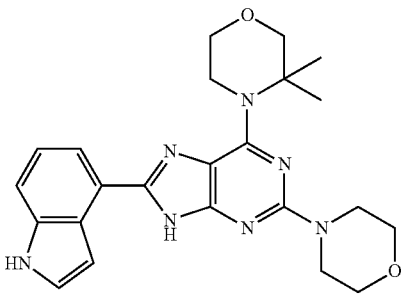<br>6-(3,3-Dimethyl-morpholin-4-yl)-8-(1H-indol-4-yl)-2-morpholin-4-yl-9H-purine | ¹H NMR (CD₃OD): 7.55(1H, d), 7.49(1H, d), 7.36(1H, d), 7.20(2H, m), 4.49(2H, m), 4.03(2H, m), 3.77(8H, s), 3.53(2H, s), 1.62(6H, s) | Method 7: C8-Broadrange-Neutral Retention Time:1.12 min Mass (ES+): 434.5 |
| 41 | 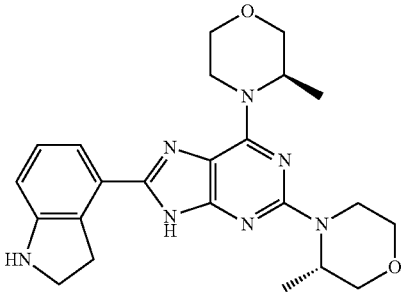 [SMILES: C[C@@H]1COCCN1c1nc(N2CCOC[C@@H]2C)nc2[nH]c(-c3cccc4c3CCN4)nc12]<br>8-(2,3-Dihydro-1H-indol-4-yl)-2-((S)-3-methyl-morpholin-4-yl)-6-((R)-3-methyl-morpholin-4-yl)-9H-purine | ¹H NMR (CD₃OD): 7.87(1H, d), 7.53(1H, t), 7.43(1H, d), 5.42(1H, brs), 5.05(1H, brs), 4.60(1H, m), 4.17(1H, d), 4.02(2H, m), 3.40-3.90(12H, m),1.45(3H, d), 1.32(3H, d) | Method 7: C8-Broadrange-Neutral Retention Time:1.30 min Mass (ES+): 436.6 |
| 42 | 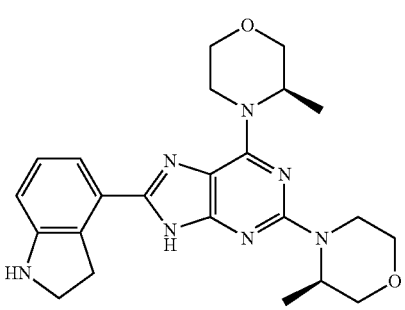<br>8-(2,3-Dihydro-1H-indol-4-yl)-2,6-bis-((R)-3-methyl-morpholin-4-yl)-9H-purine | ¹H NMR (CD₃OD): 7.88(1H, d), 7.54(1H, t), 7.44(1H, d), 5.48(1H, brs), 5.05(1H, brs), 4.58(1H, m), 4.20(1H, m), 4.01(2H, m), 3.37-3.88(12H, m), 1.46(3H, d), 1.33(3H,d) | Method 7: C8-Broadrange-Neutral Retention Time:1.30 min Mass (ES+): 436.6 |

TABLE 3-continued

| Example number | Structure and name | ¹H NMR | LC/MS |
|---|---|---|---|
| 43 | 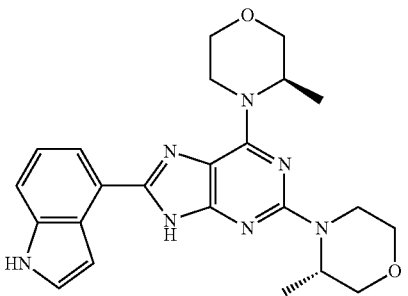 [SMILES: C[C@@H]1COCCN1c1nc(N2CCOC[C@@H]2C)nc2[nH]c(-c3cccc4[nH]ccc34)nc12]<br>8-(1H-indol-4-yl)-2-((S)-3-methyl-morpholin-4-yl)-6-((R)-3-methyl-morpholin-4-yl)-9H-purine | ¹H NMR (CD$_3$OD): 7.54(1H, m), 7.47(1H, m), 7.36(1H, d), 7.24(1H, m), 7.20(1H, m), 5.49(1 H, brs), 5.12(1H, brs), 4.68(1H, m), 4.27(1H, m), 4.03(1H, m), 3.95(1H, m), 3.85(2H, s), 3.76(3H, m), 3.56(2H, m), 3.24(1H, m), 1.44(3H, d), 1.27(3H, d) | Method 7: C8-Broad range-Neutral Retention Time:1.12 min Mass (ES+): 434.5 |
| 44 | 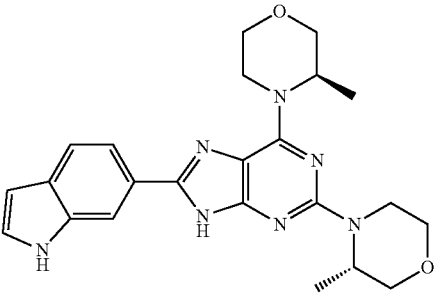<br>8-(1H-Indol-6-yl)-2-((S)-3-methyl-morpholin-4-yl)-6-((R)-3-methyl-morpholin-4-yl)-9H-purine | ¹H NMR (CD$_3$OD): 8.03(1H, s), 7.64(2H, m), 7.32(1H, s), 6.48(1H, s), 5.38(1H, brs), 5.08(1H, brs), 4.67(1H, m), 4.24(1H, m), 3.97(2H, m), 3.83(2H, s), 3.73(3H, m), 3.55(2H, m), 3.20(1H, m), 1.39(3H, d), 1.26(3H, d) | Method 7:C8-Broad range-Neutral Retention Time:1.18 min Mass (ES+): 434.5 |
| 45 | 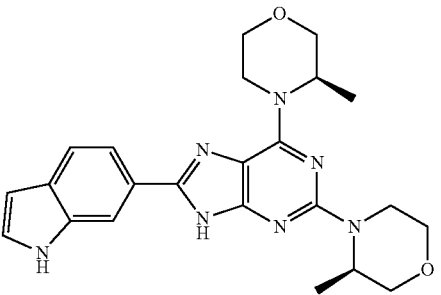<br>8-(1H-Indol-6-yl)-2,6-bis-((R)-3-methyl-morpholin-4-yl)-9H-purine | ¹H NMR (CD$_3$OD): 8.03(1H, s), 7.63(2H, m), 7.32(1H, d), 6.48(1H, d), 5.41(1H, brs), 5.07(1H, brs), 4.67(1H, m),4.26(1 H, m), 3.99(2H, m), 3.83(2H, s), 3.73(3H, m), 3.55(2H, m), 3.23(1H, m), 1.40(3H, d), 1.26(3H, d) | Method 7: C8-Broad range-Neutral Retention Time:1.27 min Mass (ES+): 434.4 |
| 46 | 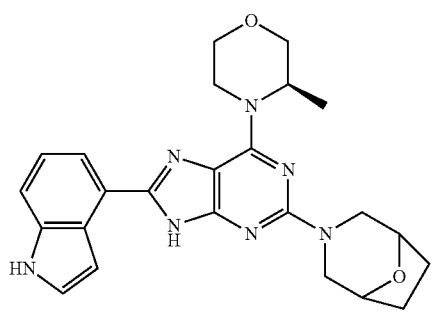<br>8-(1H-Indol-4-yl)-6-((R)-3-methyl-morpholin-4-yl)-2-(8-oxa-3-aza-bicyclo[3.2.1]oct-3-yl)-9H-purine | ¹H NMR (CD$_3$OD): 7.54(1H, d), 7.47(1H, d), 7.35(1H, d), 7.24(1H, d), 7.20(1H, m), 5.53(1H, brs), 5.11(1H, brs), 4.43(2H, s), 4.25(2H, d), 4.04(1H, m), 3.84(2H, m), 3.70(1H, m),3.48(1H, m), 3.10(2H, m), 1.88(4H, m), 1.44(3H, d) | Method 7: C8-Broad range-Neutral Retention Time:1.21 min Mass (ES+): 446.5 |

TABLE 3-continued

| Example number | Structure and name | ¹H NMR | LC/MS |
|---|---|---|---|
| 47 | 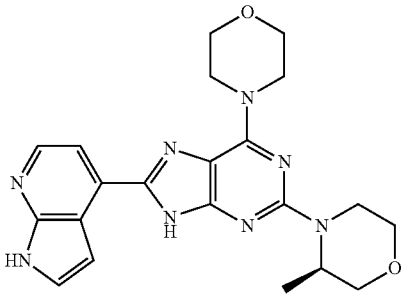<br>8-(1H-Indol-4-yl)-2-((R)-3-methyl-morpholin-4-yl)-6-morpholin-4-yl-9H-purine | ¹H NMR (CD₃OD): 7.53(1H, d), 7.49(1H, d), 7.35(1H, d), 7.20(2H, m), 4.69(1H, m), 4.31(5H, m)3.94(1H, m), 3.85(4H, m), 3.75(2H, m), 3.55(1H,m), 3.24(1H, m), 1.27(3H, d) | Method 7: C8-Broadrange-Neutral Retention Time:1.17 min Mass (ES+): 420.5 |
| 48 | 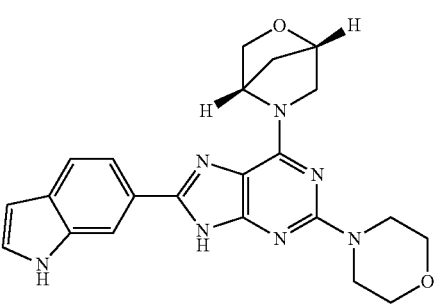<br>8-(1H-Indol-6-yl)-2-morpholin-4-yl-6-(1S,4S)-2-oxa-5-aza-bicyclo[2.2.1]hept-5-yl-9H-purine | ¹H NMR (CD₃OD): 8.04(1 H, s), 7.64(2H, m), 7.33(1H, d), 6.49(1H, d), 4.75(1H, s), 3.93(2H,m), 3.74(11H, m), 2.04(2H, s) | Method 7: C8-Broadrange-Neutral Retention Time:1.23 min Mass (ES+): 418.2 |
| 49 | 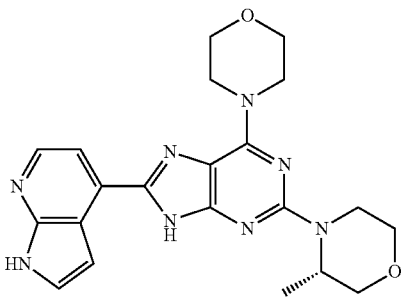<br>8-(1H-Indol-4-yl)-2-((R)-3-methyl-morpholin-4-yl)-6-morpholin-4-yl-9H-purine | ¹H NMR (CD₃OD): 8.04(1H, s), 7.63(2H, m), 7.33(1H, d), 6.48(1H, d), 4.68(1H, m), 4.24(5H, m), 3.94(1H,m), 3.83(4H,m), 3.74(2H,m), 3.56(1H,m), 3.23(1H, m), 1.26(3H,d) | Method 7: C8-Broad range-Neutral Retention Time:1.22 min Mass (ES+): 420.5 |
| 50 | 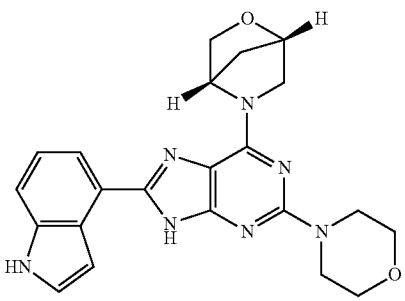<br>8-(1H-Indol-4-yl)-2-morpholin-4-yl-6-(1S,4S)-2-oxa-5-aza-bicyclo[2.2.1]hept-5-yl-9H-purine | ¹H NMR (CD₃OD): 7.54(1H, d), 7.48(1H, d), 7.36(1 H, d), 7.26(1H, m), 7.20(1H, t), 4.77(1 H, s), 3.97(3H, m), 3.75(10H, m), 2.07(2H, s) | Method 7: C8-Broad range-Neutral Retention Time:1 .19 min Mass (ES+): 418.3 |

TABLE 3-continued

| Example number | Structure and name | ¹H NMR | LC/MS |
|---|---|---|---|
| 51 | 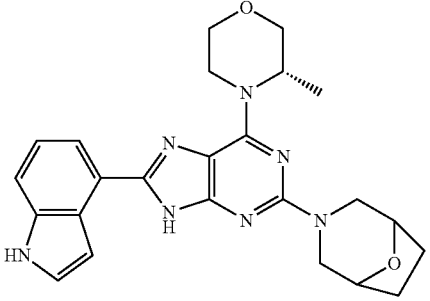<br>8-(1H-Indol-6-yl)-6-((S)-3-methyl-morpholin-4-yl)-2-(8-oxa-3-aza-bicyclo[3.2.1]oct-3-yl)-9H-purine | ¹H NMR (CD₃OD): 7.93(1H, s), 7.53(2H, m), 7.23(1H, d), 6.39(1H, d), 5.31(1H, brs), 4.95(1H, brs), 4.32(2H, s), 4.14(2H, d), 3.91(1H, m), 3.73(2H, s), 3.58(1H, m), 3.37(1H, m), 3.00(2H, d), 1.70(4H, m), 1.29(3H, d) | Method 7: C8-Broadrange-Neutral Retention Time:1.37 min Mass (ES+): 446.4 |
| 52 | 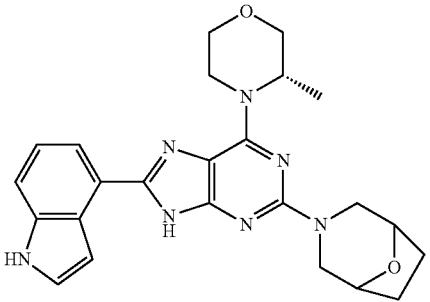<br>8-(1H-Indol-6-yl)-6-((S)-3-methyl-morpholin-4-yl)-2-(8-oxa-3-aza-bicyclo[3.2.1]oct-3-yl)-9H-purine | ¹H NMR (CD₃OD): 7.54(1H, d), 7.47(1H, d), 7.35(1H, d), 7.24(1H, d), 7.20(1H, t), 5.52(1H, brs), 5.09(1H, brs), 4.43(2H, s), 4.27(2H, d), 4.03(1H, m), 3.85(2H, s), 3.70(1H, m), 3.48(1H, m), 3.09(2H, d), 1.88(4H, m), 1.45(3H, d) | Method 7: C8-Broad range-Neutral Retention Time:1.22 min Mass (ES+): 446.5 |
| 53 | 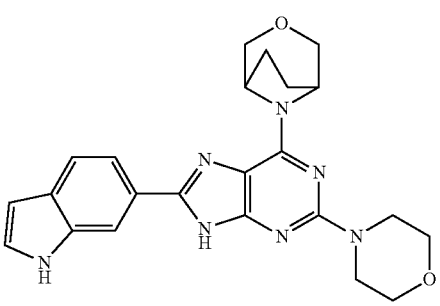<br>8-(1H-Indol-6-yl)-2-morpholin-4-yl-6-(3-oxa-8-aza-bicyclo[3.2.1]oct-8-yl)-9H-purine | ¹H NMR (CD₃OD): 8.04(1H, s), 7.63(2H, m), 7.33(1H, d), 6.49(1H, d), 5.30(2H, brs), 3.88(2H, d), 3.74(8H, m), 3.67(2H, d), 2.12(4H, m) | Method 7: C8-Broad range-Neutral Retention Time:1.32 min Mass (ES+): 432.4 |
| 54 | 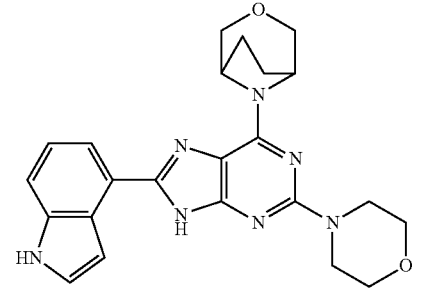<br>8-(1H-Indol-4-yl)-2-morpholin-4-yl-6-(3-oxa-8-aza-bicyclo[3.2.1]oct-8-yl)-9H-purine | ¹H NMR (CD₃OD): 7.55(1H, d), 7.48(1H, d), 7.36(1H, d), 7.20(2H, m), 5.37(2H, brs), 3.92(2H, d), 3.70(2H, d), 2.15(4H, m) | Method 7: C8-Broadrange-Neutral Retention Time:1.18 min Mass (ES+): 432.5 |

TABLE 3-continued

| Example number | Structure and name | ¹H NMR | LC/MS |
|---|---|---|---|
| 55 | 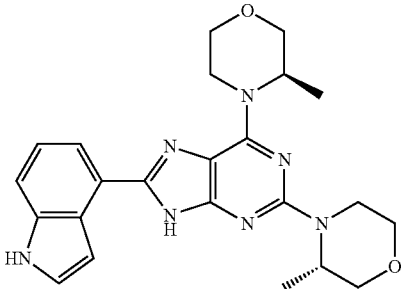<br>6-(1H-Indol-4-yl)-4-((R)-3-methyl-morpholin-4-yl)-2-((S)-3-methyl-morpholin-4-yl)-7H-pyrrolo[2,3-d]pyrimidine | ¹H NMR(DMSO-d$_6$): 11.66(1H, brs), 11.26(1H, br), 7.44(1 H, t), 7.35(2H, m), 7.12(1H, t), 6.84(1H, d), 4.74(1H, brs), 4.55(1 H, brs), 4.41 (1H, t), 4.14(1H, t), 3.99(1H, d), 3.92(1H, d) 3.75(3H, m), 3.51(4H, m), 3.16 (1H, m), 1.32 (3H, t), 1.20 (3H, m) | Method 7: C8-Broad range-Neutral Retention Time:1.17 min Mass (ES +): 433.5 |
| 56 | 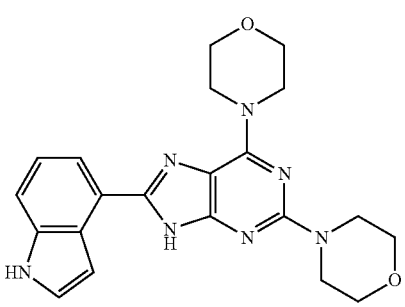<br>6-(1H-Indol-4-yl)-2,4-di-morpholin-4-yl-7H-pyrrolo[2,3-d]pyrimidine | ¹H NMR(DMSO-d$_6$): 11.52(1H, brs), 11.26(1H, brs), 7.42(1H, brs), 7.34(2H, m), 7.1(1H, t), 6.85(2H, brs), 3.85(4H, m), 3.75(4H, m) 3.66(8H, m), | Method 7: C8-Broad range-Neutral Retention Time:1.03 min Mass (ES +): 405.5 |

TABLE 4

| Example Number | Test 1: PI3Kα IC$_{50}$ (nM) | Test 2: mTOR IC$_{50}$ (nM) | Test 3: TSC1−/− IC50 (nM) | Test 4: Autophagy EC$_{50}$ |
|---|---|---|---|---|
| 39 | 2530 | 160 | 146 | 2317 |
| 40 | 6470 | 350 | 841 | >8000 |
| 41 | 3350 | 30 | 457 | 2901 |
| 42 | 4910 | 40 | 99 | 4627 |
| 43 | 1010 | 40 | 39 | 160 |
| 44 | 5950 | 140 | 388 | 395 |
| 45 | 7080 | 650 | 989 | >400 |
| 46 | 580 | 30 | 100 | 171 |
| 47 | 60 | 60 | 111 | 461 |
| 48 | 4300 | 1010 | 1463 | 6410 |
| 49 | 4430 | 370 | 678 | >500 |
| 50 | 4220 | 1200 | 920 | 8673 |
| 51 | 5940 | 220 | 228 | 284 |
| 52 | 420 | 50 | 88 | 386 |
| 53 | >9100 | 190 | 528 | 782 |
| 54 | 5790 | 150 | 309 | 1253 |
| 55 | 1440 | 2670 | 71 | 1000 |
| 56 | 2010 | 2390 | 174 | 3651 |

The invention claimed is:

1. A compound of formula (I), or a pharmaceutically acceptable salt thereof,

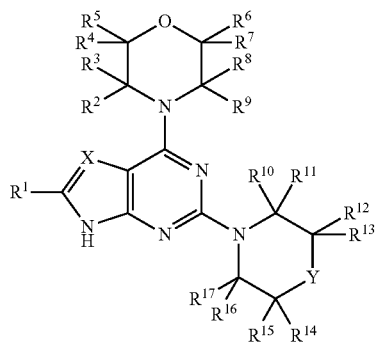

(I)

wherein
X represents N;
$R^1$ represents

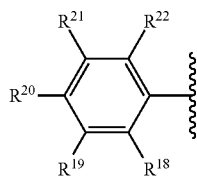

wherein
$R^{18}$ and $R^{22}$ independently represent hydrogen, halogen, hydroxy or hydroxy-$C_{1-3}$alkyl-;
$R^{19}$ and $R^{21}$ independently represent hydrogen, amino, hydroxy, carboxy, $C_{1-3}$alkoxy, amino-$C_{1-3}$alkyl-, $C_{1-3}$alkyl-C(=O)—NH—, $C_{1-3}$alkyl-S(=O)$_m$—NH— or hydroxy-$C_{1-3}$alkyl-;
m represents 0, 1 or 2;
$R^{20}$ represents hydrogen, halogen or $C_{1-3}$alkoxy
wherein at least one of $R^{18}$, $R^{19}$, $R^{20}$, $R^{21}$ and $R^{22}$ is not hydrogen; or
$R^1$ is selected from the group consisting of

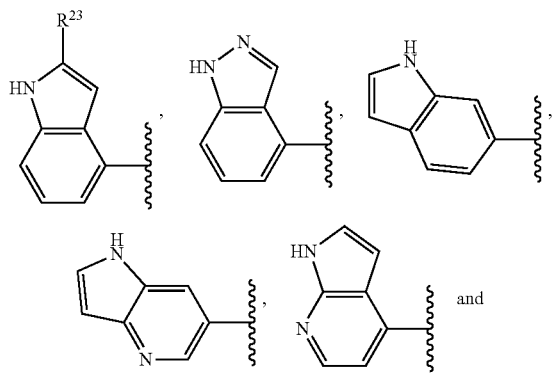

and

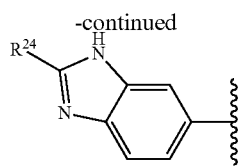

wherein
$R^{23}$ represents hydrogen or methyl;
$R^{24}$ represents hydrogen, oxo or $C_{1-3}$alkyl;
$R^2, R^3, R^4, R^5, R^6, R^7, R^8, R^9, R^{10}, R^{11}, R^{12}, R^{13}, R^{14}, R^{15}, R^{16}$ and $R^{17}$ independently represent hydrogen or methyl;
or $R^2$ and $R^8$ together form an ethylene bridge;
or $R^2$ and $R^6$ together form a methylene bridge;
or $R^{12}$ and $R^{14}$ together form an ethylene bridge; and
Y represents O, CHR$^{25}$ or CR$^{26}$R$^{27}$
wherein
$R^{25}$ represents hydroxy or $C_{1-3}$alkoxy; and
$R^{26}$ and $R^{27}$ independently represent hydrogen or halogen.

2. A compound of formula (I), or a pharmaceutically acceptable salt thereof,

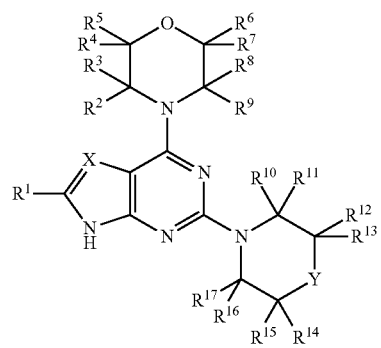

(I)

wherein
X represents N;
$R^1$ represents

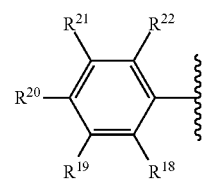

wherein
$R^{18}$ and $R^{22}$ independently represent hydrogen, halogen, hydroxy or hydroxy-$C_{1-3}$alkyl-;
$R^{19}$ and $R^{21}$ independently represent hydrogen, amino, hydroxy, carboxy, $C_{1-3}$alkoxy, amino-$C_{1-3}$alkyl-, $C_{1-3}$alkyl-C(=O)—NH—, $C_{1-3}$alkyl-S(=O)$_m$—NH— or hydroxy-$C_{1-3}$alkyl-;
m represents 0, 1 or 2;
$R^{20}$ represents hydrogen, halogen or $C_{1-3}$alkoxy
wherein at least one of $R^{18}$, $R^{19}$, $R^{20}$, $R^{21}$ and $R^{22}$ is not hydrogen; or $R^1$ is selected from the group consisting of

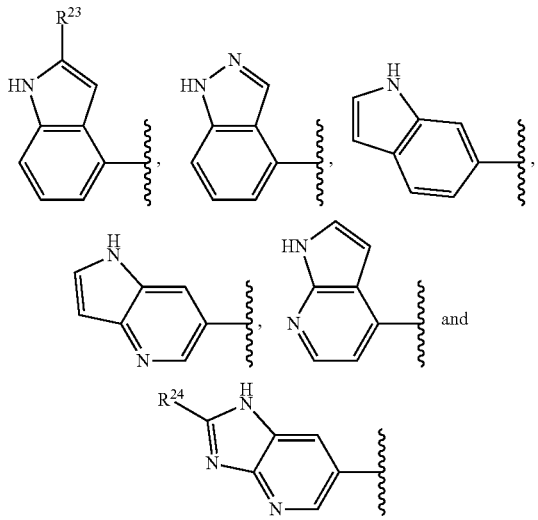

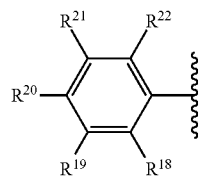

wherein
$R^{23}$ represents hydrogen or methyl;
$R^{24}$ represents hydrogen, oxo or $C_{1-3}$alkyl;
$R^2, R^3, R^4, R^5, R^6, R^7, R^8, R^9, R^{10}, R^{11}, R^{12}, R^{13}, R^{14}, R^{15}, R^{16}$ and $R^{17}$ independently represent hydrogen or methyl; or $R^5$ and $R^6$ together form an ethylene bridge; and
Y represents O, $CHR^{25}$ or $CR^{26}R^{27}$
wherein
$R^{25}$ represents hydroxy or $C_{1-3}$alkoxy; and
$R^{26}$ and $R^{27}$ independently represent hydrogen or halogen.

3. A compound according to claim 1, or a pharmaceutically acceptable salt thereof, wherein $R^1$ represents

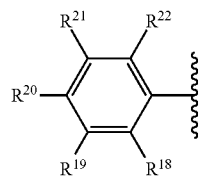

wherein
$R^{18}$ and $R^{22}$ independently represent hydrogen, halogen, hydroxy or hydroxy-$C_{1-3}$alkyl-;
$R^{19}$ and $R^{21}$ independently represent hydrogen, amino, hydroxy, carboxy, $C_{1-3}$alkoxy, amino-$C_{1-3}$alkyl-, $C_{1-3}$alkyl-C(=O)—NH—, $C_{1-3}$alkyl-S(=O)$_m$—NH— or hydroxy-$C_{1-3}$alkyl-;
m represents 0, 1 or 2; and
$R^{20}$ represents hydrogen, halogen or $C_{1-3}$alkoxy
wherein at least one of $R^{18}, R^{19}, R^{20}, R^{21}$ and $R^{22}$ is not hydrogen.

4. A compound according to claim 1, or a pharmaceutically acceptable salt thereof, wherein $R^1$ is selected from the group consisting of

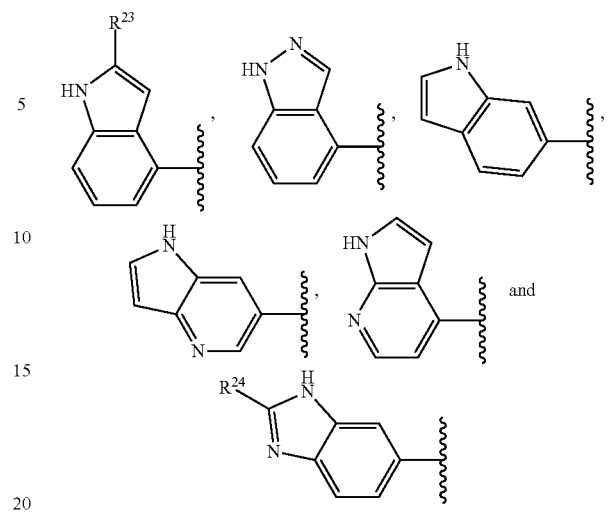

wherein
$R^{23}$ represents hydrogen or methyl; and
$R^{24}$ represents hydrogen, oxo or $C_{1-3}$alkyl.

5. A compound according to claim 1, or a pharmaceutically acceptable salt thereof, wherein Y represents O.

6. A compound according to claim 1, or a pharmaceutically acceptable salt thereof, wherein Y represents $CHR^{26}$ or $CR^{27}R^{28}$.

7. A compound according to claim 1, which is selected from:
3-[2-((2S,6R)-2,6-Dimethyl-morpholin-4-yl)-6-morpholin-4-yl-9H-purin-8-yl]-phenol;
2,6-Bis-((S)-3-methyl-morpholin-4-yl)-8-(1H-pyrrolo[2,3-b]pyridin-4-yl)-9H-purine;
{2-Fluoro-5-[6-((S)-3-methyl-morpholin-4-yl)-2-morpholin-4-yl-9H-purin-8-yl]-phenyl}-methanol;
2-(4,4-Difluoro-piperidin-1-yl)-8-(1H-indol-4-yl)-6-((S)-3-methyl-morpholin-4-yl)-9H-purine;
5-[2,6-Bis-((S)-3-methyl-morpholin-4-yl)-9H-purin-8-yl]-1,3-dihydro-benzoimidazol-2-one;
{5-[2,6-Bis-((S)-3-methyl-morpholin-4-yl)-9H-purin-8-yl]-2-methoxy-phenyl}-methanol;
8-(1H-Indol-4-yl)-2-morpholin-4-yl-6-(8-oxa-3-aza-bicyclo[3.2.1]oct-3-yl)-9H-purine;
2-Methoxy-5-[6-((S)-3-methyl-morpholin-4-yl)-2-morpholin-4-yl-9H-purin-8-yl]-benzoic acid;
{4-Chloro-3-[6-((S)-3-methyl-morpholin-4-yl)-2-morpholin-4-yl-9H-purin-8-yl]-phenyl}-methanol;
3-(2,6-Di-morpholin-4-yl-9H-purin-8-yl)-benzylamine;
1-{3-[6-((S)-3-Methyl-morpholin-4-yl)-2-morpholin-4-yl-9H-purin-8-yl]-phenyl}-ethanol;
2,6-Di-morpholin-4-yl-8-(1H-pyrrolo[3,2-b]pyridin-6-yl)-9H-purine;
8-(1H-Indol-6-yl)-2,6-bis-((S)-3-methyl-morpholin-4-yl)-9H-purine;
8-(1H-Indol-4-yl)-2,6-bis-((R)-3-methyl-morpholin-4-yl)-9H-purine;
1-[8-(1H-Indol-4-yl)-6-((S)-3-methyl-morpholin-4-yl)-9H-purin-2-yl]-piperidin-4-ol;
{3-[2,6-Bis-((S)-3-methyl-morpholin-4-yl)-9H-purin-8-yl]-5-methoxy-phenyl}-methanol;
8-(1H-Indol-4-yl)-2-((R)-3-methyl-morpholin-4-yl)-6-((S)-3-methyl-morpholin-4-yl)-9H-purine;
{3-[2,6-Bis-((R)-3-methyl-morpholin-4-yl)-9H-purin-8-yl]-4-fluoro-phenyl}-methanol;

8-(1H-Indol-4-yl)-6-((R)-3-methyl-morpholin-4-yl)-2-morpholin-4-yl-9H-purine;
8-(1H-Indol-6-yl)-6-((R)-3-methyl-morpholin-4-yl)-2-morpholin-4-yl-9H-purine;
8-(1H-Indol-4-yl)-2,6-bis-((S)-3-methyl-morpholin-4-yl)-9H-purine;
8-(1H-Indol-4-yl)-6-((S)-3-methyl-morpholin-4-yl)-2-morpholin-4-yl-9H-purine;
8-(1H-Indol-6-yl)-6-((S)-3-methyl-morpholin-4-yl)-2-morpholin-4-yl-9H-purine;
8-(1H-Indol-4-yl)-2-(4-methoxy-piperidin-1-yl)-6-morpholin-4-yl-9H-purine;
8-(1H-Indol-4-yl)-2,6-di-morpholin-4-yl-9H-purine;
8-(1H-Indazol-4-yl)-2,6-di-morpholin-4-yl-9H-purine;
8-(1H-Indol-6-yl)-2,6-di-morpholin-4-yl-9H-purine;
3-(2,6-Di-morpholin-4-yl-9H-purin-8-yl)-phenylamine;
N-[3-(2,6-Di-morpholin-4-yl-9H-purin-8-yl)-phenyl]-acetamide;
8-(2-Methyl-1H-indol-4-yl)-2,6-di-morpholin-4-yl-9H-purine;
3-[2-((2S,6R)-2,6-Dimethyl-morpholin-4-yl)-6-morpholin-4-yl-9H-purin-8-yl]-phenylamine;
N-[3-(2,6-Di-morpholin-4-yl-9H-purin-8-yl)-phenyl]-methanesulfonamide;
{2-[2-((2S,6R)-2,6-Dimethyl-morpholin-4-yl)-6-morpholin-4-yl-9H-purin-8-yl]-phenyl}-methanol;
[2-(2,6-Di-morpholin-4-yl-9H-purin-8-yl)-phenyl]-methanol;
3-(2,6-Di-morpholin-4-yl-9H-purin-8-yl)-phenol;
[3-(2,6-Di-morpholin-4-yl-9H-purin-8-yl)-phenyl]-methanol;
2-(2,6-Di-morpholin-4-yl-9H-purin-8-yl)-phenol;
6-(3,3-Dimethyl-morpholin-4-yl)-8-(1H-indol-6-yl)-2-morpholin-4-yl-9H-purine;
6-(3,3-Dimethyl-morpholin-4-yl)-8-(1H-indol-4-yl)-2-morpholin-4-yl-9H-purine;
8-(1H-Indol-4-yl)-2-((S)-3-methyl-morpholin-4-yl)-6-((R)-3-methyl-morpholin-4-yl)-9H-purine;
8-(1H-Indol-6-yl)-2-((S)-3-methyl-morpholin-4-yl)-6-((R)-3-methyl-morpholin-4-yl)-9H-purine;
8-(1H-Indol-6-yl)-2,6-bis-((R)-3-methyl-morpholin-4-yl)-9H-purine;
8-(1H-Indol-4-yl)-6-((R)-3-methyl-morpholin-4-yl)-2-(8-oxa-3-aza-bicyclo[3.2.1]oct-3-yl)-9H-purine;
8-(1H-Indol-4-yl)-2-((R)-3-methyl-morpholin-4-yl)-6-morpholin-4-yl-9H-purine;
8-(1H-Indol-6-yl)-2-morpholin-4-yl-6-(1S,4S)-2-oxa-5-aza-bicyclo[2.2.1]hept-5-yl-9H-purine;
8-(1H-Indol-4-yl)-2-((S)-3-methyl-morpholin-4-yl)-6-morpholin-4-yl-9H-purine;
8-(1H-Indol-4-yl)-2-morpholin-4-yl-6-(1S,4S)-2-oxa-5-aza-bicyclo[2.2.1]hept-5-yl-9H-purine;
8-(1H-Indol-6-yl)-6-((S)-3-methyl-morpholin-4-yl)-2-(8-oxa-3-aza-bicyclo[3.2.1]oct-3-yl)-9H-purine;
8-(1H-Indol-4-yl)-6-((S)-3-methyl-morpholin-4-yl)-2-(8-oxa-3-aza-bicyclo[3.2.1]oct-3-yl)-9H-purine;
8-(1H-Indol-6-yl)-2-morpholin-4-yl-6-(3-oxa-8-aza-bicyclo[3.2.1]oct-8-yl)-9H-purine;
8-(1H-Indol-4-yl)-2-morpholin-4-yl-6-(3-oxa-8-aza-bicyclo[3.2.1]oct-8-yl)-9H-purine;
and pharmaceutically acceptable salts thereof.

8. A pharmaceutical composition comprising a compound according to claim 1, or a pharmaceutically acceptable salt thereof, and a pharmaceutically acceptable excipient, diluent or carrier.

9. A combination comprising a therapeutically effective amount of a compound according to claim 1, or a pharmaceutically acceptable salt thereof, and a second drug substance, for simultaneous or sequential administration.

10. A compound which is 8-(1H-Indol-4-yl)-2,6-bis-((R)-3-methyl-morpholin-4-yl)-9H-purine having the following formula:

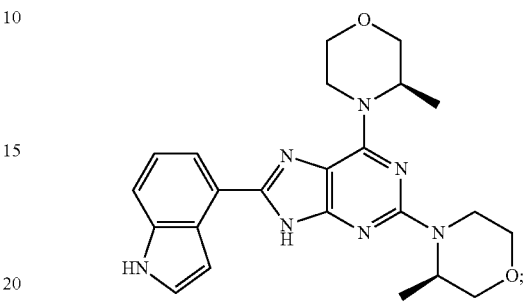

or a pharmaceutically acceptable salt thereof.

11. A compound which is 8-(2,3-Dihydro-1H-indol-4-yl)-2-((S)-3-methyl-morpholin-4-yl)-6-((R)-3-methyl-morpholin-4-yl)-9H-purine having the following formula

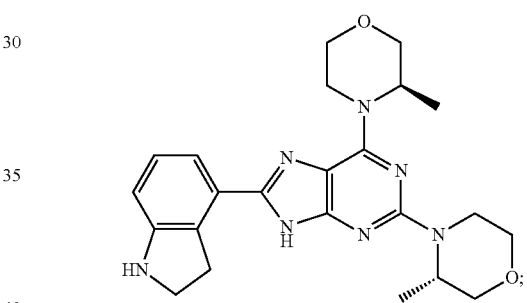

or a pharmaceutically acceptable salt thereof.

12. A compound which is 8-(1H-Indol-4-yl)-2-((S)-3-methyl-morpholin-4-yl)-6-((R)-3-methyl-morpholin-4-yl)-9H-purine having the following formula

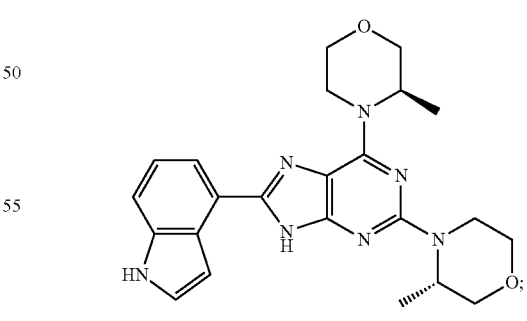

or a pharmaceutically acceptable salt thereof.

13. A compound which is 8-(1H-Indol-4-yl)-6-((R)-3-methyl-morpholin-4-yl)-2-(8-oxa-3-aza-bicyclo[3.2.1]oct-3-yl)-9H-purine having the following formula

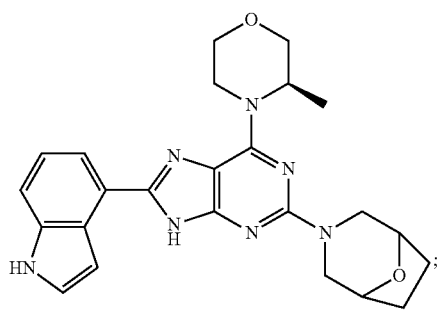 [SMILES: C[C@@H]1COCCN1c1nc(N2CC3CCC(C2)O3)nc2[nH]c(-c3cccc4[nH]ccc34)nc12]
or a pharmaceutically acceptable salt thereof.
* * * * *

SEQUENCE LISTING

```
<160> NUMBER OF SEQ ID NOS: 5

<210> SEQ ID NO 1
<211> LENGTH: 42
<212> TYPE: DNA
<213> ORGANISM: Artificial
<220> FEATURE:
<223> OTHER INFORMATION: PCR primer

<400> SEQUENCE: 1
gctagcatgc gagaatatga tagattatat gaagaatata cc                          42

<210> SEQ ID NO 2
<211> LENGTH: 45
```

```
<212> TYPE: DNA
<213> ORGANISM: Artificial
<220> FEATURE:
<223> OTHER INFORMATION: PCR primer

<400> SEQUENCE: 2
gcctccacca cctccgcctg gtttaatgct gttcatacgt ttgtc               45

<210> SEQ ID NO 3
<211> LENGTH: 42
<212> TYPE: DNA
<213> ORGANISM: Artificial
<220> FEATURE:
<223> OTHER INFORMATION: PCR primer

<400> SEQUENCE: 3
tactagtccg cctccaccac ctccgcctcc accacctccg cc                  42

<210> SEQ ID NO 4
<211> LENGTH: 1180
<212> TYPE: PRT
<213> ORGANISM: Artificial
<220> FEATURE:
<223> OTHER INFORMATION: Fusion protein of P85 alpha and P110 alpha
      subunits of human PI3 kinase expressed  from pBlueBac 4.5 vector.

<400> SEQUENCE: 4

Met Arg Glu Tyr Asp Arg Leu Tyr Glu Glu Tyr Thr Arg Thr Ser Gln
1               5                   10                  15

Glu Ile Gln Met Lys Arg Thr Ala Ile Glu Ala Phe Asn Glu Thr Ile
            20                  25                  30

Lys Ile Phe Glu Glu Gln Cys Gln Thr Gln Glu Arg Tyr Ser Lys Glu
        35                  40                  45

Tyr Ile Glu Lys Phe Lys Arg Glu Gly Asn Glu Lys Glu Ile Gln Arg
    50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                85                  90                  95

Tyr Arg Glu Ile Asp Lys Arg Met Asn Ser Ile Lys Pro Gly Gly Gly
            100                 105                 110

Gly Gly Gly Gly Gly Gly Gly Gly Leu Val Glu Cys Leu Leu Pro
        115                 120                 125

Asn Gly Met Ile Val Thr Leu Glu Cys Leu Arg Glu Ala Thr Leu Ile
    130                 135                 140

Thr Ile Lys His Glu Leu Phe Lys Glu Ala Arg Lys Tyr Pro Leu His
145                 150                 155                 160

Gln Leu Leu Gln Asp Glu Ser Ser Tyr Ile Phe Val Ser Val Thr Gln
                165                 170                 175

Glu Ala Glu Arg Glu Glu Phe Phe Asp Glu Thr Arg Arg Leu Cys Asp
            180                 185                 190

Leu Arg Leu Phe Gln Pro Phe Leu Lys Val Ile Glu Pro Val Gly Asn
        195                 200                 205

Arg Glu Glu Lys Ile Leu Asn Arg Glu Ile Gly Phe Ala Ile Gly Met
    210                 215                 220

Pro Val Cys Glu Phe Asp Met Val Lys Asp Pro Glu Val Gln Asp Phe
225                 230                 235                 240

Arg Arg Asn Ile Leu Asn Val Cys Lys Glu Ala Val Asp Leu Arg Asp
                245                 250                 255
```

```
Leu Asn Ser Pro His Ser Arg Ala Met Tyr Val Tyr Pro Asn Val
            260                 265                 270

Glu Ser Ser Pro Glu Leu Pro Lys His Ile Tyr Asn Lys Leu Asp Lys
                275                 280                 285

Gly Gln Ile Ile Val Val Ile Trp Val Ile Val Ser Pro Asn Asn Asp
    290                 295                 300

Lys Gln Lys Tyr Thr Leu Lys Ile Asn His Asp Cys Val Pro Glu Gln
305                 310                 315                 320

Val Ile Ala Glu Ala Ile Arg Lys Lys Thr Arg Ser Met Leu Leu Ser
                325                 330                 335

Ser Glu Gln Leu Lys Leu Cys Val Leu Glu Tyr Gln Gly Lys Tyr Ile
                340                 345                 350

Leu Lys Val Cys Gly Cys Asp Glu Tyr Phe Leu Glu Lys Tyr Pro Leu
                355                 360                 365

Ser Gln Tyr Lys Tyr Ile Arg Ser Cys Ile Met Leu Gly Arg Met Pro
    370                 375                 380

Asn Leu Met Leu Met Ala Lys Glu Ser Leu Tyr Ser Gln Leu Pro Met
385                 390                 395                 400

Asp Cys Phe Thr Met Pro Ser Tyr Ser Arg Arg Ile Ser Thr Ala Thr
                405                 410                 415

Pro Tyr Met Asn Gly Glu Thr Ser Thr Lys Ser Leu Trp Val Ile Asn
                420                 425                 430

Ser Ala Leu Arg Ile Lys Ile Leu Cys Ala Thr Tyr Val Asn Val Asn
                435                 440                 445

Ile Arg Asp Ile Asp Lys Ile Tyr Val Arg Thr Gly Ile Tyr His Gly
                450                 455                 460

Gly Glu Pro Leu Cys Asp Asn Val Asn Thr Gln Arg Val Pro Cys Ser
465                 470                 475                 480

Asn Pro Arg Trp Asn Glu Trp Leu Asn Tyr Asp Ile Tyr Ile Pro Asp
                485                 490                 495

Leu Pro Arg Ala Ala Arg Leu Cys Leu Ser Ile Cys Ser Val Lys Gly
                500                 505                 510

Arg Lys Gly Ala Lys Glu His Cys Pro Leu Ala Trp Gly Asn Ile
                515                 520                 525

Asn Leu Phe Asp Tyr Thr Asp Thr Leu Val Ser Gly Lys Met Ala Leu
                530                 535                 540

Asn Leu Trp Pro Val Pro His Gly Leu Glu Asp Leu Leu Asn Pro Ile
545                 550                 555                 560

Gly Val Thr Gly Ser Asn Pro Asn Lys Glu Thr Pro Cys Leu Glu Leu
                565                 570                 575

Glu Phe Asp Trp Phe Ser Ser Val Val Lys Phe Pro Asp Met Ser Val
                580                 585                 590

Ile Glu Glu His Ala Asn Trp Ser Val Ser Arg Glu Ala Gly Phe Ser
                595                 600                 605

Tyr Ser His Ala Gly Leu Ser Asn Arg Leu Ala Arg Asp Asn Glu Leu
                610                 615                 620

Arg Glu Asn Asp Lys Glu Gln Leu Lys Ala Ile Ser Thr Arg Asp Pro
625                 630                 635                 640

Leu Ser Glu Ile Thr Glu Gln Glu Lys Asp Phe Leu Trp Ser His Arg
                645                 650                 655

His Tyr Cys Val Thr Ile Pro Glu Ile Leu Pro Lys Leu Leu Leu Ser
                660                 665                 670
```

-continued

Val Lys Trp Asn Ser Arg Asp Glu Val Ala Gln Met Tyr Cys Leu Val
            675                 680                 685

Lys Asp Trp Pro Pro Ile Lys Pro Glu Gln Ala Met Glu Leu Leu Asp
690                 695                 700

Cys Asn Tyr Pro Asp Pro Met Val Arg Gly Phe Ala Val Arg Cys Leu
705                 710                 715                 720

Glu Lys Tyr Leu Thr Asp Asp Lys Leu Ser Gln Tyr Leu Ile Gln Leu
            725                 730                 735

Val Gln Val Leu Lys Tyr Glu Gln Tyr Leu Asp Asn Leu Leu Val Arg
                740                 745                 750

Phe Leu Leu Lys Lys Ala Leu Thr Asn Gln Arg Ile Gly His Phe Phe
            755                 760                 765

Phe Trp His Leu Lys Ser Glu Met His Asn Lys Thr Val Ser Gln Arg
            770                 775                 780

Phe Gly Leu Leu Leu Glu Ser Tyr Cys Arg Ala Cys Gly Met Tyr Leu
785                 790                 795                 800

Lys His Leu Asn Arg Gln Val Glu Ala Met Glu Lys Leu Ile Asn Leu
                805                 810                 815

Thr Asp Ile Leu Lys Gln Glu Lys Lys Asp Glu Thr Gln Lys Val Gln
            820                 825                 830

Met Lys Phe Leu Val Glu Gln Met Arg Arg Pro Asp Phe Met Asp Ala
            835                 840                 845

Leu Gln Gly Phe Leu Ser Pro Leu Asn Pro Ala His Gln Leu Gly Asn
            850                 855                 860

Leu Arg Leu Glu Glu Cys Arg Ile Met Ser Ser Ala Lys Arg Pro Leu
865                 870                 875                 880

Trp Leu Asn Trp Glu Asn Pro Asp Ile Met Ser Glu Leu Leu Phe Gln
                885                 890                 895

Asn Asn Glu Ile Ile Phe Lys Asn Gly Asp Asp Leu Arg Gln Asp Met
            900                 905                 910

Leu Thr Leu Gln Ile Ile Arg Ile Met Glu Asn Ile Trp Gln Asn Gln
            915                 920                 925

Gly Leu Asp Leu Arg Met Leu Pro Tyr Gly Cys Leu Ser Ile Gly Asp
930                 935                 940

Cys Val Gly Leu Ile Glu Val Val Arg Asn Ser His Thr Ile Met Gln
945                 950                 955                 960

Ile Gln Cys Lys Gly Gly Leu Lys Gly Ala Leu Gln Phe Asn Ser His
                965                 970                 975

Thr Leu His Gln Trp Leu Lys Asp Lys Asn Lys Gly Glu Ile Tyr Asp
            980                 985                 990

Ala Ala Ile Asp Leu Phe Thr Arg  Ser Cys Ala Gly Tyr  Cys Val Ala
            995                 1000                1005

Thr Phe  Ile Leu Gly Ile Gly  Asp Arg His Asn Ser  Asn Ile Met
    1010                1015                1020

Val Lys  Asp Asp Gly Gln Leu  Phe His Ile Asp Phe  Gly His Phe
    1025                1030                1035

Leu Asp  His Lys Lys Lys  Phe Gly Tyr Lys Arg  Glu Arg Val
    1040                1045                1050

Pro Phe  Val Leu Thr Gln Asp  Phe Leu Ile Val Ile  Ser Lys Gly
    1055                1060                1065

Ala Gln  Glu Cys Thr Lys Thr  Arg Glu Phe Glu Arg  Phe Gln Glu
    1070                1075                1080

Met Cys  Tyr Lys Ala Tyr Leu  Ala Ile Arg Gln His  Ala Asn Leu

```
                    1085                1090                1095

Phe Ile Asn Leu Phe Ser Met Met Leu Gly Ser Gly Met Pro Glu
            1100                1105                1110

Leu Gln Ser Phe Asp Asp Ile Ala Tyr Ile Arg Lys Thr Leu Ala
            1115                1120                1125

Leu Asp Lys Thr Glu Gln Glu Ala Leu Glu Tyr Phe Met Lys Gln
            1130                1135                1140

Met Asn Asp Ala His His Gly Gly Trp Thr Thr Lys Met Asp Trp
            1145                1150                1155

Ile Phe His Thr Ile Lys Gln His Ala Leu Asn Glu Leu Gly Gly
            1160                1165                1170

Ala His His His His His His
            1175                1180

<210> SEQ ID NO 5
<211> LENGTH: 615
<212> TYPE: PRT
<213> ORGANISM: Artificial
<220> FEATURE:
<223> OTHER INFORMATION: Fusion protein used for autophagy assay
<220> FEATURE:
<221> NAME/KEY: mCherry protein
<222> LOCATION: (1)..(236)
<220> FEATURE:
<221> NAME/KEY: GFP
<222> LOCATION: (241)..(479)
<220> FEATURE:
<221> NAME/KEY: LC3A
<222> LOCATION: (495)..(615)

<400> SEQUENCE: 5

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
```

```
            210                 215                 220
Arg His Ser Thr Gly Gly Met Asp Glu Leu Tyr Lys Pro Val Ala Thr
225                 230                 235                 240

Met Val Ser Lys Gly Glu Glu Leu Phe Thr Gly Val Val Pro Ile Leu
                245                 250                 255

Val Glu Leu Asp Gly Asp Val Asn Gly His Lys Phe Ser Val Ser Gly
                260                 265                 270

Glu Gly Glu Gly Asp Ala Thr Tyr Gly Lys Leu Thr Leu Lys Phe Ile
            275                 280                 285

Cys Thr Thr Gly Lys Leu Pro Val Pro Trp Pro Thr Leu Val Thr Thr
        290                 295                 300

Leu Thr Tyr Gly Val Gln Cys Phe Ser Arg Tyr Pro Asp His Met Lys
305                 310                 315                 320

Gln His Asp Phe Phe Lys Ser Ala Met Pro Glu Gly Tyr Val Gln Glu
                325                 330                 335

Arg Thr Ile Phe Phe Lys Asp Asp Gly Asn Tyr Lys Thr Arg Ala Glu
                340                 345                 350

Val Lys Phe Glu Gly Asp Thr Leu Val Asn Arg Ile Glu Leu Lys Gly
            355                 360                 365

Ile Asp Phe Lys Glu Asp Gly Asn Ile Leu Gly His Lys Leu Glu Tyr
        370                 375                 380

Asn Tyr Asn Ser His Asn Val Tyr Ile Met Ala Asp Lys Gln Lys Asn
385                 390                 395                 400

Gly Ile Lys Val Asn Phe Lys Ile Arg His Asn Ile Glu Asp Gly Ser
                405                 410                 415

Val Gln Leu Ala Asp His Tyr Gln Gln Asn Thr Pro Ile Gly Asp Gly
                420                 425                 430

Pro Val Leu Leu Pro Asp Asn His Tyr Leu Ser Thr Gln Ser Ala Leu
            435                 440                 445

Ser Lys Asp Pro Asn Glu Lys Arg Asp His Met Val Leu Leu Glu Phe
        450                 455                 460

Val Thr Ala Ala Gly Ile Thr Leu Gly Met Asp Glu Leu Tyr Lys Ser
465                 470                 475                 480

Gly Leu Arg Ser Arg Ala Gln Ala Ser Asn Ser Ala Val Asp Met Pro
                485                 490                 495

Ser Asp Arg Pro Phe Lys Gln Arg Arg Ser Phe Ala Ser Arg Cys Lys
                500                 505                 510

Glu Val Gln Gln Ile Arg Asp Gln His Pro Ser Lys Ile Pro Val Ile
            515                 520                 525

Ile Glu Arg Tyr Lys Gly Glu Lys Gln Leu Pro Val Leu Asp Lys Thr
        530                 535                 540

Lys Phe Leu Val Pro Asp His Val Asn Met Ser Glu Leu Val Lys Ile
545                 550                 555                 560

Ile Arg Arg Arg Leu Gln Leu Asn Pro Thr Gln Ala Phe Phe Leu Leu
                565                 570                 575

Val Asn Gln His Ser Met Val Ser Val Ser Thr Pro Ile Ala Asp Ile
                580                 585                 590

Tyr Glu Gln Glu Lys Asp Glu Asp Gly Phe Leu Tyr Met Val Tyr Ala
            595                 600                 605

Ser Gln Glu Thr Phe Gly Phe
        610                 615
```